United States Patent
Larkin et al.

(10) Patent No.: US 11,285,340 B2
(45) Date of Patent: Mar. 29, 2022

(54) HIGH BANDWIDTH BINARY MULTI-LEAF COLLIMATOR DESIGN

(71) Applicant: RefleXion Medical, Inc., Hayward, CA (US)

(72) Inventors: David Larkin, Menlo Park, CA (US); William Knapp, El Granada, CA (US); Layton Hale, Castro Valley, CA (US)

(73) Assignee: RefleXion Medical, Inc., Hayward, CA (US)

( * ) Notice: Subject to any disclaimer, the term of this patent is extended or adjusted under 35 U.S.C. 154(b) by 126 days.

(21) Appl. No.: 16/677,200

(22) Filed: Nov. 7, 2019

(65) Prior Publication Data

US 2020/0164230 A1    May 28, 2020

Related U.S. Application Data

(62) Division of application No. 15/179,823, filed on Jun. 10, 2016, now Pat. No. 10,500,416.

(60) Provisional application No. 62/335,571, filed on May 12, 2016, provisional application No. 62/173,824, filed on Jun. 10, 2015.

(51) Int. Cl.
*A61N 5/10* (2006.01)
*G21K 1/04* (2006.01)

(52) U.S. Cl.
CPC ............ *A61N 5/1045* (2013.01); *G21K 1/046* (2013.01); *A61N 2005/1074* (2013.01)

(58) Field of Classification Search
CPC .......... A61N 5/1042; A61N 2005/1074; A61N 5/1045; G21K 1/046; G21K 1/04
See application file for complete search history.

(56) References Cited

U.S. PATENT DOCUMENTS

| | | | |
|---|---|---|---|
| 3,418,475 A | 12/1968 | Hudgens | |
| 3,668,399 A | 6/1972 | Cahill et al. | |
| 3,721,826 A * | 3/1973 | Thomas, Jr. | G21K 1/04 378/160 |
| 3,779,135 A * | 12/1973 | Sugimura | F15B 11/076 91/45 |
| 3,794,840 A | 2/1974 | Scott | |
| 3,906,233 A | 9/1975 | Vogel | |

(Continued)

FOREIGN PATENT DOCUMENTS

| | | |
|---|---|---|
| CN | 2529663 Y | 1/2003 |
| CN | 1681436 A | 10/2005 |

(Continued)

OTHER PUBLICATIONS

Notice of Allowance dated Apr. 30, 2020, for U.S. Appl. No. 15/814,222, filed on Nov. 15, 2017, 10 pages.

(Continued)

*Primary Examiner* — Wyatt A Stoffa
(74) *Attorney, Agent, or Firm* — Cooley LLP

(57) ABSTRACT

Described herein are multi-leaf collimators that comprise leaf drive mechanisms. The leaf drive mechanisms can be used in binary multi-leaf collimators used in emission-guided radiation therapy. One variation of a multi-leaf collimator comprises a pneumatics-based leaf drive mechanism. Another variation of a multi-leaf collimator comprises a spring-based leaf drive mechanism having a spring resonator.

14 Claims, 50 Drawing Sheets

(56) References Cited

U.S. PATENT DOCUMENTS

| | | |
|---|---|---|
| 4,241,644 A * | 12/1980 | Schertler .............. F16K 31/406 91/447 |
| 4,246,488 A * | 1/1981 | Hura ...................... G21K 1/10 378/151 |
| 4,361,902 A | 11/1982 | Brandt et al. |
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,628,499 A | 12/1986 | Hammett |
| 4,642,464 A | 2/1987 | Mullani |
| 4,647,779 A | 3/1987 | Wong |
| 4,677,299 A | 6/1987 | Wong |
| 4,760,589 A | 7/1988 | Siczek |
| 4,794,629 A * | 12/1988 | Pastyr ................. A61N 5/1042 378/146 |
| 4,868,844 A | 9/1989 | Nunan |
| 5,010,312 A | 4/1991 | Motykiewicz |
| 5,075,554 A | 12/1991 | Yunker et al. |
| 5,206,512 A | 4/1993 | Iwao |
| 5,207,223 A | 5/1993 | Adler |
| 5,317,616 A * | 5/1994 | Swerdloff ............ A61N 5/1042 378/65 |
| 5,329,567 A | 7/1994 | Ikebe |
| 5,351,280 A * | 9/1994 | Swerdloff ............ A61N 5/1042 378/150 |
| 5,390,225 A | 2/1995 | Hawman |
| 5,394,452 A * | 2/1995 | Swerdloff ............ A61N 5/1042 378/150 |
| 5,396,534 A | 3/1995 | Thomas |
| 5,408,591 A | 4/1995 | Shih et al. |
| 5,418,827 A | 5/1995 | Deasy et al. |
| 5,442,675 A | 8/1995 | Swerdloff et al. |
| 5,596,619 A * | 1/1997 | Carol ..................... A61N 5/103 378/65 |
| 5,668,371 A | 9/1997 | Deasy et al. |
| 5,724,400 A | 3/1998 | Swerdloff et al. |
| 5,751,781 A | 5/1998 | Brown et al. |
| 5,757,881 A * | 5/1998 | Hughes ................ A61N 5/1042 250/505.1 |
| 5,813,985 A | 9/1998 | Carroll |
| 5,818,902 A | 10/1998 | Yu |
| 5,851,182 A | 12/1998 | Sahadevan |
| 5,889,834 A | 3/1999 | Vilsmeier et al. |
| 5,937,028 A | 8/1999 | Tybinkowski et al. |
| 6,052,436 A * | 4/2000 | Huttner ................ A61N 5/1042 250/505.1 |
| 6,180,943 B1 | 1/2001 | Lange |
| 6,184,530 B1 | 2/2001 | Hines et al. |
| 6,188,748 B1 | 2/2001 | Pastyr et al. |
| 6,260,005 B1 | 7/2001 | Yang et al. |
| 6,281,505 B1 | 8/2001 | Hines et al. |
| 6,330,300 B1 | 12/2001 | Siochi |
| 6,385,288 B1 | 5/2002 | Kanematsu |
| 6,388,816 B2 | 5/2002 | Brown et al. |
| 6,396,902 B2 | 5/2002 | Tybinkowski et al. |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,459,769 B1 | 10/2002 | Cosman |
| 6,504,899 B2 | 1/2003 | Pugachev et al. |
| 6,560,311 B1 | 5/2003 | Shepard et al. |
| 6,618,467 B1 | 9/2003 | Ruchala et al. |
| 6,661,866 B1 | 12/2003 | Limkeman et al. |
| 6,696,694 B2 | 2/2004 | Pastyr et al. |
| 6,730,924 B1 | 5/2004 | Pastyr et al. |
| 6,735,277 B2 | 5/2004 | McNutt et al. |
| 6,744,493 B1 | 6/2004 | Johnson et al. |
| 6,763,588 B1 | 7/2004 | Nilsson et al. |
| 6,778,636 B1 | 8/2004 | Andrews |
| 6,792,078 B2 | 9/2004 | Kato et al. |
| 6,794,653 B2 | 9/2004 | Wainer et al. |
| 6,810,103 B1 | 10/2004 | Tybinkowski et al. |
| 6,810,108 B2 | 10/2004 | Clark et al. |
| 6,813,336 B1 | 11/2004 | Siochi |
| 6,831,961 B1 | 12/2004 | Tybinkowski et al. |
| 6,865,254 B2 | 3/2005 | Nafstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,020,245 B2 | 3/2006 | Noguchi |
| 7,026,622 B2 | 4/2006 | Kojima et al. |
| 7,110,808 B2 | 9/2006 | Adair |
| 7,154,096 B2 | 12/2006 | Amano |
| 7,167,542 B2 | 1/2007 | Juschka et al. |
| 7,188,999 B2 | 3/2007 | Mihara et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,310,410 B2 | 12/2007 | Sohal et al. |
| 7,362,849 B2 | 4/2008 | Short et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,412,029 B2 | 8/2008 | Myles |
| 7,446,328 B2 | 11/2008 | Rigney et al. |
| 7,453,983 B2 | 11/2008 | Schildkraut et al. |
| 7,469,035 B2 | 12/2008 | Keall et al. |
| 7,507,975 B2 | 3/2009 | Mohr |
| 7,519,162 B2 * | 4/2009 | Hoffmann ............ A61B 6/0414 378/155 |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,609,811 B1 | 10/2009 | Siljamaki et al. |
| 7,627,082 B2 | 12/2009 | Kojima et al. |
| 7,629,599 B2 | 12/2009 | Hashimoto |
| 7,639,853 B2 | 12/2009 | Olivera et al. |
| 7,642,534 B2 | 1/2010 | Johnsen |
| 7,656,999 B2 | 2/2010 | Hui et al. |
| 7,742,575 B2 | 6/2010 | Bourne |
| 7,755,055 B2 | 7/2010 | Schilling |
| 7,755,057 B2 | 7/2010 | Kim |
| 7,778,691 B2 | 8/2010 | Zhang et al. |
| 7,783,007 B2 * | 8/2010 | Echner .................. G21K 1/04 378/65 |
| 7,792,252 B2 | 9/2010 | Bohn |
| 7,795,590 B2 | 9/2010 | Takahashi et al. |
| 7,826,593 B2 | 11/2010 | Svensson et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,059,782 B2 | 11/2011 | Brown |
| 8,063,376 B2 | 11/2011 | Maniawski et al. |
| 8,067,751 B2 | 11/2011 | Mohr |
| 8,090,074 B2 | 1/2012 | Filiberti et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,139,718 B2 | 3/2012 | Brown et al. |
| 8,144,962 B2 | 3/2012 | Busch et al. |
| 8,148,695 B2 | 4/2012 | Takahashi et al. |
| 8,213,569 B2 | 7/2012 | Zaiki et al. |
| 8,232,535 B2 | 7/2012 | Olivera et al. |
| 8,269,195 B2 | 9/2012 | Rigney et al. |
| 8,278,633 B2 | 10/2012 | Nord et al. |
| 8,280,002 B2 | 10/2012 | Bani-Hashemi et al. |
| 8,304,738 B2 | 11/2012 | Gagnon et al. |
| 8,335,296 B2 | 12/2012 | Dehler et al. |

(56) References Cited

U.S. PATENT DOCUMENTS

| | | | |
|---|---|---|---|
| 8,357,903 B2 | 1/2013 | Wang et al. |
| 8,384,049 B1 | 2/2013 | Broad |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,467,499 B2 | 6/2013 | Furth et al. |
| 8,483,803 B2 | 7/2013 | Partain et al. |
| 8,519,370 B2 | 8/2013 | Luzzara |
| 8,536,547 B2 | 9/2013 | Maurer, Jr. et al. |
| 8,537,373 B2 | 9/2013 | Humphrey |
| 8,581,196 B2 | 11/2013 | Yamaya et al. |
| 8,604,450 B2 | 12/2013 | Mohr |
| 8,617,422 B2 | 12/2013 | Koschan et al. |
| 8,637,841 B2 | 1/2014 | Prince et al. |
| 8,664,610 B2 | 3/2014 | Chuang |
| 8,664,618 B2 | 3/2014 | Yao |
| 8,699,668 B2 | 4/2014 | Demlanovlch, II |
| 8,712,012 B2 | 4/2014 | O'Connor |
| 8,748,825 B2 | 6/2014 | Mazin |
| 8,798,233 B2 | 8/2014 | Geisler et al. |
| 8,816,307 B2 | 8/2014 | Kuusela et al. |
| 8,837,681 B2 | 9/2014 | Liu et al. |
| 9,031,204 B2 | 5/2015 | Echner et al. |
| 9,082,520 B2 | 7/2015 | Prince et al. |
| 9,205,281 B2 | 12/2015 | Mazin |
| 9,324,468 B2 | 4/2016 | Mansfield et al. |
| 9,370,672 B2 | 6/2016 | Parsai et al. |
| 9,406,411 B2 | 8/2016 | Sayeh et al. |
| 9,437,339 B2 | 9/2016 | Echner |
| 9,437,340 B2 | 9/2016 | Echner et al. |
| 9,443,633 B2* | 9/2016 | Orton ............... G21K 1/046 |
| 9,480,860 B2 | 11/2016 | Gaudio |
| 9,498,167 B2 | 11/2016 | Mostafavi et al. |
| 9,572,998 B2 | 2/2017 | Willcut et al. |
| 9,627,098 B2 | 4/2017 | Ganguly |
| 9,774,838 B2 | 9/2017 | Chappelow et al. |
| 9,795,805 B2 | 10/2017 | Mellenberg et al. |
| 9,931,521 B2 | 4/2018 | Hsu et al. |
| 9,943,705 B2 | 4/2018 | Chappelow et al. |
| 9,950,193 B2 | 4/2018 | Chappelow et al. |
| 9,974,494 B2 | 5/2018 | Mostafavi et al. |
| 10,026,517 B2 | 7/2018 | Constantin et al. |
| 10,500,416 B2 | 12/2019 | Larkin et al. |
| 10,695,586 B2 | 6/2020 | Harper et al. |
| 2002/0191734 A1 | 12/2002 | Kojima et al. |
| 2002/0193685 A1 | 12/2002 | Mate et al. |
| 2003/0219098 A1 | 11/2003 | McNutt et al. |
| 2004/0030246 A1 | 2/2004 | Townsend et al. |
| 2004/0057557 A1 | 3/2004 | Nafstadius |
| 2004/0158416 A1 | 8/2004 | Slates |
| 2005/0063516 A1* | 3/2005 | Kato ............... A61N 5/1042 |
| | | | 378/152 |
| 2006/0002511 A1 | 1/2006 | Miller et al. |
| 2006/0113482 A1 | 6/2006 | Pelizzari et al. |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0193441 A1* | 8/2006 | Cadman ............... G21K 1/046 |
| | | | 378/153 |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0043289 A1 | 2/2007 | Adair |
| 2007/0055144 A1 | 3/2007 | Neustadter et al. |
| 2007/0164239 A1 | 7/2007 | Terwilliger et al. |
| 2007/0211857 A1 | 9/2007 | Urano et al. |
| 2007/0221869 A1 | 9/2007 | Song |
| 2007/0265528 A1 | 11/2007 | Xu et al. |
| 2008/0031404 A1 | 2/2008 | Khamene et al. |
| 2008/0130825 A1 | 6/2008 | Fu et al. |
| 2008/0152085 A1 | 6/2008 | Saracen et al. |
| 2008/0205588 A1 | 8/2008 | Kim |
| 2008/0253516 A1 | 10/2008 | Hui et al. |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0116616 A1 | 5/2009 | Lu et al. |
| 2009/0256078 A1 | 10/2009 | Mazin |
| 2010/0040197 A1 | 2/2010 | Maniawski et al. |
| 2010/0054408 A1* | 3/2010 | Echner ............... A61N 5/1042 |
| | | | 378/65 |
| 2010/0054412 A1 | 3/2010 | Brinks et al. |
| 2010/0067660 A1 | 3/2010 | Maurer, Jr. et al. |
| 2010/0069742 A1 | 3/2010 | Partain et al. |
| 2011/0044429 A1 | 2/2011 | Takahashi et al. |
| 2011/0092814 A1 | 4/2011 | Yamaya et al. |
| 2011/0272600 A1 | 11/2011 | Bert et al. |
| 2011/0301449 A1 | 12/2011 | Maurer, Jr. |
| 2011/0309255 A1 | 12/2011 | Bert et al. |
| 2011/0313231 A1 | 12/2011 | Guertin et al. |
| 2012/0035470 A1 | 2/2012 | Kuduvalli et al. |
| 2012/0203490 A1* | 8/2012 | Sayeh ............... A61N 5/1075 |
| | | | 702/105 |
| 2012/0230464 A1 | 9/2012 | Ling et al. |
| 2013/0266116 A1 | 10/2013 | Abenaim et al. |
| 2014/0079179 A1 | 3/2014 | Takagaki et al. |
| 2014/0107390 A1 | 4/2014 | Brown et al. |
| 2014/0228613 A1 | 8/2014 | Mazin et al. |
| 2014/0239204 A1* | 8/2014 | Orton ............... G21K 1/046 |
| | | | 250/505.1 |
| 2014/0249348 A1 | 9/2014 | Mazin |
| 2015/0150740 A1* | 6/2015 | Lewald ............... A61G 7/103 |
| | | | 600/415 |
| 2015/0170778 A1* | 6/2015 | Echner ............... G21K 1/046 |
| | | | 250/505.1 |
| 2015/0190658 A1 | 7/2015 | Yu |
| 2016/0073977 A1 | 3/2016 | Mazin |
| 2016/0279444 A1 | 9/2016 | Schlosser |
| 2016/0325117 A1 | 11/2016 | Arai |
| 2016/0325118 A1 | 11/2016 | Arai |
| 2017/0087388 A1 | 3/2017 | Kauppinen et al. |
| 2017/0096612 A1 | 4/2017 | Mohr et al. |
| 2017/0128746 A1 | 5/2017 | Zwart et al. |
| 2017/0143995 A1 | 5/2017 | Bergfjord |
| 2018/0012676 A1 | 1/2018 | Xu et al. |
| 2018/0021596 A1 | 1/2018 | Arai et al. |
| 2018/0043186 A1 | 2/2018 | Willcut et al. |
| 2018/0133518 A1 | 5/2018 | Harper et al. |
| 2018/0193671 A1 | 7/2018 | Chappelow et al. |
| 2020/0368557 A1 | 11/2020 | Harper et al. |

FOREIGN PATENT DOCUMENTS

| | | |
|---|---|---|
| CN | 1960780 A | 5/2007 |
| CN | 101970043 A | 2/2011 |
| CN | 102755696 A | 10/2012 |
| CN | 102760505 A | 10/2012 |
| CN | 202620505 U | 12/2012 |
| DE | 10-2008-053321 A1 | 5/2010 |
| DE | 10-2013-205606 A1 | 10/2014 |
| EP | 1 815 883 B1 | 4/2009 |
| EP | 1 501 604 B1 | 12/2009 |
| EP | 1 898 234 B1 | 4/2010 |
| EP | 2 188 815 B1 | 11/2011 |
| EP | 2 280 764 B1 | 8/2012 |
| EP | 2 225 001 B1 | 6/2013 |
| EP | 2 090 333 B1 | 10/2013 |
| EP | 2 687 259 A1 | 1/2014 |
| EP | 1 364 375 B1 | 4/2014 |
| EP | 2 543 045 B1 | 5/2014 |
| EP | 2 020 006 B1 | 12/2014 |
| EP | 2 874 702 B1 | 9/2016 |
| EP | 2 874 703 B1 | 9/2016 |
| EP | 3 088 048 B1 | 2/2018 |
| EP | 3 307 385 A1 | 4/2018 |
| EP | 3 307 386 A1 | 4/2018 |
| EP | 3 308 382 A1 | 4/2018 |
| EP | 2 542 306 B1 | 5/2018 |
| JP | H-8-511451 A | 12/1996 |
| JP | 03-277350 A | 10/2003 |
| JP | 2003-534823 A | 11/2003 |

(56) References Cited

FOREIGN PATENT DOCUMENTS

| | | |
|---|---|---|
| JP | 2007-502166 A | 2/2007 |
| JP | 2007-507246 A | 3/2007 |
| JP | 2008-173299 A | 7/2008 |
| NL | 9520013 A | 2/1997 |
| WO | WO-89/10090 A1 | 11/1989 |
| WO | WO-95/22241 A1 | 8/1995 |
| WO | WO-00/15299 A1 | 3/2000 |
| WO | WO-2004/017832 A2 | 3/2004 |
| WO | WO-2004/017832 A3 | 3/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/124760 A1 | 11/2007 |
| WO | WO-2008/019118 A2 | 2/2008 |
| WO | WO-2008/019118 A3 | 2/2008 |
| WO | WO-2008/024463 A2 | 2/2008 |
| WO | WO-2008/024463 A3 | 2/2008 |
| WO | WO-2009/114117 A2 | 9/2009 |
| WO | WO-2009/114117 A3 | 9/2009 |
| WO | WO-2010/015358 A1 | 2/2010 |
| WO | WO-2012/135771 A1 | 10/2012 |
| WO | WO-2015/161036 A1 | 10/2015 |
| WO | WO-2016/200462 A1 | 12/2016 |
| WO | WO-2016/200463 A1 | 12/2016 |
| WO | WO-2016/200464 A1 | 12/2016 |
| WO | WO-2016/201348 A1 | 12/2016 |
| WO | WO-2018/113310 A1 | 6/2018 |

OTHER PUBLICATIONS

Chang, J.Y. et al. (2008). "Image-guided radiation therapy for non-small cell lung cancer," *J. Thorac. Oncol.* 3(2):177-186.

Chen, Y. et al. (2011). Dynamic tomotherapy delivery, *Am. Assoc. Phys. Med.* 38:3013-3024.

Erdi, Y.E. (2007). "The use of PET for radiotherapy," *Curr. Medical Imaging Reviews* 3(1):3-16.

Extended European Search Report dated Oct. 7, 2015, for European Patent Application No. 12 763 280.0, filed on Mar. 30, 2012, 11 pages.

Extended European Search Report dated Mar. 18, 2019, for European Patent Application No. 16 808 458.0, filed on Jun. 10, 2016, 8 pages.

Fan, Q et al. (2012). "Emission Guided Radiation Therapy for Lung and Prostrate Cancers: A Feasibility Study on a Digital Patient," *Med. Phys.* 39(11)7140-7152.

Fan, Q et al. (2013). "Toward a Planning Scheme for Emission Guided Radiation Therapy (EGRT): FDG Based TumorTracking in a Metastatic Breast Cancer Patient," *Med. Phys.* 40(8): 12 pages.

Final Office Action dated Nov. 1, 2018, for U.S. Appl. No. 15/179,823, filed on Jun. 10, 2016, 12 pages.

Gibbons, J.P. (2004). "Dose calculation and verification for tomotherapy," 2004 ACMP Meeting, Scottsdale, AZ., 71 total pages.

Handsfield, L.L. et al. (2014). "Phantomless patient-specific TomoTherapy QA via delivery performance monitoring and a secondary Monte Carlo dose calculation," *Med. Phys.* 41:101703-1-101703-9.

International Search Report dated Sep. 16, 2016, for PCT Application No. PCT/US2016/037051, filed on Jun. 10, 2016, 3 pages.

International Search Report dated Jul. 20, 2012, for PCT Patent Application No. PCT/US2012/031704, filed on Mar. 30, 2012, 2 pages.

International Search Report dated Mar. 7, 2018, for PCT Application No. PCT/US2017/061848, filed on Nov. 15, 2017, 4 pages.

Kapatoes, J.M. et al. (2001). "A feasible method for clinical delivery verification and dose reconstruction in tomotherapy," *Med. Phys.* 28:528-542.

Krouglicof, N. et al. (2013). "Development of a Novel PCB-Based Voice Coil Actuator for Opto-Mechatronic Applications," *presented at IEEE/RSJ International Conference on Intelligent Robots and Systems* (*IROS*), Tokyo, Japan, Nov. 3-7, 2013, pp. 5834-5840.

Mackie, T.R. et al. (Nov.-Dec. 1993). "Tomotherapy: A New Concept for the Delivery of Dynamic Conformal Radiotherapy," *Med. Phys.* 20(6):1709-1719.

Mazin, S. R. et al. (2010). "Emission-Guided Radiation Therapy: Biologic Targeting and Adaptive Treatment," *Journal of American College of Radiology* 7(12):989-990.

Non-Final Office Action dated Aug. 30, 2018, for U.S. Appl. No. 15/179,823, filed on Jun. 10, 2016, 11 pages.

Non-Final Office Action dated Mar. 8, 2019, for U.S. Appl. No. 15/179,823, filed on Jun. 10, 2016, 11 pages.

Non-Final Office Action dated Jan. 7, 2020, for U.S. Appl. No. 15/814,222, filed on Nov. 15, 2017, 13 pages.

Notice of Allowance dated Sep. 23, 2019, for U.S. Appl. No. 15/179,823, filed on Jun. 10, 2016, 10 pages.

Papanikolaou, N. et al. (2010). "MU-Tomo: Independent dose validation software for helical tomo therapy," *J. Cancer Sci. Ther.* 2:145-152.

Partial Supplementary European Search Report dated Jun. 25, 2015, for European Application No. 12 763 280.0, filed on Mar. 30, 2012, 6 pages.

Prabhakar, R. et al. (2007). "An Insight into PET-CT Based Radiotherapy Treatment Planning," *Cancer Therapy* (5):519-524.

Tashima, H. et al. (2012). "A Single-Ring Open PET Enabling PET Imaging During Radiotherapy," *Phys. Med. Biol.* 57(14):4705-4718.

Varian Medical Systems (2004). "DynamicTargeting™ Image-Guided Radiation Therapy—A Revolution in Cancer Care," *Business Briefing: US Oncology Review,* Abstract only, 2 pages.

https://web.archive.org/web/20150403230112/https://www.merriam-webster.com/dictionary/couple, retrieved Oct. 19, 2018.

Wikipedia (2016). "Scotch yoke," Retrieved from https://en.wikipedia.org/wiki/Scotch_yoke, 3 pages.

Written Opinion of the International Searching Authority dated Sep. 16, 2016, for PCT Application No. PCT/US2016/037051, filed on Jun. 10, 2016, 5 pages.

Written Opinion of the International Searching Authority dated Jul. 20, 2012, for PCT Patent Application No. PCT/US2012/031704, filed on Mar. 30, 2012, 10 pages.

Written Opinion of the International Searching Authority dated Mar. 7, 2018, for PCT Application No. PCT/US2017/061848, filed on Nov. 15, 2017, 5 pages.

Yamaya, T. et al. (2008). "A proposal of an open PET geometry," *Physics in Med. and Biology* 53:757-773.

Extended European Search Report dated Jun. 9, 2020, for EP Application No. 17 871 349.1, filed on Nov. 15, 2017, 6 pages.

\* cited by examiner

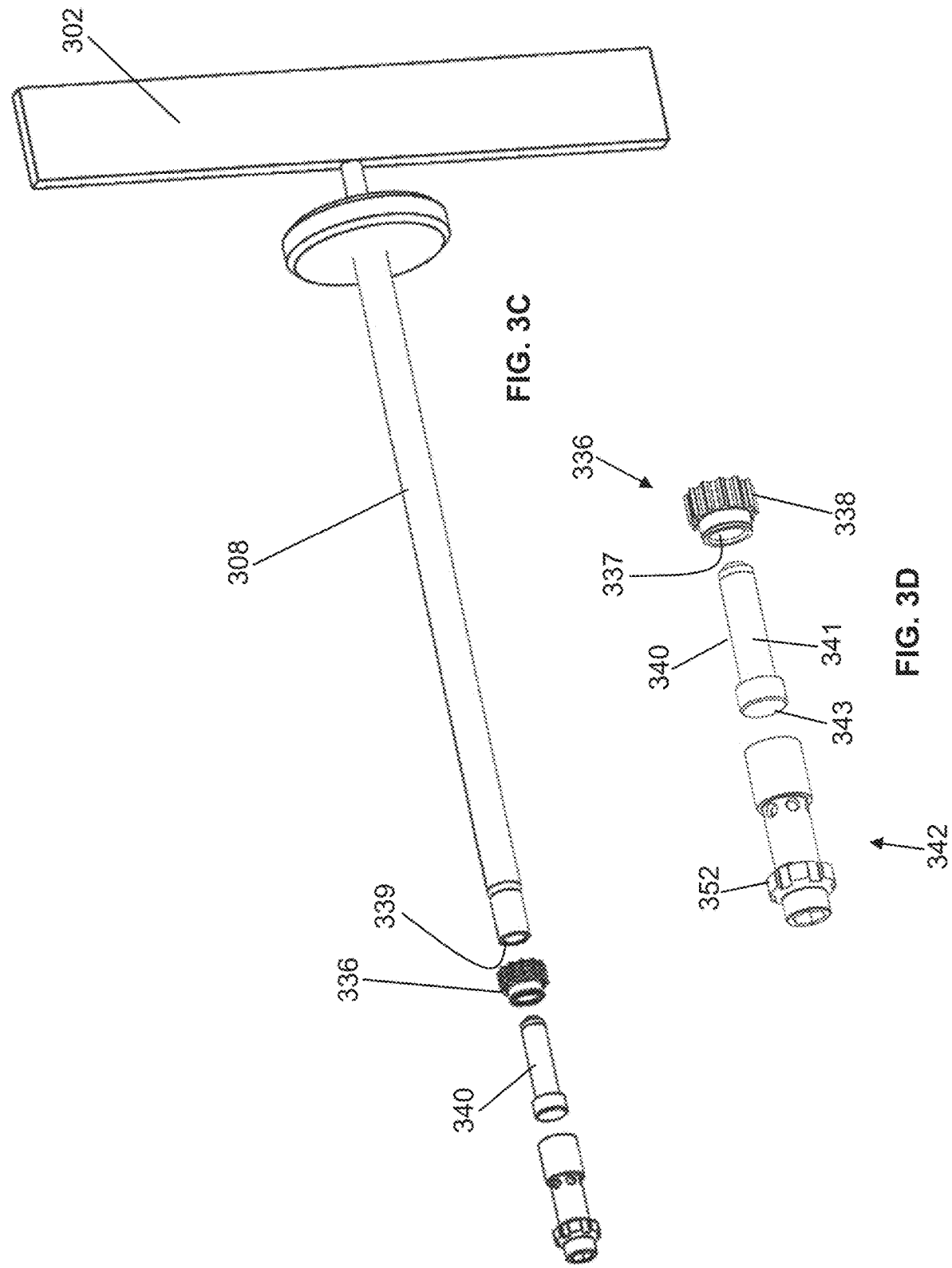

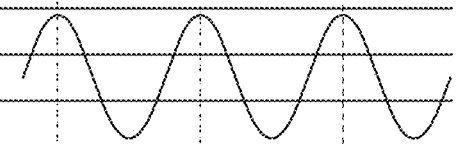
FIG. 9A
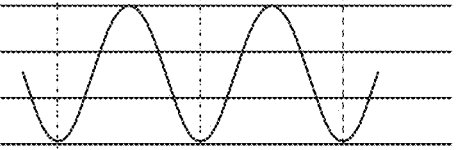
FIG. 9B
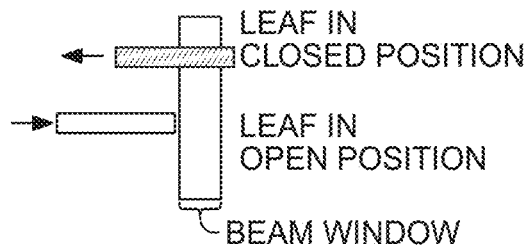
FIG. 9C
FIG. 9D

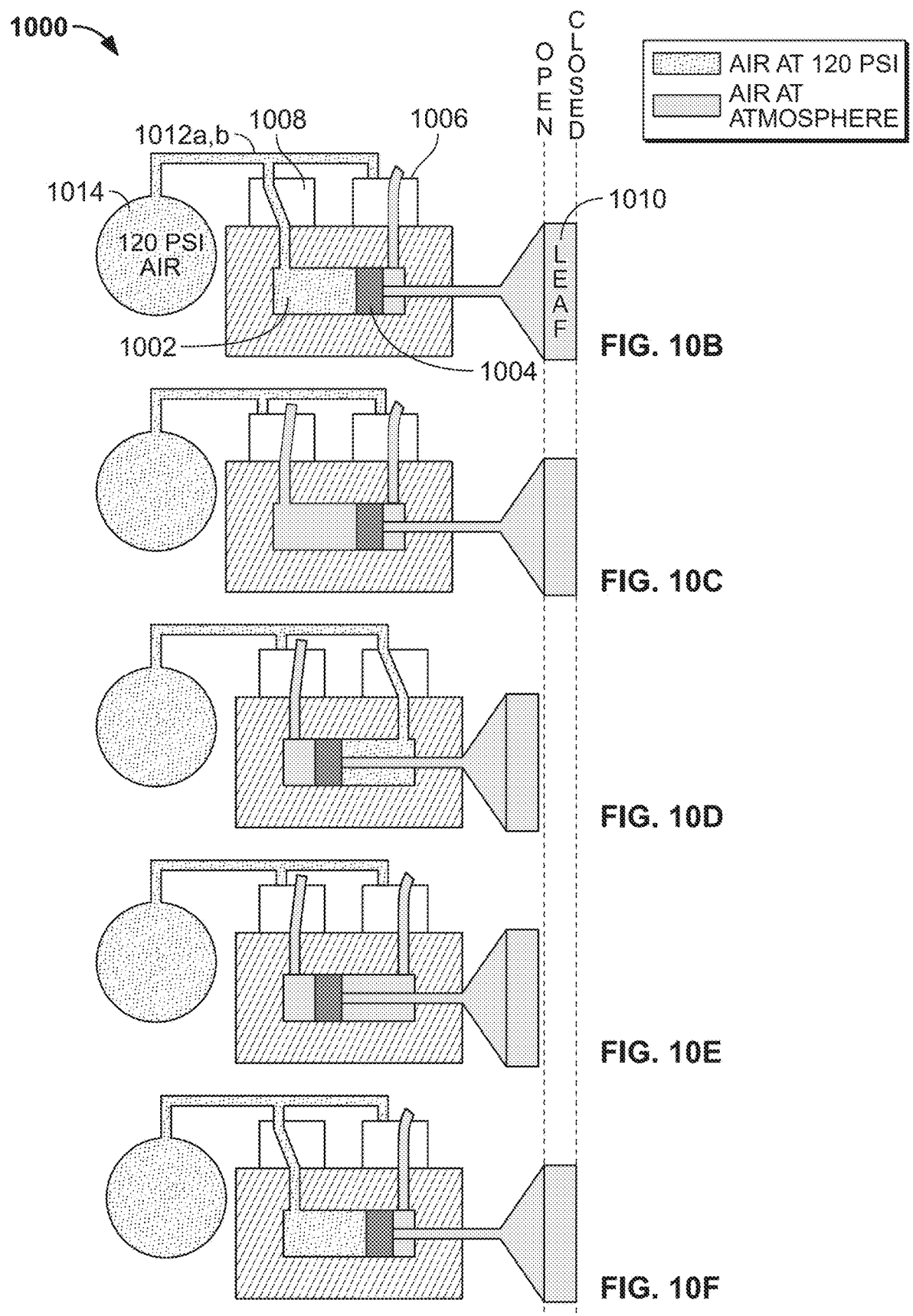

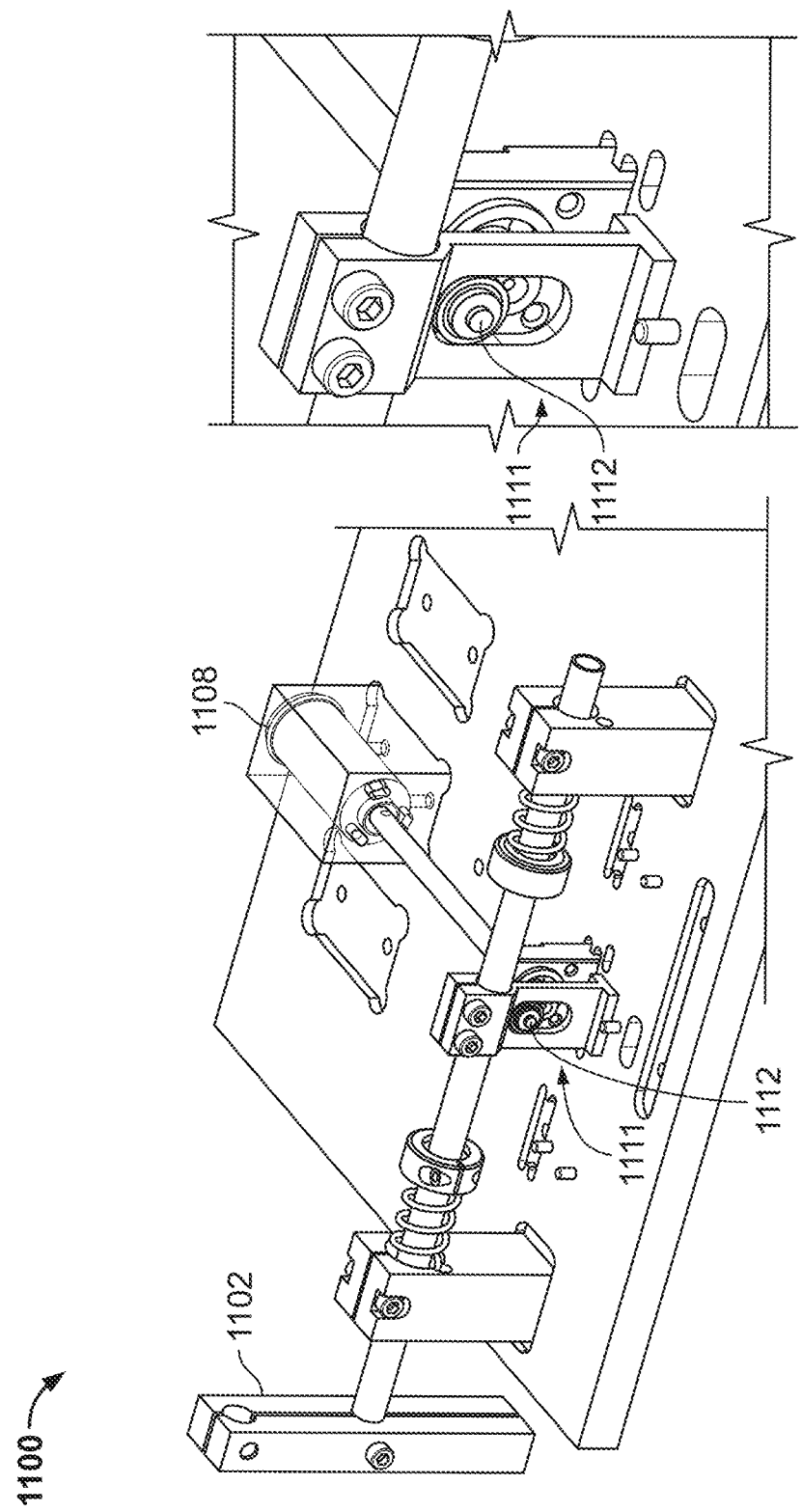

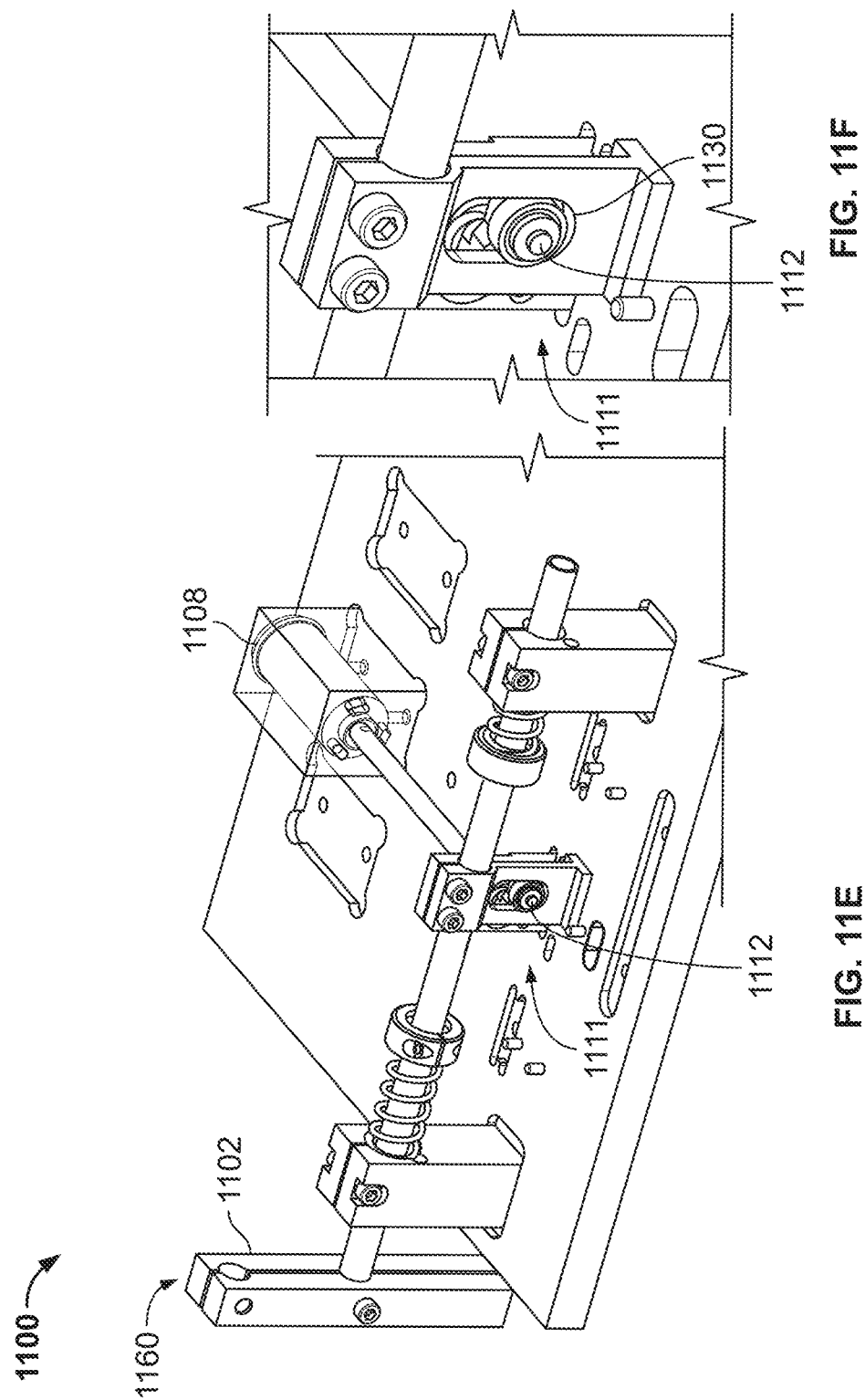

```
                                                              ┌─ 1550
                                                          ↙
┌─────────────────────────────────────────────────────────────────────────────┐
│ Step 1: Install eight chassis assemblies for leaf drive mechanism units 1541, 1542, 1543, 1544, 1545, │
│ 1546, 1547, 1548 to one or more plate (e.g., top plate 1530 and/or middle plate 1532 and/or bottom    │
│ plate 1534).                                                                                          │
└─────────────────────────────────────────────────────────────────────────────┘
                                      ↓
┌─────────────────────────────────────────────────────────────────────────────┐
│ Step 2: Install scotch yoke assembly from rear into drive unit 1548 such that the roller is within the │
│ scotch yoke slot.                                                                                      │
└─────────────────────────────────────────────────────────────────────────────┘
                                      ↓
┌─────────────────────────────────────────────────────────────────────────────┐
│ Step 3: Slide chassis of drive unit 1544 rearwards to make space for the actuator shaft installation at │
│ drive unit 1548.                                                                                       │
└─────────────────────────────────────────────────────────────────────────────┘
                                      ↓
┌─────────────────────────────────────────────────────────────────────────────┐
│ Step 4: Install the actuator shaft for drive unit 1548 by holding the roller (with tweezers) from the  │
│ rear end while engaging the actuator shaft to the roller, installing a bolt through the center of      │
│ actuator shaft to engage thread in the roller, and holding the roller (with wrench) from the rear and  │
│ torque the bolt to desired tightness (e.g., a M2.5 bolt torqued to about 1.4 Nm).                      │
└─────────────────────────────────────────────────────────────────────────────┘
                                      ↓
┌─────────────────────────────────────────────────────────────────────────────┐
│ Step 5: Repeat step 2 for drive unit 1547.                                                             │
└─────────────────────────────────────────────────────────────────────────────┘
                                      ↓
┌─────────────────────────────────────────────────────────────────────────────┐
│ Step 6: Slide the chassis for drive unit 1543 rearwards to make space for the actuator shaft           │
│ installation at drive unit 1547.                                                                       │
└─────────────────────────────────────────────────────────────────────────────┘
                                      ↓
┌─────────────────────────────────────────────────────────────────────────────┐
│ Step 7: Repeat step 4 for drive unit 1547.                                                             │
└─────────────────────────────────────────────────────────────────────────────┘
                                      ↓
┌─────────────────────────────────────────────────────────────────────────────┐
│ Step 8: Repeat step 2 for drive unit 1546.                                                             │
└─────────────────────────────────────────────────────────────────────────────┘
                                      ↓
┌─────────────────────────────────────────────────────────────────────────────┐
│ Step 9: Slide the chassis for drive unit 1542 rearwards to make space for the actuator shaft           │
│ installation at drive unit 1546.                                                                       │
└─────────────────────────────────────────────────────────────────────────────┘
                                      ↓
┌─────────────────────────────────────────────────────────────────────────────┐
│ Step 10: Repeat step 4 for drive unit 1546.                                                            │
└─────────────────────────────────────────────────────────────────────────────┘
                                      ↓
```

HIGH BANDWIDTH BINARY MULTI-LEAF COLLIMATOR DESIGN

CROSS-REFERENCE TO RELATED APPLICATIONS

This application is a divisional of U.S. patent application Ser. No. 15/179,823, filed Jun. 10, 2016, now issued as U.S. Pat. No. 10,500,416, which claims priority to U.S. Provisional Patent Application No. 62/173,824, filed Jun. 10, 2015 and U.S. Provisional Patent Application No. 62/335,571, filed May 12, 2016, the disclosures of which are hereby incorporated by reference in their entirety.

STATEMENT REGARDING FEDERALLY SPONSORED RESEARCH OR DEVELOPMENT

This invention was made in part during work supported by grant number 2R44CA153466-02A1 from the National Cancer Institute. The government may have certain rights in the invention.

BACKGROUND

Radiation therapy seeks to ablate tumor tissue using high-energy radiation such as X-rays. Radiation treatment plans are designed to balance the need to apply a sufficient dose of radiation to the entire tumor tissue volume with the need to apply as little radiation as possible so as not to damage healthy tissue surrounding the tumor. However, because treatment plans and the tumor images on which they are based are devised far in advance of the treatment session, the treatment plan may not account for changes in the tumor geometry and/or patient anatomy.

Furthermore, during a radiation therapy treatment session, minute tumor and/or patient movements may unintentionally expose non-tumorous tissue to radiation. Accordingly, radiation treatment systems that can precisely irradiate tumor tissue based on real-time tumor and patient data may be desirable.

BRIEF SUMMARY

Described herein are various mechanisms that may be suitable for use in a high-bandwidth multi-leaf collimator for an emission guided radiation therapy system. Emission guided radiation therapy (EGRT) systems may be configured to direct radiation to a tumor volume based on real-time tumor data, such as the location data of gamma ray photon emissions from a radioactive tracer accumulated in a tumor. EGRT systems are configured to apply a beam of radiation shortly after an emission is detected. Any of the high-bandwidth multi-leaf collimators described herein may be used in an EGRT system to reduce the latency between emission detection and radiation application. The mechanisms described below may facilitate the rapid and reliable movement of collimator leaves such that the collimator is capable of transitioning leaves between open and closed states in about 10 ms or less, e.g., about 8 ms or less, about 7 ms or less, about 6 ms or less, about 4 ms or less. Some variations of high-speed, high-bandwidth collimators may comprise one or more cam-based systems, spring systems, fluid-power (e.g., pneumatic) systems, slotted-link (e.g., scotch yoke) systems, and/or electromagnetic systems. In addition to mechanisms that facilitate rapid leaf movement, some multi-leaf collimators may optionally comprise reduced-weight leaves where only the material in the radiation beam path have high-Z materials, and the peripheral support structure(s) of the leaves comprises lighter-weight materials. Also disclosed herein are leaf arrangements that may help reduce the friction between leaves, as well as ways to package and arrange the various leaf drive mechanisms so that the collimator is suitable for mounting on a rotatable gantry.

Also disclosed herein is a collimator that may comprise a leaf movable between a first location and a second location, a leaf shaft having a proximal portion and a distal portion that is attached to the leaf, a spring system coupled to the leaf shaft and configured to apply forces along a longitudinal axis of the leaf shaft, and an actuator system coupled to the leaf shaft. The forces applied by the spring system and the actuator system on the leaf shaft may longitudinally translate the leaf shaft to move the leaf between the first and second locations, and the actuator system may be configured to selectively retain the leaf at the first location or the second location. The actuator system may be configured to supply a motive force sufficient to overcome losses in the spring system. The actuator system may comprise a first configuration where the leaf is retained in the first location and a second configuration where the leaf is retained in the second location. The spring system may comprise at least one coil spring or torsion bar spring. When the actuator system is in the first configuration, the leaf may be in a closed configuration and when the actuator system is in the second configuration, the leaf may be in an open configuration, and the spring system and actuator system may be configured to transition the leaf between the closed configuration and open configuration in about 6 ms or less.

In some variations, the actuator system may comprise a barrel comprising a longitudinal lumen, a first side opening, and a second side opening, and a piston extends within the longitudinal lumen of the barrel. The piston may comprise the shaft and a piston seal coupled to the shaft within the barrel. Movement of the piston within the barrel may translate the leaf between the first location and the second location. The spring system may comprise a first spring disposed along a first length of the shaft on a first side of the piston seal, and a second spring disposed along a second length of the shaft on a second side of the piston seal that is opposite the first side. The first and second springs may be configured such that the piston seal moves between the first opening and the second opening. In some variations, the first spring and the second spring may be located within the barrel lumen and optionally, the first spring may be in contact with the piston seal on the first side and the second spring may be in contact with the piston seal on the second side. In another variation, the first spring may be located outside of the barrel lumen between a spring retainer and a first end wall of the barrel and the second spring may be located outside of the barrel lumen between a second end wall of the barrel and the leaf. A collimator may also comprise a fluid source connected to the first opening and the second opening, where the movement of the piston is controlled by fluid flow into and/or out of the first and second openings. For example, an actuator system may further comprise a first valve between the first opening and the fluid source and a second valve between the second opening and the fluid source, where the first and second valves selectively regulate fluid flow into and out of the barrel lumen. The fluid source may be a pressurized air source. The actuator system may be configured such that injecting fluid from the fluid source to the second opening and not the first opening causes the piston to move the leaf to the second location. Sufficient amounts of fluid injected into the second opening may create sufficient pressure to hold the leaf in the second location. The piston seal may be configured to contact the first spring and not the second spring when the leaf is in the first location and to contact the second spring and not the first spring when the leaf is in the second location. Some variations may comprise a controller in communication with the fluid source, the first valve and the second valve. The controller may be configured to open and close the first valve and the second valve to selectively regulate fluid flow into and out of the barrel lumen. The controller may be configured to move the leaf to the first location by opening the first valve and closing the second valve. Optionally, the controller may be configured to open the second valve to vent the fluid (e.g., to atmospheric pressure) prior to opening the first valve and then closing the second valve after the leaf has been moved to the first location. The controller may also be configured to move the leaf to the second location by opening the second valve and closing the first valve. In some variations, the controller may be configured to open the first valve to vent the fluid (e.g., to atmospheric pressure) prior to opening the second valve and then closing the first valve after the leaf has been moved to the second location.

In another variation of a collimator comprising a leaf, a leaf shaft, a spring system and an actuator system, the proximal portion of the leaf shaft may comprise a slot and the actuator system may comprise a motor, a rod, a crank rotatably connected to the rod, and a roller connected to the crank. The roller may rotatably translate within the slot, and the rotation of the roller may be controlled at least in part by the motor via the rod and crank and at least in part by spring forces applied by the spring system on the leaf shaft. The crank may have a longitudinal axis and the arm may have a longitudinal axis, and when the longitudinal axis of the crank is aligned with the longitudinal axis of the leaf shaft, the leaf may be retained at either the first location or the second location. The slot may have a vertical dimension and a horizontal dimension, where the vertical dimension may be greater than the horizontal dimension. For example, the slot may be shaped as an oval or ellipse, and/or may have two parallel vertical sides. The slot may have an oval-like shape that has a plurality of curves and/or lobes having different radii of curvature. In some variations, the slot may have a first curved region, a second curved region and a third curved region. The first, second and third curved regions may be contiguous with each other. When the roller is located in the first curved region, spring forces from the spring system may cause the leaf to move between the first location and the second location. When the roller is located in the second curved region, rotation of the roller within the slot may not cause translation of the leaf shaft and the leaf may be retained in either the first location or the second location. When the roller is located in the third curved region, rotation of the roller further into the region may compress the spring at a nonlinear rate. In some variations, the slot may be bilaterally symmetric about a vertical axis such that there is a first side and a second side symmetric to the first side, and the first, second and third curved regions may be located on the first side and fourth, fifth, and sixth curved regions that correspond to the first, second and third curved regions may be located on the second side. When the roller is located in the second or third curved regions of the first side of the slot, the leaf may be retained in an open position and when the roller is located in the fifth or sixth regions of the second side of the slot, the leaf may be retained in a closed position. The spring system may comprise a torsion bar spring, and the torsion bar spring may optionally be connected to the leaf shaft by a pivotable coupling arm such that rotational torsion of the bar spring causes the leaf shaft to translate longitudinally. A first end of the pivotable coupling arm may be connected to the torsion bar spring via a pin and a second end of the pivotable coupling arm may be connected to the arm via a second ball bearing. Alternatively, the spring system may comprise one or more coil springs. For example, the spring mechanism may comprise a first coil spring and a second coil spring, where the first coil spring is biased such that it applies a force to the leaf shaft such that the leaf moves toward the first location and the second coil spring is biased such that it applies a forces to the leaf shaft such that the leaf moves toward the second location. The actuator system may be located at a central portion of the leaf shaft, and the first coil spring may be wrapped around a first length of the leaf shaft proximal to the actuator system and the second coil spring may be wrapped round a second length of the arm distal to the actuator mechanism.

Some variations of an actuator system that may be used in a collimator may comprise a first electromagnet and a second electromagnet separated by a space from the first electromagnet, and a ferromagnetic member movable across the space between the first and second electromagnets. The leaf shaft may be connected to the movable member, and the actuator system may further comprise a first configuration where either the first or second electromagnet is activated such that the movable member is secured at the location of either the first or second electromagnet, and a second configuration where the first and second electromagnets are alternately activated such that the movable member is movable within the space. Each of the first and second electromagnets may comprise a pair of adjacent coil windings and a U-shaped core extending through the lumens of both of the coil windings. In some variations, the movable member may comprise a permanent magnet. Alternatively or additionally, the actuator system may comprise a linear actuator, such as a voice coil.

One variation of a multi-leaf collimator may comprise a leaf translatable between an open position and a closed position, a cam assembly, and a latch that selectively engages the cam assembly with the leaf. The latch may have a locked configuration where the cam assembly is engaged with the leaf such that movement of the cam assembly causes movement of the leaf, and an unlocked configuration where the cam assembly is disengaged from the leaf such that movement of the cam assembly does not cause movement of the leaf. In the closed position, the leaf may be located in a radiation path of a radiation source, and in the open position, the leaf may not be in the radiation path of the radiation source. The cam assembly may comprise a cam and a follower, and when in the locked configuration, rotating the cam may transition the leaf between the closed position and the open position. In some variations, a shaft may be attached to the leaf, and the latch may selectively engage the follower with the shaft such that in the locked configuration, the follower and the shaft are mechanically engaged, and in the unlocked configuration, the follower and the shaft are mechanically disengaged. The latch may be coaxial with the shaft. In some variations, the latch may comprise an outer housing attached to the follower and an inner cylindrical member rotatably mounted within the outer housing, and the inner member may be rotatably engaged with the shaft. The outer surface of the inner member may comprise a first set of splines and the inner surface of the outer housing may comprise a second set of splines that may be aligned with the first set of splines when the latch is in the locked configuration. The first set of splines and the second set of splines may be radially arranged.

Some variations of a multi-leaf collimator may also comprise a rotary actuator configured to transition the latch between the unlocked configuration and the locked configuration. The rotary actuator may comprise an actuator shaft that may be coaxial with the latch and coupled to the latch via a connector, and rotation of the actuator shaft may transition the latch between the locked configuration and the unlocked configuration. The connector may be attached to the inner cylindrical member and the outer surface of the connector may comprise a third set of splines, and the inner surface of the outer housing may comprise a fourth set of splines configured to interlock with the third set of splines to select a relative rotational position of the connector with respect to the latch. In some variations, the third set of splines and the fourth set of splines may be radially arranged such that they are radially interlocked. Optionally, a spring assembly may be coupled to the actuator shaft, where the spring assembly may be configured to transition the latch between the locked and unlocked configurations faster than the rotational speed of the rotary actuator. The spring assembly may comprise one or more torsion springs. In some variations, a linear actuator may be included and configured to transition the latch between the unlocked configuration and the locked configuration. Some variations may also comprise a spring configured to bias the leaf to the closed configuration. The cam may have two or three lobes, as may be desirable. Optionally, a multi-leaf collimator may comprise a second latch mechanism configured such that the leaf is in the open configuration independent of the cam position.

Another variation of a system for selectively moving a leaf between a first position and a second position may comprise an arm carrying the leaf, a rotating cam, a cam follower engaged with the cam, and a latch for selectively coupling the motion of the cam follower to the arm, such that when the latch is locked, the cam follower causes the arm to move the leaf from the first position to the second position. The system may further include a spring arranged to move the leaf from the second position back to the first position. In some variations, the latch may include a cylindrical outer member having a set of radially disposed, internally projecting splines and a cylindrical inner member having a set of radially disposed, externally projecting second splines. When the latch is in an unlocked position the first and second splines may be radially offset allowing the first splines to slidably telescope with respect to the second splines and when the latch is in a locked position, the end faces of the first splines may abut the end faces of the second splines causing the arm to move the leaf from the first position to the second position.

Another variation of a system for selectively moving a leaf between a first and a second position may comprise a spring system for supplying the force to move the leaf between a first and a second position, and an actuator system for latching or holding the leaf in a selected position and for supplying a motive force sufficient to overcome losses in the spring system. The spring system may include one or more springs where the zero-force position of the one or more springs corresponds to a location when the leaf is between the first and second positions. The spring system and actuator system may be arranged to reciprocate the leaf between the first and second positions and the actuator system may be employed to prevent the leaf from moving from the first to the second position or from the second position to the first position. In some variations, the actuator system may not be used to hold the leaf when it reaches one position when it is desired to immediately thereafter move the leaf to the other position. The spring system may be designed to move the leaf beyond the first and second positions so that that the leaf will be located in the open and closed positions for a predetermined dwell time.

Another variation of a system for selectively moving a leaf between an open and a closed position may comprise a spring system for reciprocating the leaf between a first and second positions, an actuator system comprising a secondary drive mechanism coupled to the leaf to supply motive force sufficient to overcome losses in the spring system, and a phase shifting mechanism for adjusting the movement of the leaf to change the timing of the arrival of the leaf to the first and second positions.

BRIEF DESCRIPTION OF THE DRAWINGS

FIGS. 3C and 3D are perspective exploded component views of the latch mechanism of FIG. 3B.

FIGS. 9A-9D depict timing diagrams of one variation of a phase-shifted spring-based leaf drive mechanism.

FIGS. 10B-10F depict different states of one variation of a pneumatic leaf drive mechanism.

FIGS. 11A-11F depict one variation of a leaf actuation system comprising a slotted-link or scotch yoke mechanism. FIGS. 11B, 11D, 11F are close-up depictions of the different configurations of the scotch yoke mechanism as the leaf moves between a closed and an open configuration.

FIGS. 15E-15G depict a flowchart representation of a method for assembling a plurality of leaf drive mechanisms that comprise a spring system and an actuator system including a scotch yoke.

DETAILED DESCRIPTION

Disclosed herein are various drive mechanisms that may be suitable for use in a multi-leaf collimator. Such leaf drive mechanisms may facilitate the rapid and reliable movement of collimator leaves such that the collimator is capable of transitioning leaves between open and closed positions in about 10 ms or less, e.g., about 4 ms or less. Various leaf drive mechanisms are described below, including cam-based drive mechanisms, spring-based drive mechanisms, fluid-power drive mechanisms, and/or electromagnetic drive mechanisms. In addition to increasing the speed of leaf movement by increasing the speed of the leaf drive mechanisms, some multi-leaf collimators may optionally comprise reduced-weight leaves where only the material in the radiation beam path have high-Z materials (e.g., tungsten), and the peripheral support structure(s) of the leaves comprises lighter-weight materials. Also disclosed herein are leaf arrangements that may help reduce the friction between leaves, as well as ways to package and arrange the various leaf drive mechanisms so that the collimator is suitable for mounting on a rotatable gantry.

While the leaf drive mechanisms disclosed herein are described in the context of a binary multi-leaf collimator for collimating a radiation beam, it should be understood that these drive mechanisms may be used in other types of collimators and furthermore, are not limited to collimator technology. Any of the leaf drive mechanisms described herein may be used in collimators for conformal radiation therapy, emission guided radiation therapy (EGRT), and intensity modulated radiation therapy (IMRT). Certain of these leaf drive mechanisms may be suitable for use in other mechanical systems. The speeds and rates of operation of any of the drive mechanisms described herein may also vary from the speeds and rates described in the examples. For example, while the leaf drive mechanisms are described as being capable of transitioning leaves (for example, leaves having a radiation-attenuating portion have a length of about 10 cm, width of about 1 cm, and a thickness of about 3 mm thick) between open and closed states in about 10 milliseconds or less, the leaf transition time may be from about 2 milliseconds to about 10 seconds.

Figure 1:
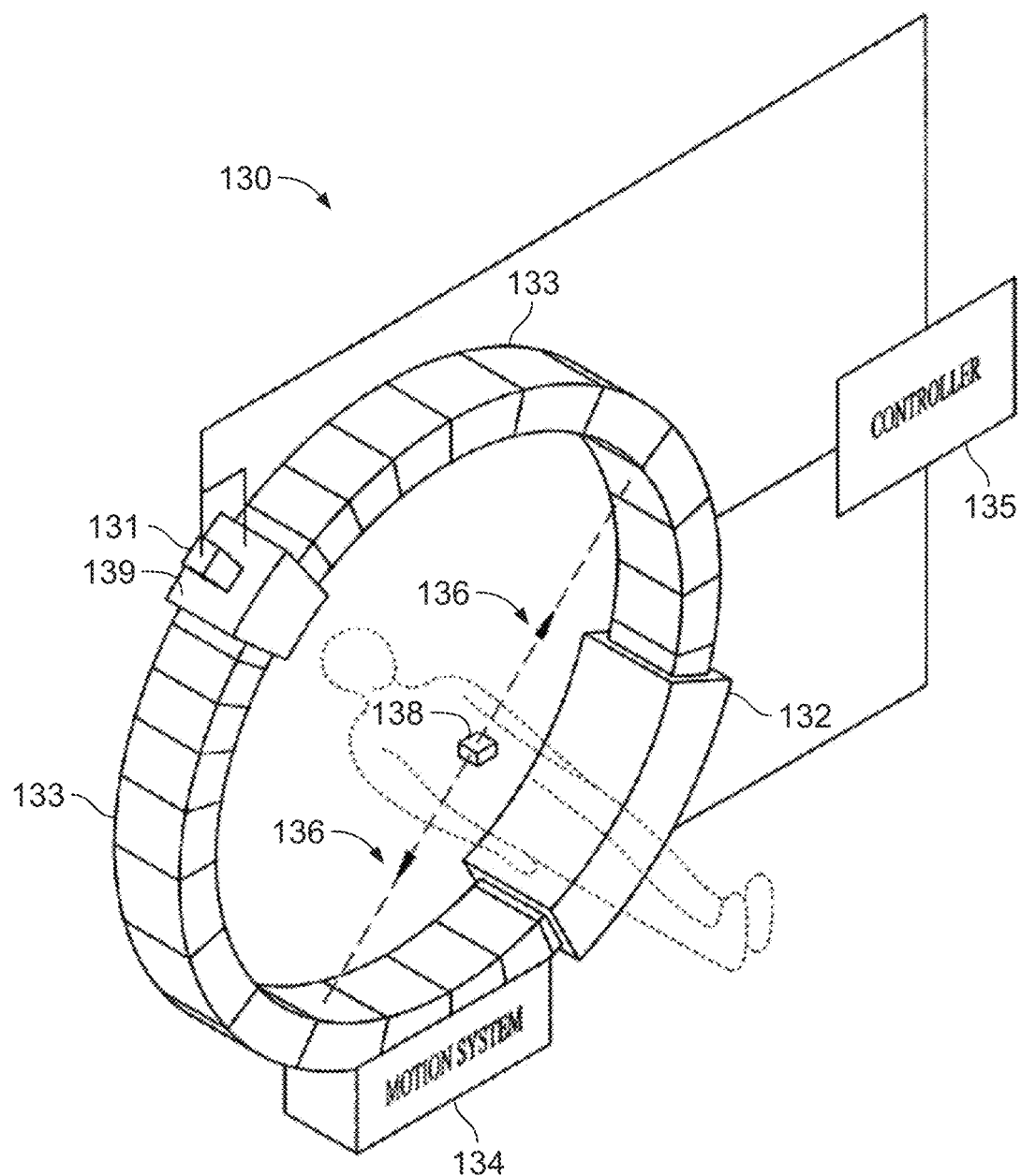
FIG. 1 is a schematic depiction of one variation of an emission guided radiation therapy system.

One variation of a system that may comprise any of the multi-leaf collimators as described herein is depicted in FIG. 1. The radiation therapy system may comprise a plurality of gamma ray photon emission detectors (e.g., positron emission detectors) located on a first gantry. The gantry may be stationary or may be rotatable. The radiation therapy system may also comprise a rotatable radiation source (e.g., a linear accelerator or linac). The rotatable radiation source may be located on the same gantry as the gamma ray photon emission detectors, or may be located on a different gantry (i.e., a second gantry) that may be rotated independently from the first gantry. There may also be an X-ray detector located on the second gantry across from the radiation source. Before a treatment session, a patient may be injected with a radioactive tracer. In some variations, the tracer may be a PET tracer such as fluorodeoxyglucose (FDG) that accumulates at a tumor site. Gamma ray photons (e.g., a pair of photons emitted from a positron annihilation event) may be emitted from the tumor site and detected by the gamma ray photon detectors. When the photons are detected, the radiation source may be rotated and positioned such that a radiation beam may be directed toward the tumor site with respect to the gamma ray photon emission path. A multi-leaf collimator, such as any of the collimators described herein, may be disposed in the beam path and used to further shape the beam and/or select the beamlet. In some variations, by positioning the radiation source and opening and closing selected leaves of the collimator, the radiation beam may be directed approximately along the detected photon emission path. The radiation beam may be applied within a short period of time after the gamma ray photons are detected, for example, within 0.25 seconds of detecting the photons. This may help to compensate for motion artifacts that may arise from breathing and/or inadvertent patient movement. In some variations, the radiation beam may be applied before the tumor moves substantially, and/or before an image based on the gamma ray photon emission path is formed. Directing a radiation beam with respect to a detected gamma ray photon emission path without generating an image based on that detected photon may help to increase the likelihood that radiation is applied to the tumor site before it moves substantially. This in turn may help to reduce the radiation exposure of peripheral healthy tissue (e.g., tissue close to the tumor boundary), as well as to reduce the length of the treatment session. Additional description of a radiation therapy system is provided in U.S. Pat. No. 8,017,915, filed Feb. 9, 2009, which is hereby incorporated by reference in its entirety. Any of the collimators described herein may be included in a radiation therapy system (e.g., an emission guided radiation therapy system) to facilitate dynamic, real-time selection of radiation beamlets and/or direction of radiation to a tumor site. For example, the positions of the collimator leaves may be adjusted while the radiation source and collimator are rotating. The collimator may be disposed in the beam path or fan beam of the radiation source and may, in some variations, be located within the same housing or module as the radiation source. Alternatively, a collimator may be disposed external to the radiation source housing or module.

One way to direct radiation to a tumor site before it moves, and/or to apply radiation to a tumor site within a short period of time (e.g., less than about 2 seconds, about 1 second, about 0.5 second, or about 0.25 second) after detecting the photon emissions may comprise rotating the radiation source at speeds greater than current radiation therapy gantries. For example, current gantries rotate at about 1 rpm, while an EGRT gantry on which the radiation source is mounted may rotate between about 10 rpm to about 70 rpm (e.g., about 30 rpm, about 60 rpm), and in some variations, faster than 70 rpm. In addition to increasing the rotation speed of the gantry, the associated collimator mounted on the gantry may also operate at a higher frequency than current collimators. For example, the collimator may operate at a speed such that the collimator leaves may transition from an open position (i.e., permitting the passage of a radiation beamlet) to a closed configuration (i.e., blocking the passage of a radiation beamlet) in about 10 ms or less (e.g., about 4 ms or less). As an illustration, a radiation therapy system having 100 locations around the gantry from which the radiation source may fire a beam (i.e., 100 firing locations) may have a radiation source gantry that is configured to rotate at a speed of 60 rpm. In this variation, the collimator leaves of the radiation source may be configured to open or close in about 10 ms or less. In a system with more firing locations, for example 250 firing locations where the gantry rotates at 60 rpm, the collimator leaves of the radiation source may be configured to open or close within about 4 ms or less. If the rotation source gantry (note that there may be any number of radiation firing positions around the radiation source gantry, for example, about 60 firing positions, 120 firing positions, 250 firing positions, etc.) were to rotate faster than 60 rpm, e.g., 70 rpm or 75 rpm, the collimator leaves may be configured to open or close in even shorter periods of time, e.g., less than 4 ms, about 3 ms, about 2 ms, about 1 ms or less. In some variations, the bandwidth or the maximum frequency of operation of a collimator may be about 50 Hz, or even greater than about 50 Hz. That is, the inverse of the shortest time period it takes for a leaf to transition from a closed position to the open position and then back to the closed position, or from an open position to the closed position and then back to the open position may be about 50 Hz or more. For example, for a radiation source gantry that rotates at 75 rpm, a collimator leaf may be configured to transition between open and closed positions within about 8 ms (about 62.5 Hz) for 100 firing locations and within about 3.2 ms (about 156.25 Hz) for 250 firing locations. In some variations, a leaf may be moved at a speed from about 50 cm/s to about 400 cm/s. The collimator leaf drive mechanisms described herein may be suitable for operating at such high speeds and frequencies for real-time irradiation of a tumor, and may, for example, be compactly packaged for mounting on a rotating gantry.

Optionally, the collimator leaves described herein may comprise a radiation-attenuation structure and optionally a support structure attached to the radiation-attenuation structure. When the leaf is in the closed position, the radiation-attenuation structure is located in the radiation beam path. The radiation-attenuation portion may be made of a high-Z material (e.g., a high atomic numbered material). Optionally, a collimator leaf may additionally comprise a support structure that couples the radiation-attenuation structure with a leaf drive mechanism and/or other components in the collimator. The support structure may comprise a frame of beams, bars, rods, and/or brackets that may help to vertically stabilize the leaf as it moves in a horizontal direction into and out of the beam path, and may optionally contain leaf guides and/or push rods. In some variations, the support structure may comprise a truss framework. The support structure may optionally include openings, hooks, notches, protrusions, grooves, and the like so that a leaf drive mechanism may be attached to the collimator leaf. A support structure may also comprise notches, protrusions, grooves, ridges, etc. that correspond with similar structures in a leaf guide, which may help the leaf move along a path. The size and shape of the leaves of a multi-leaf collimator for radiation therapy may be at least partially determined by the geometry of the gantry and/or the width of the radiation beam and/or the desired "resolution" at which radiation is to be applied (e.g., slice width, number of slices). The depth of the leaves may be sufficiently thick to impede the transmission of radiation when the leaves are in the closed position. For example, a leaf made of a high-Z material such as tungsten may be about 10 cm deep or more. The collimators described herein may have 64 leaves, but it should be understood that the number of leaves may be varied, e.g., 12, 15, 16, 24, 25, 31, 32, 36, 48, 50, 64, 72, 75, 100, 101, 128, 135, etc. The width of the individual leaves of a 64-leaf collimator may be from about 1 mm to about 10 mm, e.g., about 2 mm. The length of leaf travel (e.g., the slice size) may be from about 0.25 cm to about 3 cm, e.g., about 1 cm. The smaller the travel range, the more precisely the radiation may be delivered. Reducing leaf travel length or width may prolong patient treatment time. The mass of the radiation-attenuation portion of a leaf may be from about 2.5 grams to about 100 grams, e.g., about 30 grams. The support structure of a leaf may have a mass from about 10 grams to about 100 grams, e.g., about 20 grams. As such, the total mass of a collimator leaf may be from about 13 grams to about 200 grams, e.g., about 50 grams. Moving leaves of this mass at the bandwidths described above may be challenging for current collimators, but may be attained by the high-bandwidth collimators described herein.

Disclosed herein are various leaf drive mechanisms that may be used in a high-bandwidth collimator. The described leaf drive mechanisms may be capable of moving individual collimator leaves at a speed from about 50 cm/s to about 400 cm/s. In a binary multi-leaf collimator, these drive mechanisms may translate the leaf between a closed position, where the leaf is located in the path of a radiation beam, and an open position, where the leaf is not located in the path of the radiation beam. In some variations, a collimator may comprise a leaf drive mechanism that comprises a cam and follower to translate the leaf between an open position and a closed position. Another variation of a leaf drive mechanism may comprise one or more springs that apply force(s) on the leaf to transition between an open position and a closed position. For example, a leaf may be coupled to a spring resonator that translates the leaf between an open position and a closed position. In another variation, a leaf drive mechanism may comprise fluid-power components, for example, a hydraulic or pneumatic driven piston in a cylinder. The piston and cylinder may have corresponding non-circular cross-sections. The cylinder may have one or more valves that may be independently controlled to regulate the flow and/or pressure of fluid therein. Alternatively or additionally, any of the collimator leaf drive mechanisms described herein may comprise one or more springs to move the leaf to a closed position or open position. These drive mechanisms may be configured to move each leaf of a multi-collimator individually and/or independently, or may be configured to move two or more leaves together.

Optionally, the leaves and their corresponding drive mechanisms may be arranged such that two leaves may be adjacent to each other, but offset in the vertical direction (e.g., in the direction of the radiation beam). This allows the width of the actuators driving the leaves to be wider than the leaves, while still allowing the actuators to drive the leaves along their center of mass. A multi-leaf collimator may also comprise a plurality of leaf guides that correspond with each of the leaves to limit the movement of the leaves along a linear path that crosses (e.g., is transverse to) the beam path.

In addition or alternatively to increasing the speed of the leaf transitions by using faster drive mechanisms, some variations of multi-leaf collimators may comprise leaves where only the portion of the leaf that is in the radiation path when the leaf is in the closed position is made of a radiation-impermeable material, while the remaining portion of the leaf may be made of other materials, e.g., materials that are less dense and/or lighter than the radiation-impermeable materials. For example, the portion of the leaf that is in the radiation path when the leaf is in the closed position may be made of tungsten, while the remainder of the leaf, including the support/frame to which the leaf is attached is made of much lighter materials, such as stainless steel or titanium. In some variations, removing or hollowing out regions of the radiation-impermeable material may help to reduce the weight of the radiation-impermeable portion with little or no impact to the ability of the leaf to impede radiation transmission. For example, the portion of the radiation-impermeable portion of the leaf that is in the radiation path may be substantially solid, while the portion of the radiation-impermeable portion of the leaf that is not in the radiation path may have one or more hollow regions.

Optionally, a multi-leaf collimator may comprise one or more position, velocity, acceleration or force sensors configured to detect the position, velocity, acceleration or force of each of the leaves, and to provide such data to a controller. It may be useful to select a sensor that is capable of providing precise data in high-radiation environments, such as a capacitance-based position sensor. Other examples of sensors that may be used in any of the multi-leaf collimators and/or drive mechanisms described herein may include an opto-electronic interrupter. The data from the one or more sensors may be included in a feedback control algorithm stored and executed in the controller to monitor and/or regulate the precision and speed of the leaf movement. The feedback control algorithm may also factor in the rotation of the gantry and the radial location of the radiation source and collimator when providing the commands to the leaf actuators.

Figure 2:
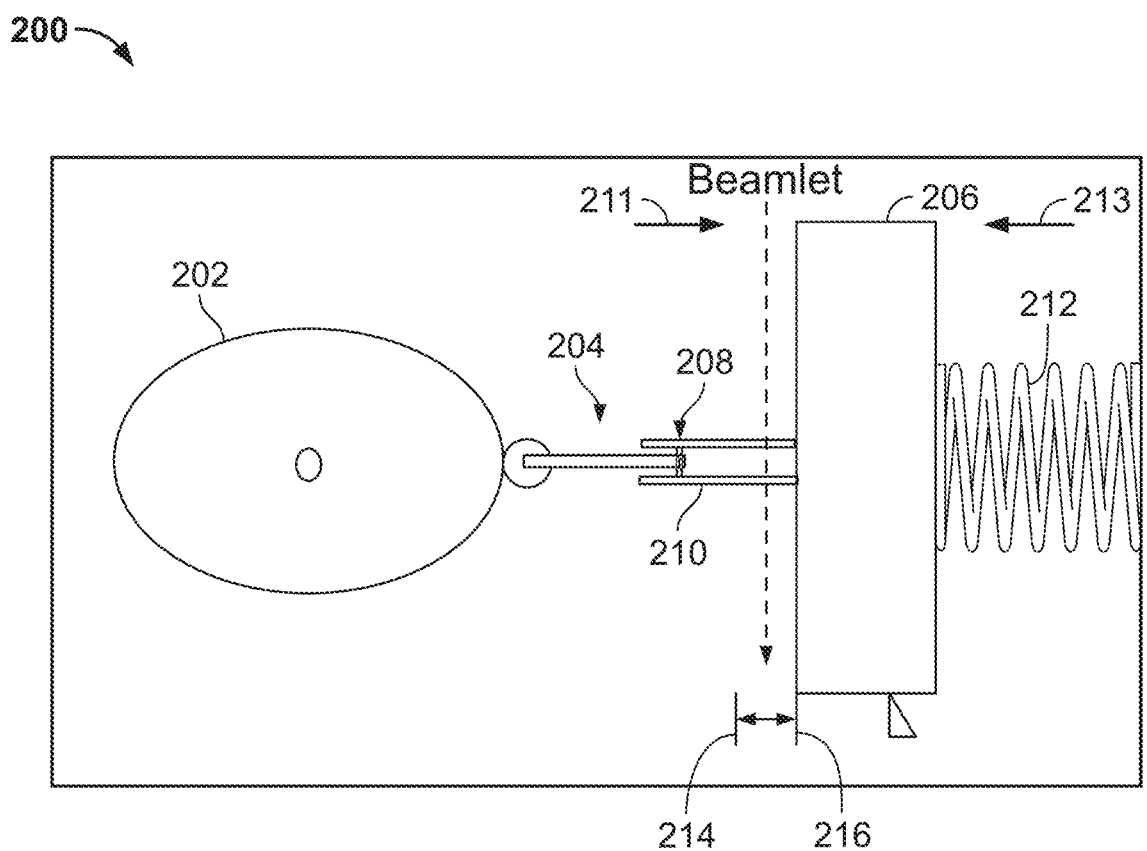
FIG. 2 is a schematic depiction of one variation of a cam-based leaf drive mechanism that may be used in a collimator.

FIG. 2 is a schematic depiction of a cam-based leaf drive mechanism 200 that may be included in a collimator disposed in the beam path of a radiation source (e.g., for a radiation therapy system). The cam-based leaf drive mechanism 200 may comprise a cam 202, a follower 204, a pushrod or shaft 210 attached to a side of a leaf 206, a clutch 208 that selectively engages or disengages the follower and the shaft, and a spring 212 attached to the opposite side of the leaf 206. The cam 202 may be a constant rotation cam (e.g., the cam is continuously rotated) that drives a follower. The follower 204 may be coupled to the leaf 206, where the clutch or latch 208 determines whether the leaf 206 moves in concert with the follower 204. As depicted in FIG. 2, the follower may be coupled to the leaf 206 via a shaft or pushrod 210. The shaft or pushrod 210 may be made of a low-Z material that does not interfere with the radiation beam from the radiation source. An actuator (e.g. a piezo actuator; not shown) may be coupled to the clutch 208 and used to control whether the clutch is 208 engaged or disengaged. When the clutch 208 is disengaged, the position of the leaf is controlled by the spring 212, which pushes on the leaf in the direction of arrow 213 and biases the leaf to a closed position 214. The leaf can be held in the closed position 214 because the cam follower 204 slides inside the shaft 210, and does not apply a force on the leaf (e.g., not moving the leaf). When the clutch 208 is engaged, the cam follower 204 becomes rigidly attached to the shaft 210 and rotation of the cam 202 moves the leaf against the force of the spring 212 in the direction of arrow 211, thereby compressing the spring 212 and moving the leaf to an open position 216. Due to the constantly rotating cam 202, however, the leaf cannot remain in an open position 216 when the clutch 208 is engaged, since rotating the cam 202 will cause the leaf to open, then close and then open again as the cam 202 rotates. The duration of time that the leaf spends in the open position 216 may be adjusted, for example, by adjusting the arc of the cam lobe to adjust the dwell time (e.g., increasing the arc of the lobe may increase the dwell time).

Figure 3A:
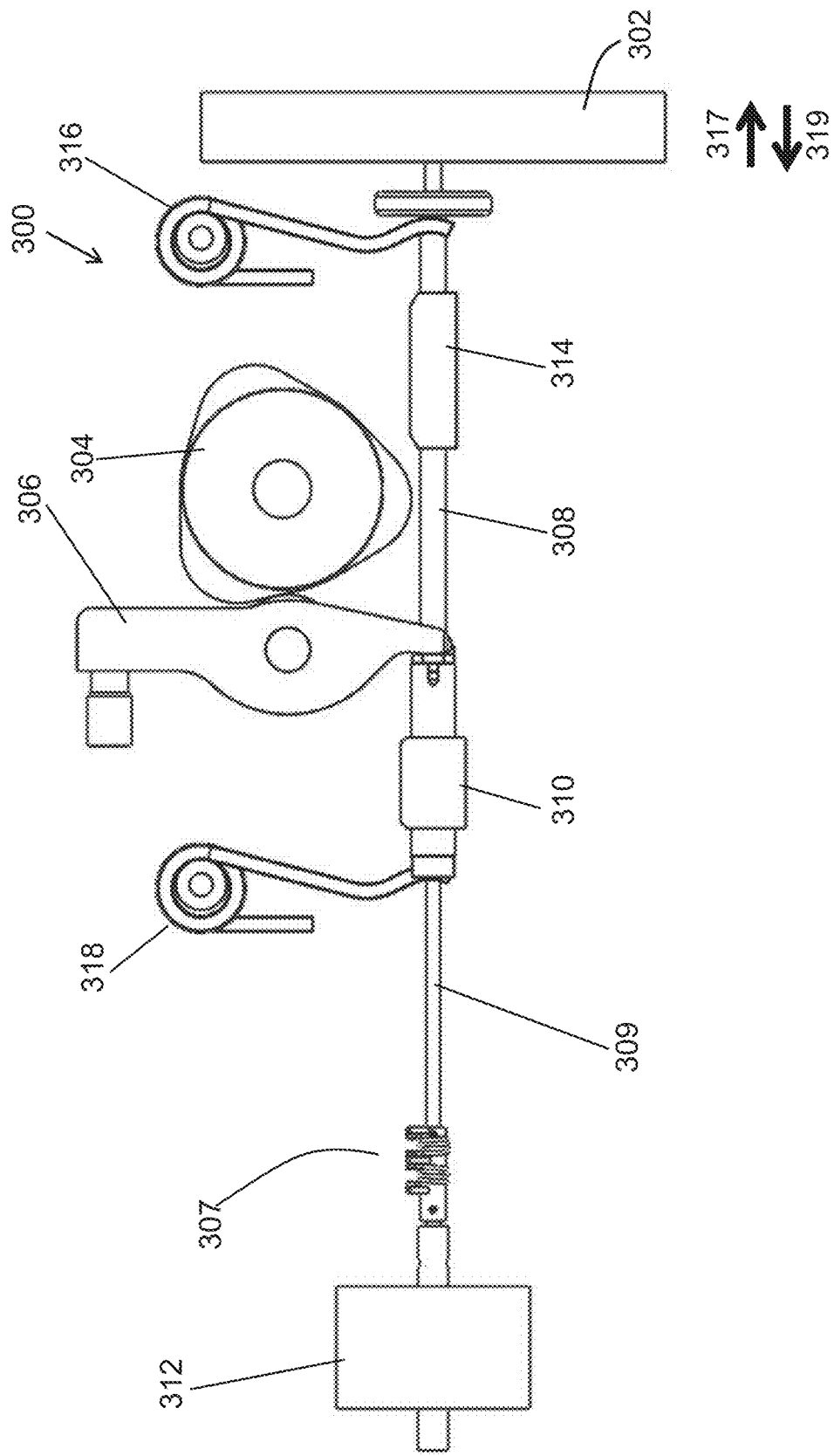
FIG. 3A is a perspective view of one variation of a cam-based leaf drive mechanism that may be used in a collimator.

One variation of a cam-based leaf drive mechanism for a multi-leaf collimator that may be included in a radiation therapy system is depicted in FIGS. 3A-3K. FIG. 3A depicts a cam-based drive mechanism 300 comprising a leaf 302, a shaft 308 connected to the leaf, a cam 304, a follower 306 that is in contact with the cam and selectively engaged to the shaft 308, a latch 310 configured to selectively engage the follower and the shaft, and a solenoid or rotary actuator 312 coupled to the latch 310 and configured to control whether the latch engages the follower with the shaft or disengages the shaft from the follower. In some variations, the cam-based drive mechanism may also comprise a torsion spring assembly 307 that may be arranged to couple the rotary actuator 312 to an actuator shaft 309 to facilitate and/or expedite transitioning the latch 310 between a first locked configuration (where the leaf shaft 308 and the follower 306 are engaged and locked together such that movement of the follower causes a corresponding movement in the shaft) and a second unlocked configuration (where the leaf shaft 308 and the follower 306 are disengaged and unlocked from each other such that movement of the follower does not cause a corresponding movement in the shaft). Optionally, the cam-based leaf drive mechanism 300 may comprise a shaft guide 314 disposed over the shaft 308 and configured to stabilize the leaf shaft 308 such that the shaft is translated in a linear path. The leaf drive mechanism 300 may optionally comprise distal-most springs 316 that may apply a spring force on the leaf 302 in the direction of arrow 317. Moving the leaf 302 in the direction of arrow 317 moves the leaf into the closed position (i.e., into the radiation beam path). When the cam cycles to a lift event (i.e., where a lobe of the cam contacts the follower) and the follower is engaged with the leaf shaft 308, the leaf 302 may be moved to an open position (i.e., away from, and/or out of, the radiation beam path), which is in the direction denoted by arrow 319. The cam may have one, two, three or more lobes, as may be desirable. The cam may be configured to be continuously rotated, for example, by a rotary actuator (not shown). By constantly rotating the cam and only switching the latch to selectively engage the leaf when the follower is in the base-circle region of the cam, the high bandwidth element (the latch) and the high force element (the cam) are actuated separately. This separation means the high bandwidth element can operate on a smaller mass and smaller distance instead of having to act very quickly on a larger mass. In some variations, a cam may have three lobes and may rotate at 2000 rpm such that there are 100 lift events per second (i.e., 100 Hz). The latch may be capable of transitioning between the engaged and disengaged states in about 1 ms or less. In other variations, the cam may rotate at less than 2000 rpm, and may rotate at 1000 rpm, 100 rpm or 10 rpm. One or more lubricants may be provided between the moving parts of this (and other) leaf drive mechanisms to facilitate the movement of the different components and to reduce the effects of frictional forces. In some variations, the lubricant may be resistant to depletion by radiation (e.g., a radiation-hard lubricant). Optionally, the leaf drive mechanisms may be enclosed in a sealed housing so that the lubricant within the box does not leak out.

The location of the leaf 302 may be determined by the sum of the push-pull forces exerted upon the leaf 302 and/or the leaf shaft 308 by the distal-most springs 316 and the cam 304. The distal-most springs 316 may apply a pushing force on the leaf (i.e., in a direction indicated by arrow 317 in FIG. 3A), which may bias the leaf into the closed configuration. The cam 304 and follower 306 may apply a pulling force on the leaf (i.e., in a direction indicated by arrow 319) when the latch 310 engages or locks the follower 306 with the leaf shaft 308 and a lobe of the cam is in contact with the follower (i.e., a lift event). The pulling force in the direction of arrow 319 may be greater than the push force of the distal-most springs in the direction of arrow 317, resulting in a net pulling force that translates the leaf into the open position (i.e., net movement in the direction of arrow 319). As the cam rotates and the follower is no longer riding on a lobe of the cam, the pulling force is reduced and the pushing force of the distal-most springs dominates, thereby translating the leaf to the closed position (i.e., net movement in the direction of arrow 317). When the latch 310 is switched such that the follower 306 is disengaged or unlocked from the leaf shaft 308, the movement and position of the leaf is not controlled by the cam 304, but is instead biased by the distal-most springs 316 into the closed position. Continued rotation of the cam may continue to drive the follower 316, the motion of which applies a force against the proximal springs 318 (a.k.a. lost-motion springs). However, once the latch 310 is switched such that the follower 306 is engaged or locked with the leaf shaft 308, the leaf 302 may be translated between the open and closed positions in accordance with the rotation of the cam and movement of the follower.

Figure 3B:
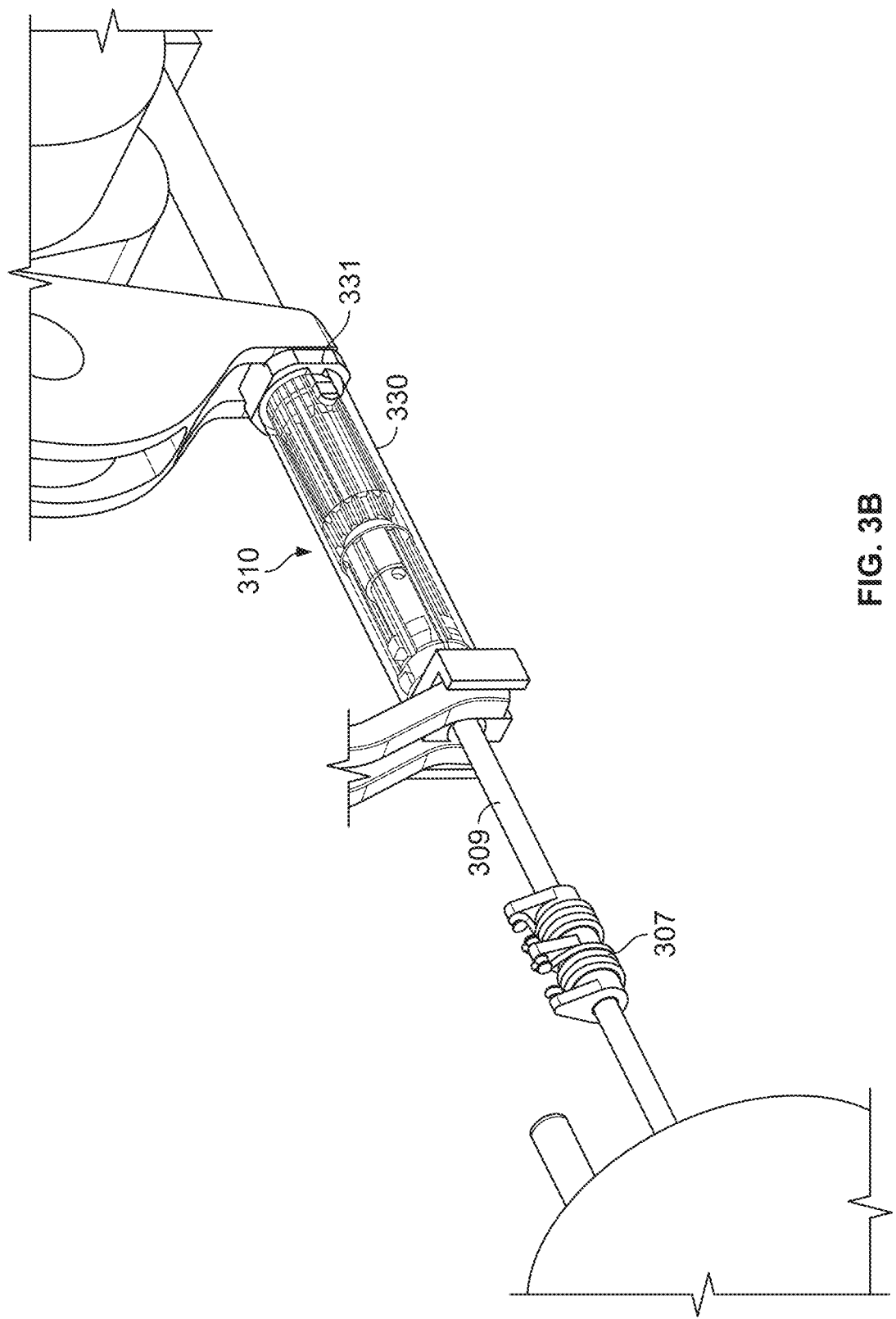
FIG. 3B is a perspective and partial cutaway view of a latch mechanism of the cam-based leaf drive mechanism of FIG. 3A.

Different types of latches may be used to selectively engage the follower with the shaft. One variation of a latch mechanism is depicted in FIGS. 3B-3I. As depicted in FIGS. 3B-3F, the latch mechanism 310 may comprise an elongate tube 330 having a lumen 332 therethrough and one or more protrusions or splines 334 along the interior wall of the lumen, an inner ring 336 with one or more protrusions or splines 338 on its outer surface that correspond to the protrusions 334 of the tube lumen 332, where the inner ring 336 is rotatable with respect to the elongate tube 330, an actuator shaft 309 connected to the inner ring 336, and a rotary motor 312 that is arranged to rotate the actuator shaft 309 such that the inner ring 336 rotates within the elongate tube. A partial cutaway view of the elongate tube 330 and an end view of the elongate tube are depicted in FIGS. 3F-3G, and a perspective view of the inner ring 336 is depicted in FIG. 3D. As depicted in FIG. 3G, the protrusions 334 along the inner surface of the elongate tube lumen 332 may be radially arranged and the protrusions 338 of the inner ring 336 may be radially arranged in corresponding fashion. The edges of the protrusions may be curved or rounded, which may help to ease the stresses on the protrusions as the inner ring rotates with respect to the elongate tube. Optionally, a lubricant may be provided between the components of the latch, such as between the protrusions of the inner ring and the elongate tube. There may be any number of protrusions 334 on the inner surface of the elongate tube lumen 332 and the outer surface of the inner ring 336, for example, 2, 3, 4, 5, 6, 8, 10, 12, 14, 20, etc. The variations depicted in FIGS. 3D and 3F have 12 protrusions. The inner ring 336 may be rotatably connected to the leaf shaft 308 which drives the leaf 302 between the open and closed positions. One example of the connectivity between the inner ring 336, leaf shaft 308, and latch mechanism 310 is depicted in FIGS. 3C, 3D, and 3I. The elongate tube 330 may be connected to a portion of the follower 306 by contacting the distal surface of the tube 331 to a surface 333 of the follower that is located along the linear path along with the leaf shaft 308 translates, as depicted in FIG. 3B. Rotation of the actuator shaft 309 by the rotator motor 312 transitions the latch 310 between a first locked configuration where the end faces of the protrusions 338 of the inner ring are aligned with the end faces of protrusions 334 of the tube lumen 332 (depicted in FIG. 3H) and a second unlocked configuration where the end faces of protrusions 338 of the inner ring are not aligned with the end faces of protrusions 334 of the tube lumen (depicted in FIG. 3I). In the second configuration, the protrusions 338 of the inner ring 336 may be located in the spaces between the protrusions 334 of the tube. In the first configuration, as depicted in FIG. 3H, the opposing contact between the end faces of the protrusions of the inner ring and the elongate tube transfers the force and movement of the follower to the leaf shaft, such that the shaft is linearly translated as the cam drives the follower. The follower may pivot during the lift events, the pivoting of which translates to a linear motion of the leaf shaft. In the second configuration, as depicted in FIG. 3I, the end faces of the protrusions of the inner ring and the elongate tube are no longer in face to face opposing contact, and the protrusions 334 of the elongate tube are slidably received in the space between the protrusions 338 of the inner ring. Accordingly, the force and movement of the follower 306 is not transferred to the leaf shaft 308, and the elongate tube slips with respect to the inner ring as the cam drives the follower.

Figure 3E:
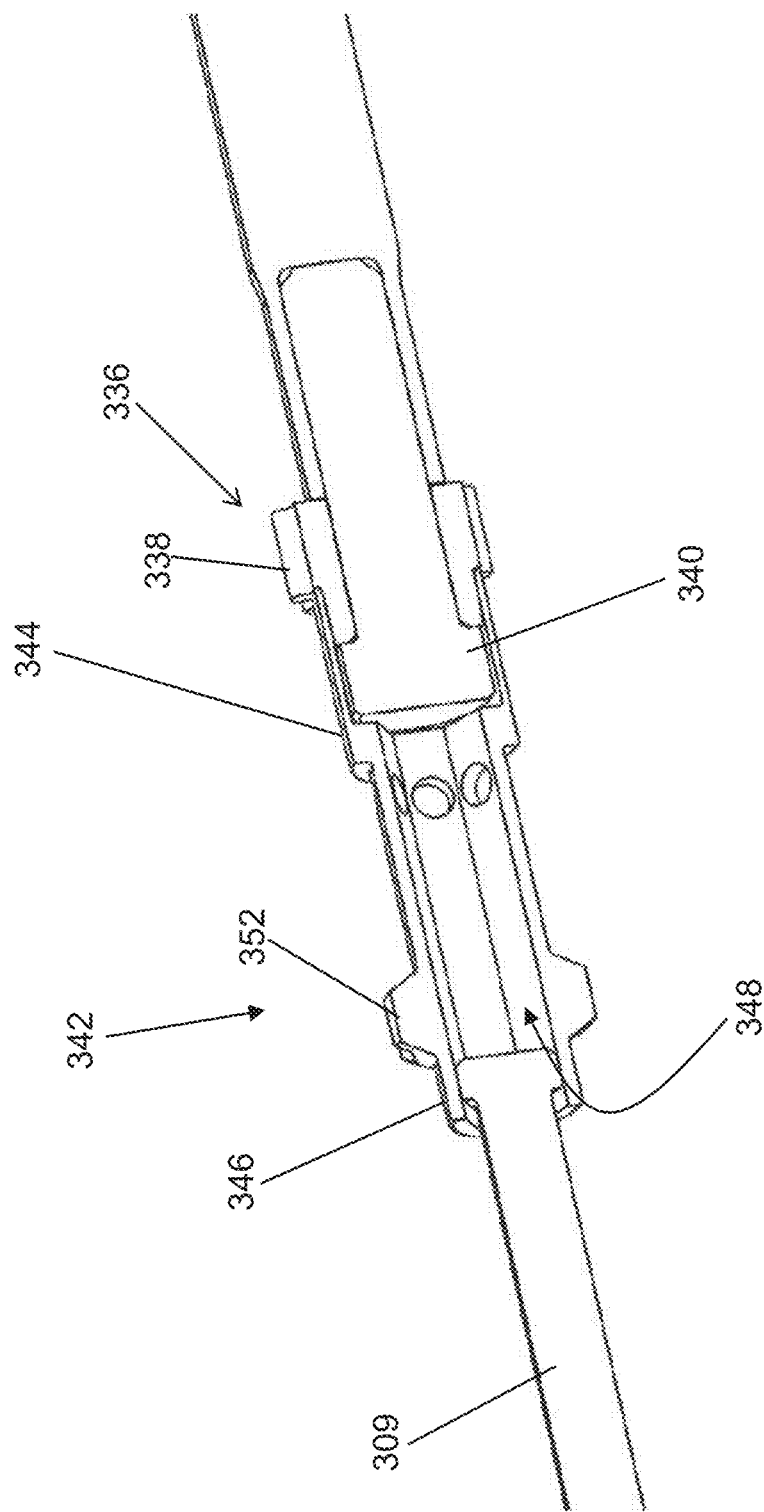
FIG. 3E is a perspective cross-sectional view of the latch mechanism of FIG. 3B.
Figure 3F:
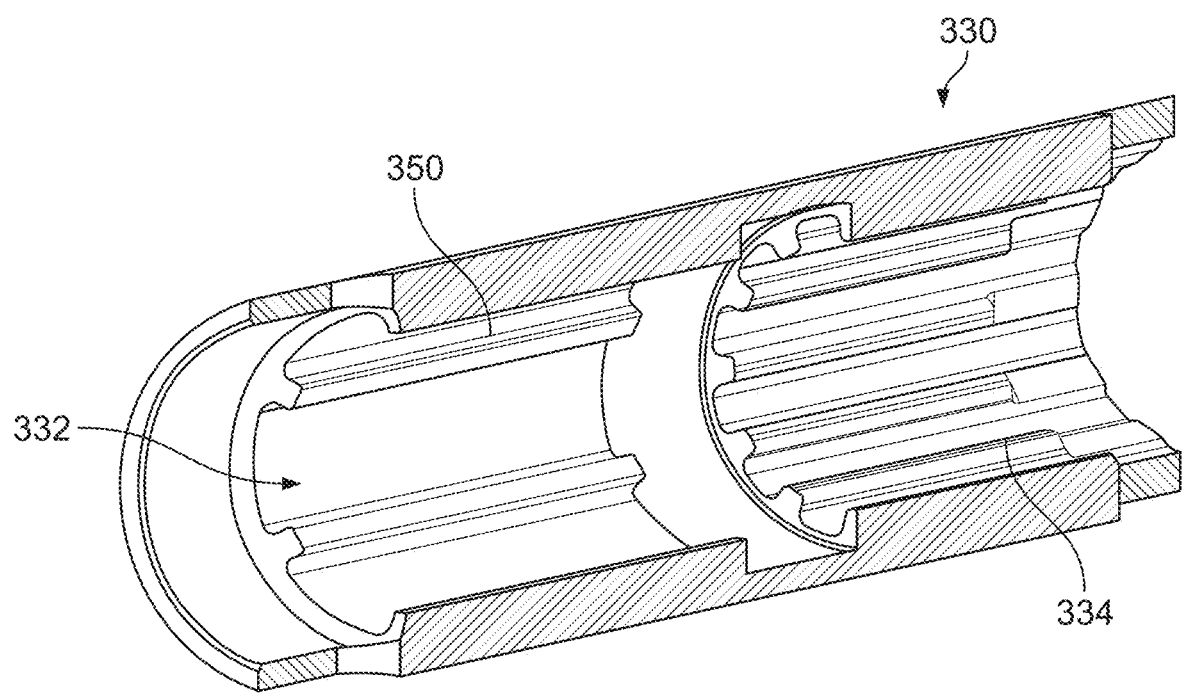
FIG. 3F is a perspective cross-sectional view of a component of the latch mechanism of FIG. 3B.
Figure 3G:
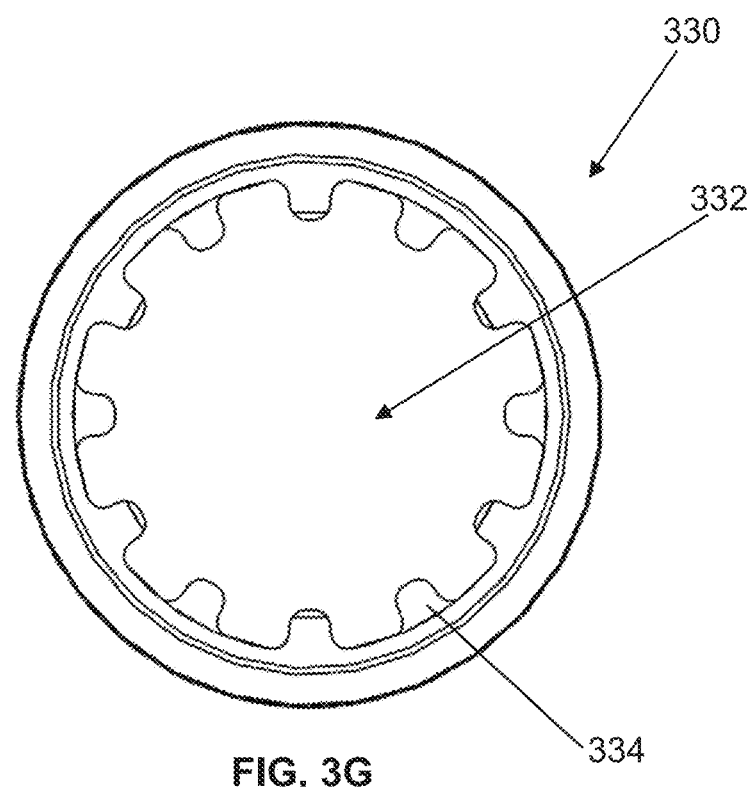
FIG. 3G is an end view of a component of the latch mechanism of FIG. 3B.
Figure 3H:
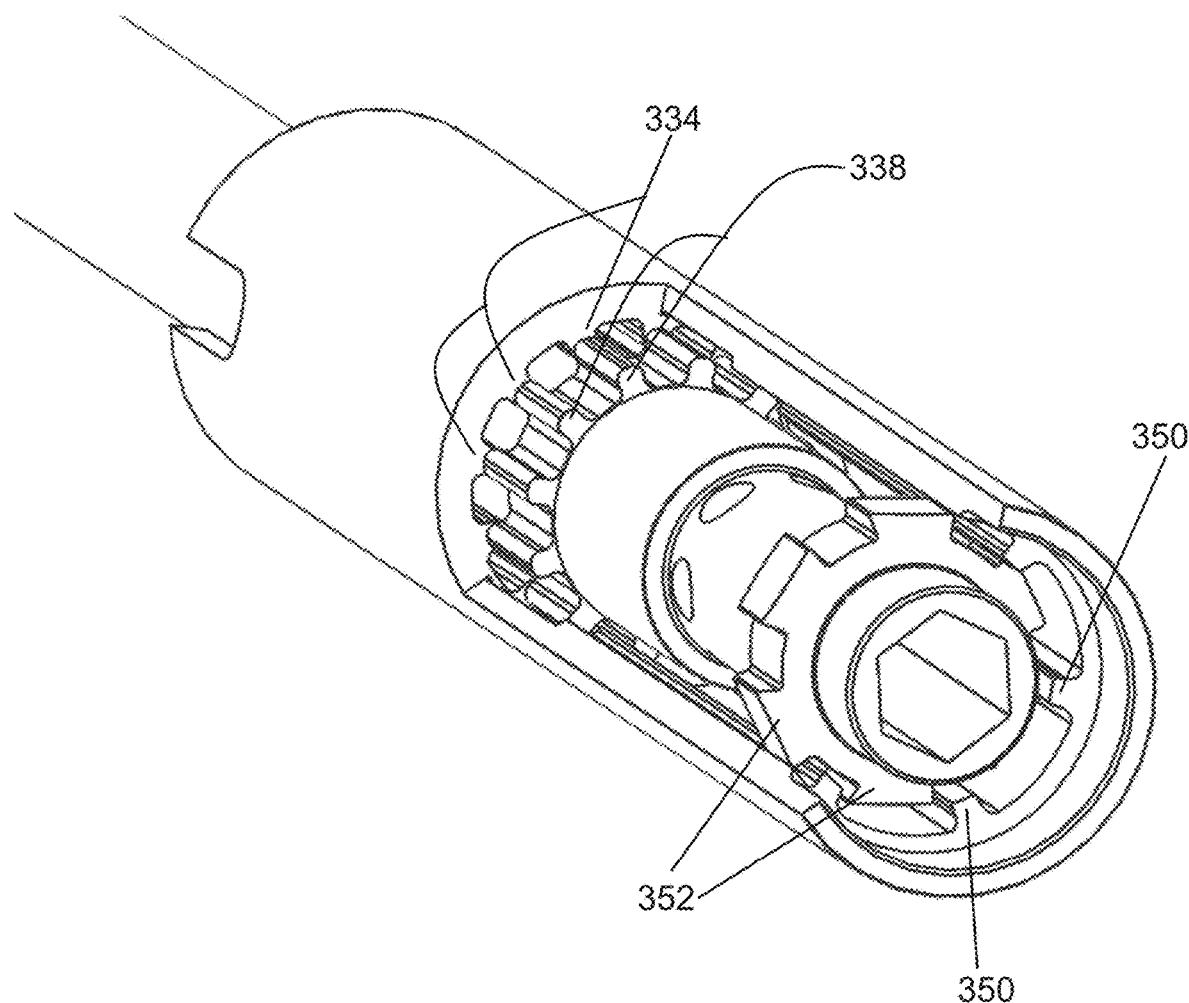
FIGS. 3H and 3I are perspective partial cutaway views of the latch mechanism of FIG. 3B in the locked (FIG. 3H) and unlocked (FIG. 3I) configurations.
Figure 3I:
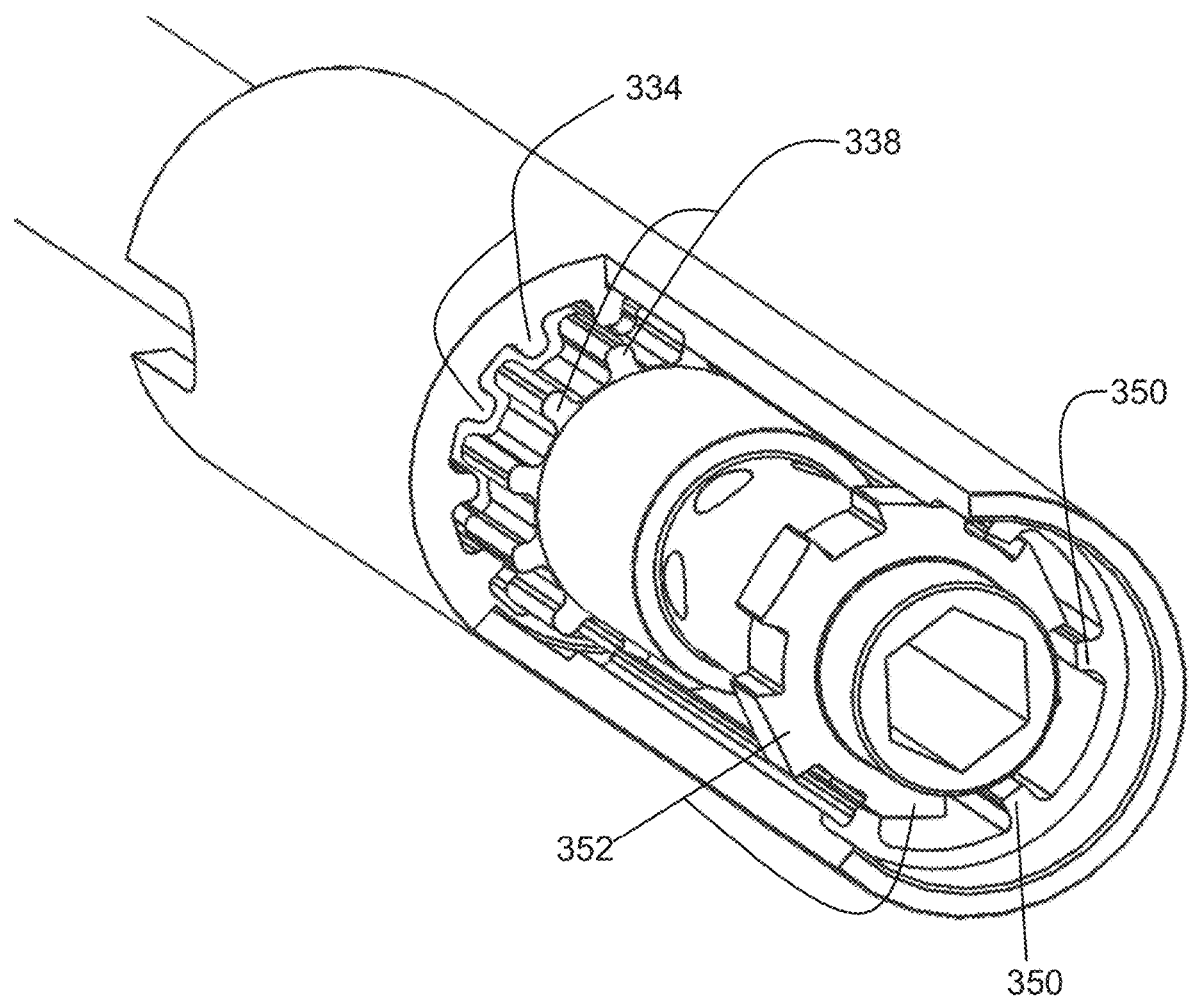
Figure 3J:
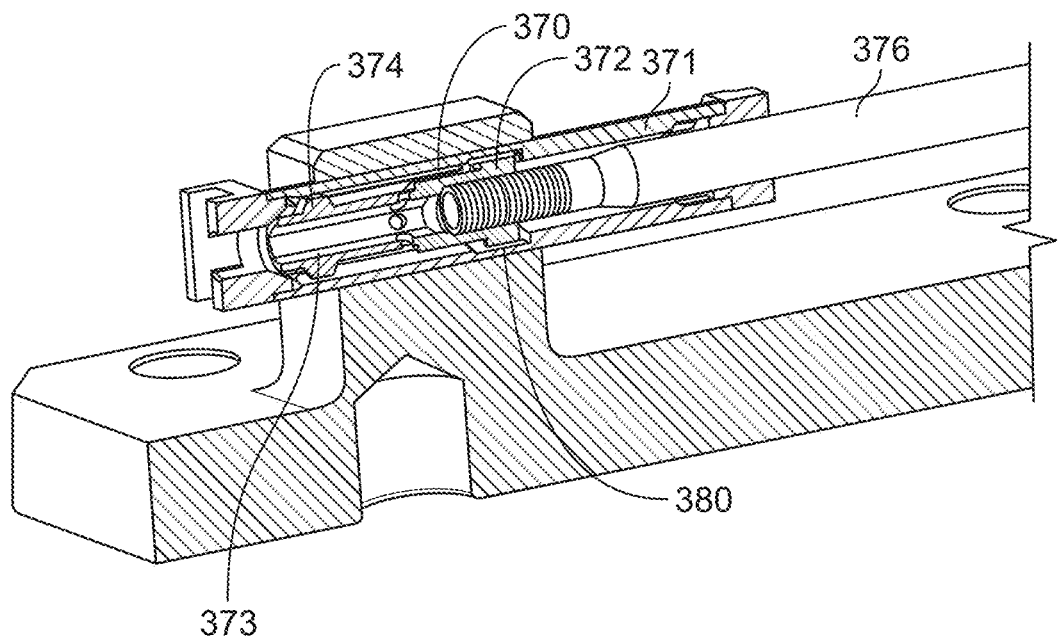
FIGS. 3J and 3K are views of another variation of a latch mechanism.
Figure 3K:
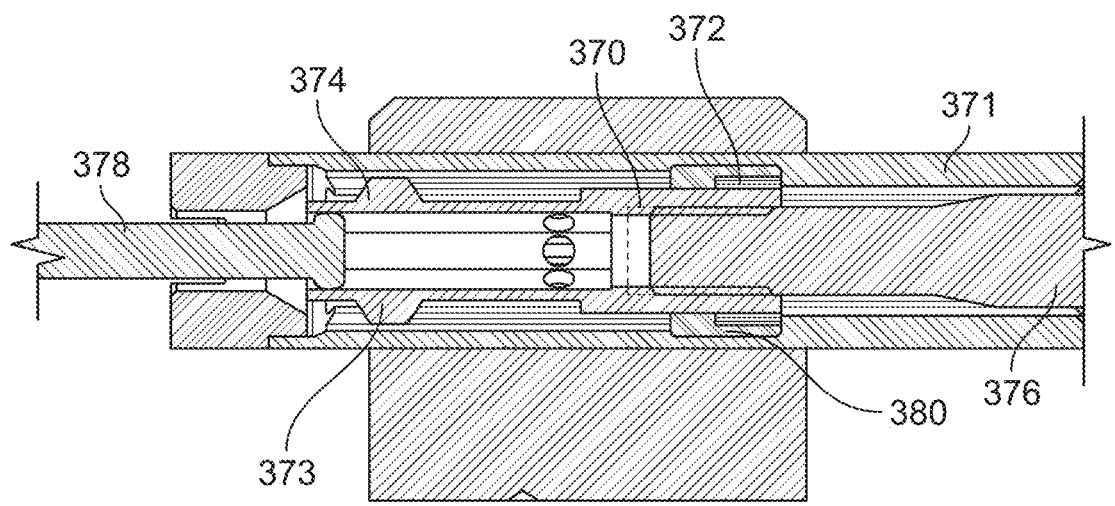

One variation of how the inner ring of a latch mechanism may be rotatably coupled to the leaf shaft is depicted in FIGS. 3C-3E. As shown in FIG. 3D, a plug 340 may be inserted through the opening 337 of the inner ring 336 and inserted into a lumen 339 of the leaf shaft 308. The plug 340 may be fixably attached to the leaf shaft 308, for example, by friction welding, or laser welding, such that the inner ring 336 is captured between the proximal end 343 of the plug 340 and the proximal end of the leaf shaft. The diameter of the body 341 of the plug may be less than the diameter of the ring opening 337, which may allow the inner ring to rotate with respect to the plug 340 and the leaf shaft 308, but the widened proximal end 343 of the plug captures the inner ring 336 against the leaf shaft 308. The inner ring may be rotatably coupled to the leaf shaft in other ways, for example, as depicted in FIGS. 3J-K and described in more detail below.

Rotation of the inner ring 336 may be driven by the rotary motor via the actuator shaft. One variation of how the actuator shaft 309 may be coupled to the inner ring is depicted in FIG. 3E. As shown there, the actuator shaft may be attached to the inner ring 336 using a tubular connector 342, where one end of the tubular connector (e.g., the distal end 344) is attached to the inner ring 336 and the other end of the tubular connector (e.g., the proximal end 346) is attached to the actuator shaft 309. For example, a lumen 348 of the tubular connector may be sized and shaped at the distal end 344 to accommodate a proximal collar of the inner ring 336 and/or the plug 340 such that the tubular connector 342 may be friction fit with the collar of the inner ring. The lumen 348 of the tubular connector may be sized and shaped at the proximal end to accommodate the distal end of the actuator shaft such that the tubular connector 342 may be a sliding fit with the actuator shaft such that rotating the actuator shaft rotates the tubular connector and the actuator shaft can slide axially inside the tubular connector. The tubular connector and the inner ring may be coupled such that rotation of the tubular connector by the actuator shaft causes a corresponding rotation of the inner ring. In some variations, the tubular connector and the inner ring are rotatable with respect to the leaf shaft and the plug.

The tubular connector 342 may attach the actuator shaft 309 to the inner ring 336 inside the lumen 332 of the elongate tube 330. Some variations of a tubular connector 342 may comprise features that may help to retain its rotational orientation with respect to the elongate tube 330. For example, as depicted in FIG. 3F, the inner surface of the elongate tube 330 may comprise a second set of protrusions or splines 350 proximal to the first set of protrusions 334 (i.e., the protrusions 334 that correspond with the protrusions of the inner ring 336), and the outer surface of the tubular connector 342 may comprise one or more protrusions 352 that correspond to the second set of protrusions 350. There may be any number of protrusions on the inner surface of the elongate tube lumen and on the outer surface of the tubular connector, for example, 2, 3, 4, 5, 6, 8, 10, 12, 14, 20, etc. The variations depicted in FIGS. 3D and 3F have 6 protrusions. These protrusions or splines may act as rotary stops as the actuator shaft 309 rotates the inner ring 336 to transition the latch mechanism between the first configuration (i.e., where the motion of the leaf shaft is locked to the motion of the follower) and the second configuration (i.e., where the motion of the leaf shaft is not locked to the motion of the follower). The protrusions 352 on the outer surface of the tubular connector 342 may be angularly offset from the protrusions 338 on the outer surface of the inner ring 336, as depicted in FIGS. 3E, 3H, 3I, such that when the protrusions 352 of the tubular connector are at a first rotary position with respect to the protrusions 350 of the elongate tube 330, the latch is in the first locked configuration and when the protrusions 352 are at a second rotary position with respect to the protrusions 350, the latch is in the second unlocked configuration. A rotary position is one in which the protrusions 352 are located in the spaces between protrusions 350 and vice versa. That is, in the first rotary position, the end faces of protrusions 338 of the inner ring are aligned with the end faces of the protrusions 334 of the tube lumen 332 (e.g., the protrusions 338 abut the protrusions 334, as depicted in FIG. 3H). In the second rotary position, the end faces of protrusions 338 of the inner ring are not aligned with the end faces of the protrusions 334 of the tube lumen 332 (e.g., the protrusions 338 are instead located in the spaces between the protrusions 334, as depicted in FIG. 3I). In use, the tubular connector 342 may be rotated in a first direction (e.g., clockwise) to transition the latch from the first locked configuration to the second unlocked configuration and rotated in a second direction opposite the first direction (e.g., counterclockwise) to transition the latch from the second unlocked configuration to the first locked configuration. Alternatively in some variations, the tubular connector 342 may be rotated in a single direction to transition the latch between the first locked configuration and the second unlocked configuration, where each rotary stop transitions the latch (i.e., every other rotary stop corresponds to the first locked configuration and the remaining other rotary stops correspond to the second unlocked configuration).

The travel angle (i.e., the rotation angle needed to move from the locked configuration to the unlocked configuration) may depend at least in part on the number and size of the first set of protrusions. For example, the first set of protrusions 334 of the elongate tube 330 may comprise 12 protrusions, where each protrusion occupies an angular sweep of about 15 degrees, and the space between protrusions occupies an angular sweep of about 15 degrees. This spacing of protrusions would be the same for the protrusions 338 of the inner ring 336, and the travel angle would be 15 degrees, as this is the angle required to move the protrusions 338 from alignment with protrusions 334 (corresponding to the first locked state), to mesh with protrusions 334 so that the protrusions 338 align with spaces between the protrusions 334 and thus slide axially (corresponding to the second unlocked state). The second set of protrusions 352 of the elongate tube 330 which correspond with protrusions 352 of the tubular connector 342 may have an angular sweep that is different from the angular sweep of the first set of protrusions 334, so that the tubular connector 342 can be rotated with respect to the elongate tube 330 through the travel angle. For example, the second set of protrusions may have six protrusions 350 having an angular sweep of 15 degrees with a space between protrusions of 45 degrees, but the protrusions 352 on the tubular connector 342 may have an angular sweep of 30 degrees with a space between the protrusions of 30 degrees. The protrusions 352 on the tubular connector 342 would be axially aligned with, and have the same angular sweep as the protrusions 350 on the elongate tube 330. The protrusions 352 on tubular connector 342 are offset (center to center) by 22.5 degrees from the protrusions 338 of the inner ring 336. The protrusions 352 fit in the space between protrusions 350, and are thus able to rotate through the 45−30=15 degrees of the travel angle. This rotation, in which a protrusion 352 moves from contact with one protrusion 350 to contact with the neighboring/adjacent protrusion 350, causes alignment or meshing of protrusions 338 and protrusions 334, and thus transition between the locked and unlocked configurations. The rotation that gives rise to these transitions may occur during the base-circle portion of the cam rotation, because only then are the protrusions 334 and protrusions 338 axially displaced from each other.

Another variation of the coupling between the actuator shaft, latch, and leaf shaft is depicted in FIGS. 3J-3K. As depicted there, there may be a single tubular connector 370 with a central lumen 373, where the distal end of the lumen is configured to couple with the leaf shaft 376 and the proximal end of the lumen is configured to couple with the actuator shaft 378. The tubular connector 370 may be located within the lumen of an elongate tube 371, which may be similar to the elongate tube 330 as previously described. The tubular connector 370 may comprise a first set of protrusions 372 that are distal to a second set of protrusions 374, where the first set of protrusions 372 may be similar to the protrusions 338 of the inner ring and the second set of protrusions 374 may be similar to the protrusions 352 of the tubular connector. The elongate tube 370, like the elongate tube 330 of the previous variation, may also comprise a first set of protrusions that correspond with (e.g., complementary to) the first set of protrusions 372 of the tubular connector and a second set of protrusions that correspond with (e.g., complementary to) the second set of protrusions 374. The tubular connector 370 may comprise a recess or grooved region 380 at a proximal portion of the lumen 373, which recess is configured with a stop to axially retain the leaf shaft 376 such that the tubular connector is rotatable with respect to the leaf shaft, but does not move axially (e.g., laterally) with respect to the leaf shaft. For example, the tubular connector 370 and the leaf shaft 376 may be coupled using a threaded interface. A threaded interface may permit some small axial translation of the tubular connector 370 with respect to the leaf shaft 376 during rotation of the tubular connector. This small translation can be allowed for by properly sizing the axial gap in the elongate tube 370 so as to ensure that the translation does not itself engage or disengage the distal protrusions 372 and their complementary protrusions on the elongate tube. Unlike the previous variation depicted in FIGS. 3B-I, this variation has fewer separate parts and avoids the need to weld or otherwise rigidly join parts, which may help to simplify the manufacturing and assembly process.

Figure 3L:
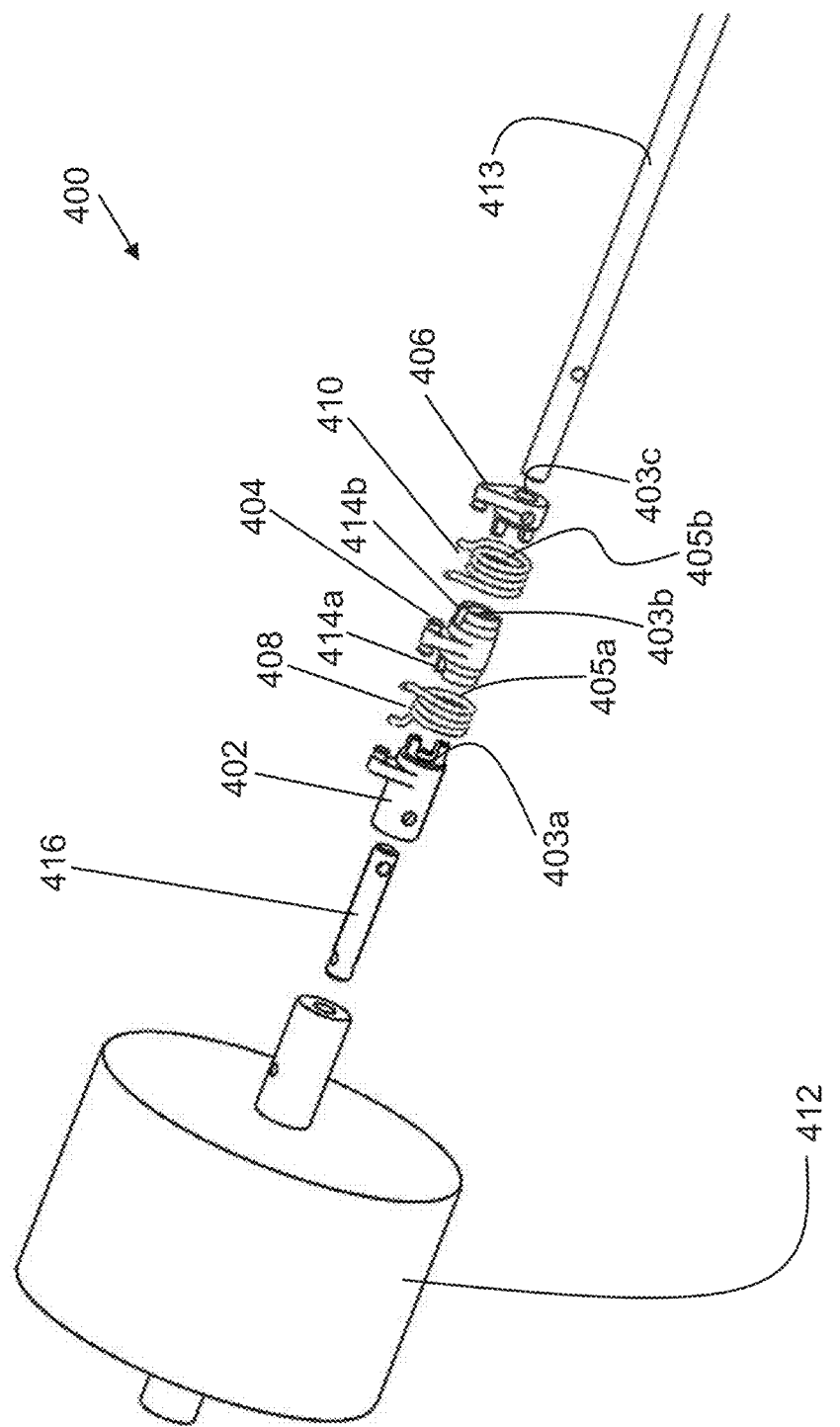
FIG. 3L is a perspective exploded component view of a torsion spring assembly of a cam-based leaf drive mechanism.

In some variations, it may be desirable to reduce the time it takes the latch mechanism to transition between the first locked configuration and the second locked configuration. For example, it may be desirable for the latch to switch from the first configuration to the second configuration in the base circle duration, and/or be able to switch in less than about 10 ms, e.g., less than about 1 ms. In some variations, a high-speed selectively-switchable latch mechanism for a cam and follower leaf drive mechanism may have a torsion spring assembly that may be configured to allow a solenoid to move during the lift event to charge-up a helical torsion spring, and then during the base circle duration (the non-motion period of the cam and follower cycle) the torsion spring may cause rotary motion of the tubular connector. Due to the small rotational inertia of the rotary latch, a helical torsion spring may cause latch or un-latch motion in less than 1 ms whereas the fastest electro-mechanical devices cannot perform the same rotary motion in less than 1 ms. Reducing the duration time to engage or disengage the latch increases the duration time for the motion of the shaft. In some variations, a torsion spring assembly may switch the latch in less than 10 ms, which may allow the latch to operate at frequencies greater than 50 Hz. One variation of a torsion spring assembly that may help to increase the switch speed of the latch is depicted in FIG. 3L. As shown there, a torsion spring assembly 400 may comprise a proximal stop piece 402, a middle stop piece 404, a distal stop piece 406, a first torsion spring 408 located between the proximal stop piece 402 and the middle stop piece 404 and a second torsion spring 410 located between the distal stop piece 406 and the middle stop piece 404. The proximal, middle and distal stop pieces may each comprise an opening (403a,b,c) and are arranged such that the openings of all of the stop pieces and the openings (405a,b) of the first and second torsion springs 408, 410 may be aligned and coaxial with an actuator shaft 413 (which may be similarly arranged to the actuator shaft 309 depicted in FIGS. 3A-B). The middle stop piece 404 may have a first lip or collar 414a on a proximal side configured to fit with the opening 403a of the proximal stop piece 402 and a second lip or collar 414b on a distal side configured to fit with the opening 403c of the distal stop piece 406. The opening 403a of the proximal stop piece 402 may be sized and shaped to fit with a solenoid shaft 416 of the solenoid or rotary actuator 412 such that the solenoid shaft 416 is coupled to the proximal stop piece 402. The proximal stop piece 402 may have one or more protrusions or rotary stop features that correspond with one or more protrusions or rotary stop features on a proximal surface of the middle stop piece 404. The opening 403c of the distal stop piece may be sized and shaped to fit with the actuator shaft 413 such that the actuator shaft is coupled to the distal stop piece 406. The distal stop piece 406 may have one or more protrusions or rotary stop features that correspond with one or more protrusions or rotary stop features on the distal surface of the middle stop piece 404. The actuator shaft 413 may extend through and may be coupled to the distal stop piece 406, and the opening 403b in the middle stop piece 404 may be sized and shaped to fit with the actuator shaft 413 so that the middle stop piece 404 can rotate freely on the actuator shaft 413. The actuator shaft 413 may extend through the middle stop piece 404, and the opening 403a on the proximal stop piece 402 may be sized and shaped to fit the actuator shaft 413 so that the proximal stop piece 402 that is coupled to the solenoid shaft 416 may rotate freely on the actuator shaft. Rotation of the solenoid shaft 416 by the rotary actuator 412 during a cam lift event may charge up the first torsion spring 408, and cause it to propel the switching of the inner ring from the first configuration to the second configuration during the cam base cycle duration by causing a rotation of the middle stop piece 404 such that the rotary stop features of the middle stop piece 404 engage the rotary stop features of the distal stop piece 408 and cause it and the actuator shaft 413 to rotate. Rotation of the solenoid shaft 416 by the rotary actuator 412 in the opposite direction during a cam lift event may cause the rotary stop features of the proximal stop piece 402 and the middle stop piece 404 to engage, rotating the middle stop piece 404 and causing it to charge of the second torsion spring 410. This may cause the second torsion spring 410 to propel the switching of the inner ring from the second configuration to the first configuration by rotating the distal stop piece 406 and the coupled actuator shaft. The motion of the rotary actuator/motor 412 that occurs during a cam lift event may cause at least one of the torsion springs to "charge up" (i.e., retain potential energy). The retained potential energy is then released in order to quickly switch the latch from one configuration to the other. As can be appreciated, during a cam lift event, the end faces of splines 338 and 334 on the inner ring 336 and the elongate tube 330 respectively will either be (a) lined up and pushing on one another to move the leaf in the direction of arrow 319 (open) or (b) they will be "meshed" or interleaved and telescopingly sliding past each other to take up all the cam motion, with the spring 316 returning the leaf to the closed position. The torsional springs of the torsional spring assembly may allow the rotary actuator 312/412 to start moving ahead while the cam is still in the lift event to prepare for the next state transition during the next base circle event. These torsional springs "load up" during the lift event, building up a torque on the latch. The torque cannot move the latch during the lift event, because either (a) there may be too much friction on the splines to allow rotation or (b) the mesh of the splines may prevent rotation. But as soon as the latch becomes unloaded and the splines separate axially, the springs can snap the latch to the new configuration. So the torsional spring assembly may help to lengthen the time for the rotary actuator to add energy into the system to execute the latch transition in the very short time allowed by the base circle duration of the cam. The torsional springs may also allow for a very short base circle, and therefore more cam angle devoted to the lift event, which may result in smoother lift event accelerations.

Figure 3M:
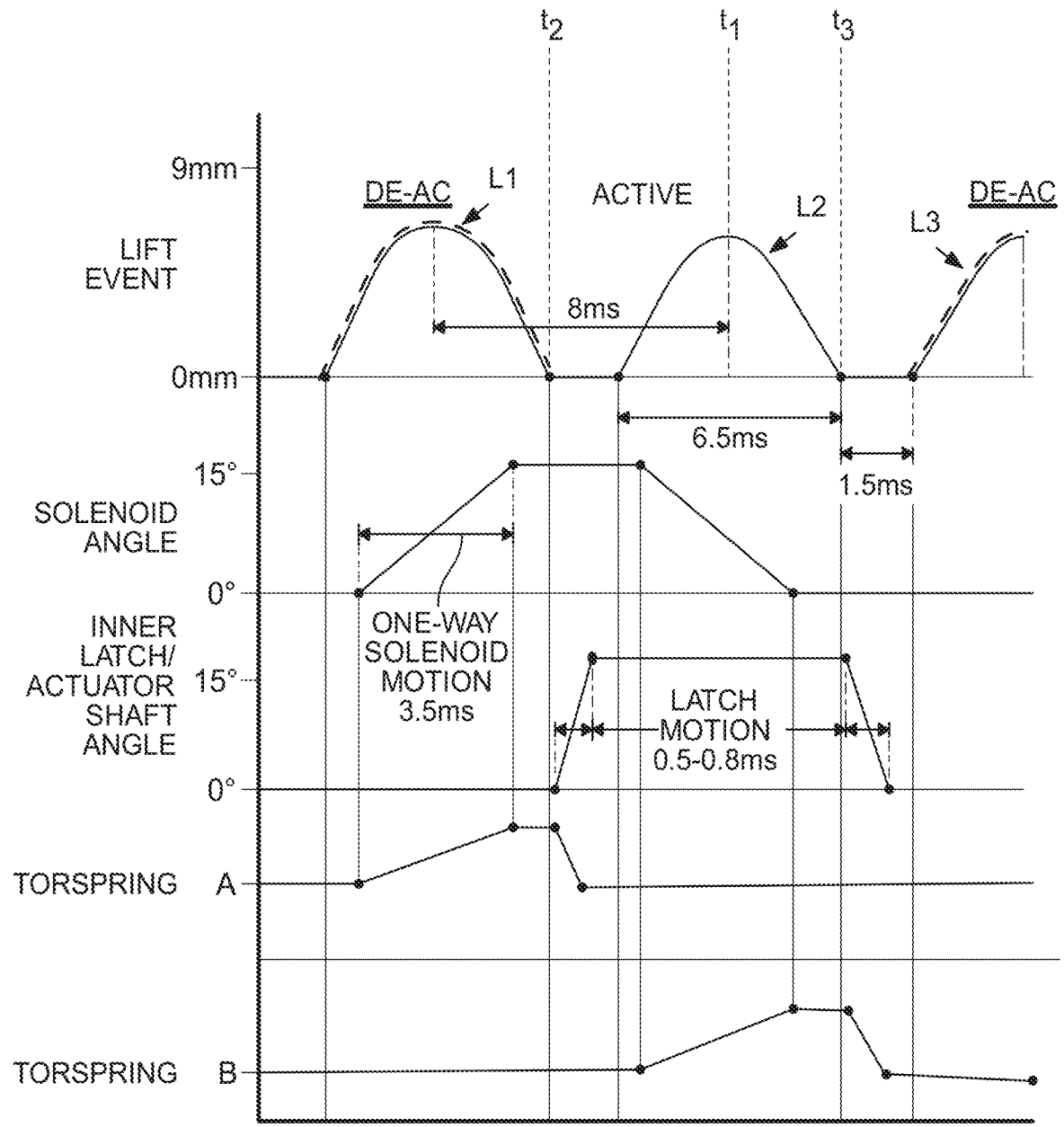
FIG. 3M is a timing diagram that outlines the sequence of events before, during and after a latch transition.

The operation of this variation of the cam-based leaf drive mechanism can be further explained by reference to FIG. 3M, which is one variation of a timing diagram showing the interaction between the cam, rotary actuator, rotational position of the inner ring member, and the springs of the torsion spring assembly. In this variation, the leaf transition time (e.g., the time it takes for a leaf to transition from the first locked configuration to second unlocked configuration, or vice versa) may be about 8 ms, and the time in which the leaf may remain in in the open position may be about 2 ms (e.g., this may correspond to the dwell time of the cam). The timing diagram of FIG. 3M illustrates the sequence of events that leads to the transition of the latch from an unlocked configuration to a locked configuration and back to the unlocked configuration within a 10 ms period (e.g., where the latch is locked for just one lift event), so that the leaf is in the open position by time point $t_1$, which occurs during lift event L2. The first row represents the cyclical rotation of the continuously rotating cam, where a lift event occurs as the cam rotates, causing the follower to translate from 0 mm to 9 mm at it moves from the base circle of the cam up the cam lobe. The base circle duration is the time in which the follower is riding along the base circle radius, and is the time in which the latch can most readily transition between the locked and unlocked configurations. In this example, the base circle duration is about 1.5 ms. During the lift event L1 prior to the target lift event L2, the rotary actuator or solenoid may begin to rotate the solenoid shaft 15 degrees or more in a first direction, as depicted in the second row of the timing diagram. As the solenoid shaft rotates in the first direction, torsion spring A (e.g., the proximal torsion spring 408) may be "charged" such that potential energy is stored in the spring. The torsion spring A may be prevented from releasing the stored potential energy due to the frictional forces between the splines of the inner ring and the elongate tube or the interleaving of the splines. Once the cam rotates through the lift event L1 and begins the base cycle duration at time point $t_2$, splines of the inner ring and the elongate tube are no longer in contact (e.g., friction between them is zero or no longer meshed or interleaved), and the stored potential energy in torsion spring A may be released, thereby rotating the actuator shaft and transitioning the latch from the unlocked configuration (at 0 degrees) to the locked configuration (at 15 degrees), as depicted in the third row of the timing diagram. This transition may occur within 1.5 ms, for example, in about 0.5 ms to about 0.8 ms. Once the latch is in the locked configuration, the leaf shaft moves in concert with the cam and follower, so that during lift event L2, by time point $t_1$, the leaf may be in the open position. To transition the latch back to the unlocked configuration by lift event L3, the solenoid may begin to rotate in a second direction opposite to the first direction during lift event L2, depicted as the negative slope in the second row of the timing diagram. This rotation may charge torsion spring B (e.g., the distal spring 410) such that potential energy is stored in the spring. Once the cam rotates through the lift event L2 and begins the base cycle duration at time point $t_3$, the stored potential energy in torsion spring B may be released, thereby rotating the actuator shaft and transitioning the latch from the locked configuration (at 15 degrees) to the unlocked configuration (at 0 degrees), depicted as the negative slope in the third row of the timing diagram. This transition may occur within 1.5 ms, for example, in about 0.5 ms to about 0.8 ms.

Figure 4:
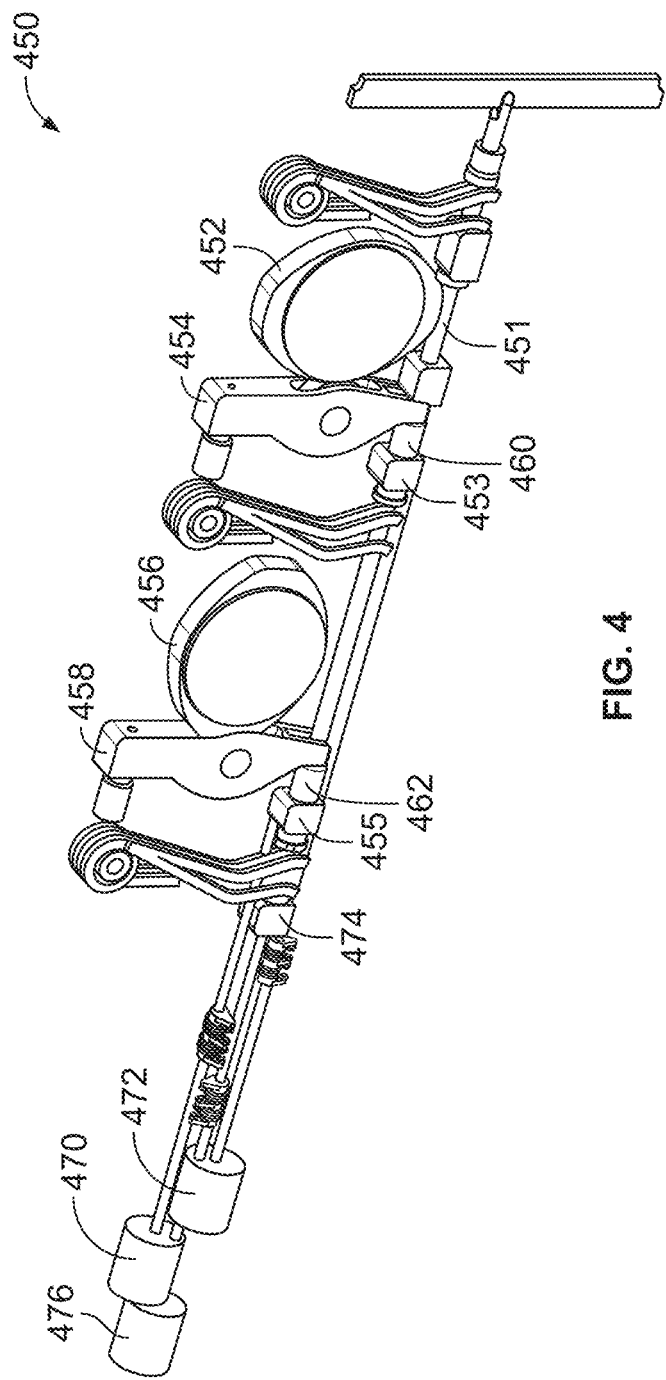
FIG. 4 is a perspective view of another variation of a cam-based leaf drive mechanism.

One variation of a cam-based actuator that may be used to retain the leaf in the open configuration may comprise two cams having lobes that are offset such that the movement of the followers that they each drive are out-of-phase with each other. That is, when a first follower is riding on a lobe of the first cam, a second follower is not riding on the lobe of the second cam and vice versa. For example, a cam-based drive mechanism used to transition a leaf between an open position and a closed position may comprise a first cam having two lobes and a corresponding first follower, a second cam having two lobes and a corresponding second follower, wherein the lobes of the second cam are 90 degrees offset from the lobes of the first cam, and a plurality of latch mechanisms that selectively connects either the first follower or the second follower to the leaf shaft. Each cam supports opening a leaf at every other firing position, so to transition a leaf from closed to open at a given firing position for the gantry, one of the two cams will be utilized to provide the motive force for the leaf, and to transition from closed to open at the neighboring firing position, the other cam would be utilized. To retain the leaf in the open position, a top latch is engaged to hold the shaft to which the leaf is connected, and both cam latches are dis-engaged. To move a leaf, the leaf may be alternately connected to the first cam and follower and the second cam and follower during the dwell time of each of the cams (i.e., the duration of time when a lobe of the cam is contacting the follower), such that as the dwell time for one cam ends, the leaf shaft is disengaged from that follower and engaged to other follower as the dwell time for the other cam begins. One example of such a cam-based drive mechanism is depicted in FIG. 4. This variation of a cam-based drive mechanism 450 comprises a first cam 452 having two lobes, a first follower 454 in contact with the first cam 452, a second cam 456 having two lobes positioned such that the two lobes are 90 degrees offset with respect to the lobes of the first cam 452, a second follower 458 in contact with the second cam 456, a first latch 460 that selectively engages the first follower 454 with the leaf shaft 451, a second latch 462 that selectively engages the second follower 458 to the leaf shaft 451. Optionally, the cam-based leaf drive mechanism 450 may comprise a first shaft guide 453 located adjacent to the first latch 460 and a second shaft guide 455 located adjacent to the second latch 462. The cam-based drive mechanism may also comprise a first rotary actuator 470 and a second rotary actuator 472 that are each configured to transition the first latch and the second latch respectively between a first configuration where the follower is engaged with the leaf shaft and a second configuration where the follower is disengaged from the leaf shaft. The structures of the cams, followers, latches, torsion spring assembly, and rotary actuators may be similar to the corresponding components described above. The first and second rotary actuators may be controlled (e.g., using controller software) such that either the first latch is in the first configuration or the second latch is in the first configuration, but not both. Optionally, in some variations, a third latch 474 and third rotary actuator 476 may help to ensure that only one cam/follower pair drives the leaf shaft at a time.

Figure 5:
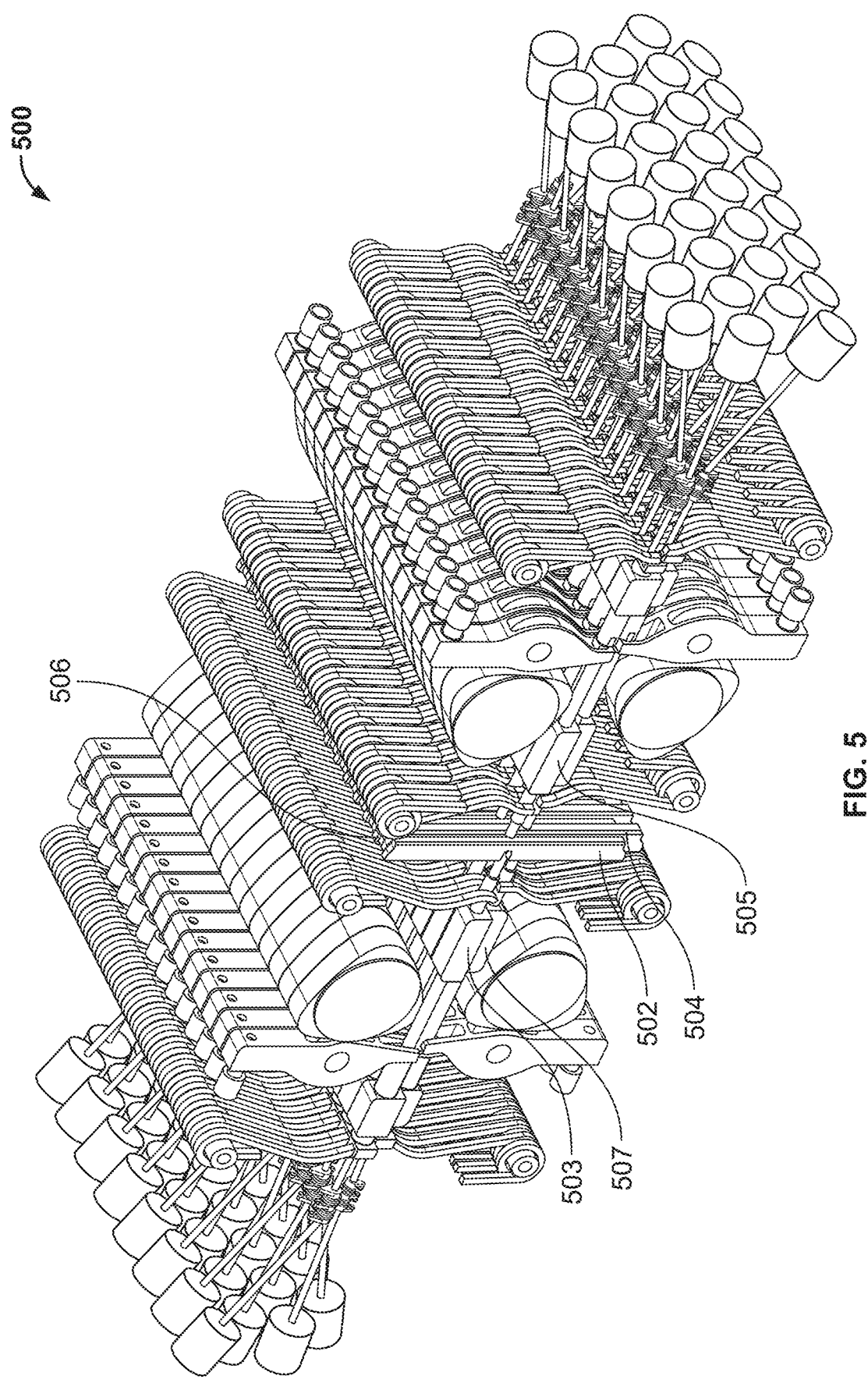
FIG. 5 is a perspective view of one variation of a package of cam-based leaf drive mechanisms.

The cam-based leaf drive mechanism (and any of the leaf drive mechanisms described herein) may be wider than the leaf itself. For example, a cam-based leaf drive mechanism may have a width from about 4 mm to about 6 mm, while the width of a leaf may be about 1 mm to about 2 mm. As such, it may be difficult to arrange the leaves to be adjacent to each other, with little or no space between leaves, since in doing so, there would not be enough space to accommodate the drive mechanisms that drive the leaves. Some variations of a multi-leaf collimator may be configured to actuate the leaves from both sides of the multi-leaf collimator and staggering the drive mechanisms vertically, so that the actuation is applied at different points for neighboring leaves (i.e., not along the center of mass of the leaf). However, at the high speeds of the leaf motion described herein, it may be helpful or desirable to actuate each leaf at or near (e.g., exactly along) the center of mass of the leaf, so as to not induce unwanted moments on the leaf. Such moments can cause oscillatory modes or vibrations, or cause binding in the leaf guides. FIG. 5 depicts one variation in which 64 leaves may be packaged such that the collimator leaves may be adjacent to each other and can accommodate each of the leaf actuators while providing for actuation through each leaf's center of mass. Collimator assembly 500 may comprise a first leaf 502, a second leaf 504 that is adjacent to the first leaf, and a third leaf 506 that is adjacent to the second leaf. The movement of the first leaf 502 may be driven by a first actuator 503 and the movement of the second leaf 504 may be driven be a second actuator 505. The first actuator 503 may be on one side (e.g., the left side) while the second actuator 505 may be on the opposite side (e.g., on the right side). Both the first and second actuators and first and second leaves may be at the same vertical height or location (i.e., the tops of the first and second leaves may be aligned). The third leaf 506 may be at a different vertical height or location from the first and second leaves, and may be driven by a third actuator 507. The third actuator 507 may be on the same side as the first actuator 503 (e.g., on the left side), but at a different vertical height or location (e.g., lower than the first actuator 503, as depicted in FIG. 5). A fourth leaf (not depicted) may be at the same vertical height as the third leaf 506 and driven by a fourth actuator located on the opposite side (e.g., right side) as the third actuator 507. As depicted in FIG. 5, in addition to staggering or offsetting the drive mechanisms in the vertical direction (i.e., along or parallel to the radiation beam path), the leaves themselves may also be staggered or offset in the vertical direction. That is, cumulatively over the 64 leaves, the leaves may be offset such that the first and second leaves may be at a first vertical location, third and fourth leaves at a second vertical location lower than the first vertical location, the fifth and sixth leaves at the first vertical location, the seventh and eighth leaves at the second vertical location, and so on (e.g., vertical height of the leaves would be staggered such that the first eight leaves would be high, high, low, low, high, high, low, low, and so on). There may be any number of vertical positions across which the leaves may be staggered. Every other leaf coming from the same side of the collimator may be in a higher vertical position and every other leaf coming from the same side of the collimator may be in a lower vertical position, which may similarly shift the center of mass of the leaves in the vertical direction. In order to drive the leaves through each leaf's center of mass, the drive mechanisms may be similarly vertically shifted. Such vertical shifts to the leaves and the leaf drive mechanisms may provide enough horizontal space to accommodate the width of the drive mechanism. Although FIG. 5 depicts a collimator comprising a cam-based drive mechanism, it should be understood that this arrangement may be used with any of the leaf drive mechanisms disclosed herein.

Figure 6A:
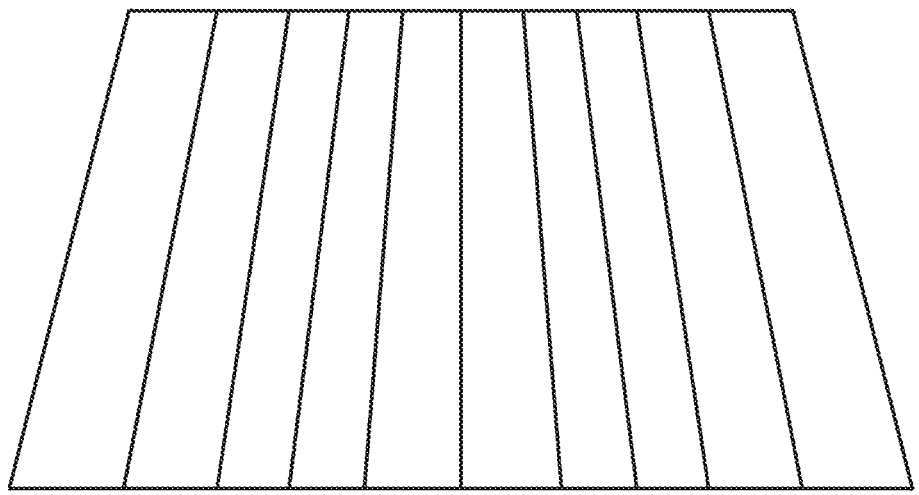
FIGS. 6A and 6B are side views of some variations of collimator leaves.

The collimator leaves in FIG. 5 and depicted herein in other drawings are depicted as being identical to each other and linearly arranged such that the top edge of each of the leaves is generally orthogonal to a radiation beam path from a radiation source. In such arrangement, the leaves may not be equidistant from the radiation source. Since the radiation typically emanates from a point or spot source (the linear accelerator target), the depth of each of the leaves (i.e., the dimension that is generally aligned with the direction of the radiation beam) and the width of each of the leaves (i.e., the dimension that is generally orthogonal to the direction of the radiation beam) may vary across the collimator, depending on the location of the leaf with respect to the radiation source. For example, the collimator leaves may have an asymmetric shape (when viewed from the side), where the parallel sides are the top and bottom sides of the leaf. The total length of the top edges of the leaves may be smaller than the total length of the bottom edge of the leaves, such as is depicted in FIG. 6A. The width of each of the leaves may be thicker or thinner at the left and right sides of the collimator than in the center of the collimator, to allow for more coarse or more precise delivery of radiation in different regions of the gantry bore.

Figure 6B:
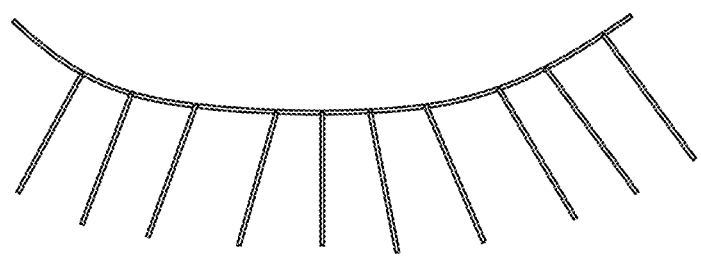

In other variations, collimator leaves may be arranged such that each leaf is equidistant from the radiation source. For example, the collimator leaves may form an arc or curve with respect to the beam path, as depicted in FIG. 6B. Each of the leaves may be a substantially symmetric trapezoid (e.g. isosceles trapezoid) and may have varying depths and widths.

Figure 6C:
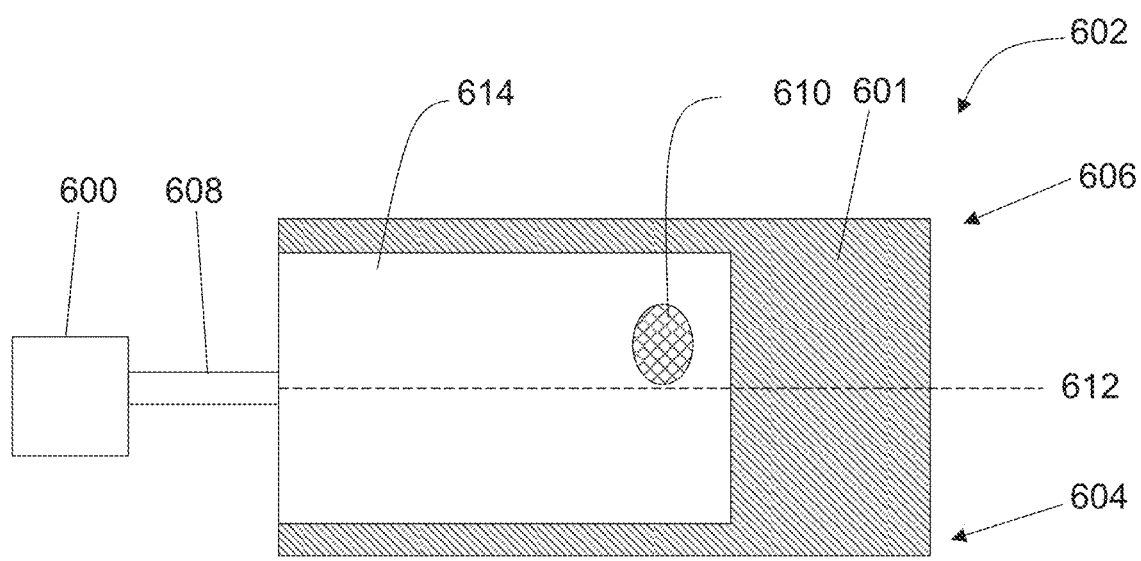
FIGS. 6C and 6D are side views of some variations of collimator leaves with weights to adjust the location of the center of mass.
Figure 6D:
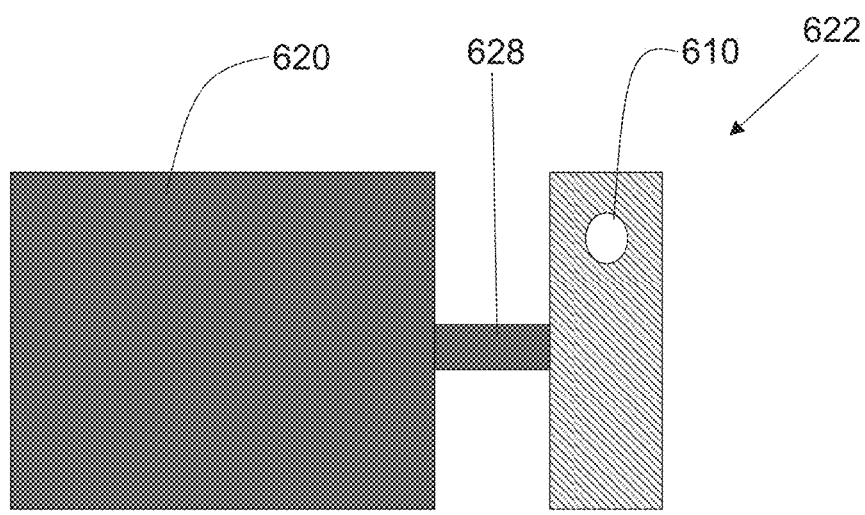

With the varying geometry of the leaves (e.g., asymmetric or symmetric trapezoidal leaves), it may be difficult to effectively vertically stagger the position of the leaves in the manner described above to be able to fit the leaf drive mechanisms together while also keeping the leaves in apposition with each other and having the drive mechanism drive the leaf at its center of mass. One variation of an arrangement of leaves and leaf drive mechanisms that may address these issues is schematically depicted in FIG. 6C, which depicts a side schematic view of a trapezoidal leaf assembly 602 comprising a leaf 601 (e.g., the portion of the leaf assembly made of a radiation impermeable material and/or enters the radiation beam path) where the bottom base portion 604 is wider (i.e., more massive) than the top base portion 606. Although trapezoidal-shaped leaves are described here, it should be understood that the leaves may have any desirable geometry, some of which may or may not have their center of mass located at a geometric center or axis of symmetry of the leaf. As shown FIG. 6C, a leaf drive mechanism 600 (e.g., any of the mechanisms described herein) may linearly translate a leaf along its center of mass via a leaf shaft 608. The center of mass of a leaf may vary depending on the shape of a leaf and in some cases, may not be at the geometric center of the leaf. For example, the trapezoidal leaf 602 may have a center of mass that is lower (e.g., closer to the bottom edge) than a rectangular leaf. A weight 610 having a particular mass may be placed at various locations on the leaf and/or the frame or support structure attached to the leaf to adjust the location of the center of mass. For example, the weight 610 may be placed higher up on a trapezoidal leaf 602 in order to raise the location of the center of mass so that it is closer to the geometric center 612 or to the top base portion of the leaf. The location where the shaft connects to the leaf, and therefore the location where the leaf drive mechanism drives the leaf may vary according to the location of the center of mass, which may be adjusted by the addition of one or more weights 610. While the weight 610 may be located on a radiation-permeable region of the leaf, the weight 610 may also be located on the radiation-impermeable region of the leaf, as shown in FIG. 6D. FIG. 6D depicts a trapezoidal leaf 622 connected by a shaft 628 to a leaf actuator 620 that may be any of the leaf drive mechanisms described herein. A weight 610 may be included on the radiation-impermeable portion of the leaf that may help to adjust the center of mass towards the top of the leaf 622. Alternatively or additionally, portions of the leaf and/or leaf assembly may be cut or hollowed out to adjust the location of the center of mass. The locations of the center of mass for differently shaped leaves of a multi-leaf collimator may vary, and the locations of the actuators may also vary such that they are vertically staggered. Vertically staggering the actuators may provide more space in the horizontal direction to sufficiently accommodate the array of actuators that drive the array of leaves.

Some variations of a leaf drive mechanism of a collimator included in a radiation therapy system (e.g., the emission guided radiation therapy system of FIG. 1) may comprise a spring system comprising one or more springs to transition the leaf between the open position and the closed position. Optionally, a leaf drive mechanism may further comprise an actuator system, which may include a latching mechanism. In some variations, spring-based leaf drive mechanisms may comprise a spring system comprising one or more springs connected to the leaf and a latch to retain the leaf in the closed position or the open configuration. The one or more springs may be coupled to both a stationary frame and a movable mass, coupled to only one of the stationary frame and movable mass, or simply be positioned between a stationary frame and a movable mass. Some spring systems may comprise a spring resonator. Different types of springs may be used, as desired, for example, coil springs, torsion springs, torsion bars, leaf springs, flexure elements, and the like. Springs with non-linear or step-wise linear spring constants may also be utilized to implement motion profiles other than pure sinusoids. Multiple springs may be used in parallel to generate sufficient force to move the leaf. Spring-based leaf actuation systems may comprise a brake or latch in order to capture and retain the leaf at a desired position (e.g., at the open position, closed position, the position where the leaf velocity is zero, the position where the maximum amount of potential energy is stored in the spring, etc.). Alternatively or additionally, a drive mechanism may comprise an actuator system that is coupled to the one or more springs (e.g., coupled to a moving mass disposed between two opposing springs and/or coupled to the spring near where the spring attaches to a stationary support), to add a "booster" force while the springs are in motion, which may augment the primary motive force provided by the spring system. An actuator system may comprise any of the actuators described herein, including, but not limited to, a pneumatic actuator, an electric motor (with or without a slotted-link mechanism), an electromagnetic voice-coil, a planar actuator, etc. Examples of suitable actuators may include linear or rotary actuators, and may be coupled to a transmission mechanism, e.g. rotary actuators coupled to a rack-and-pinion, etc. An actuator system may comprise an actuator and a brake/latch, which may optionally be combined into one unit or structure. In addition to restoring energy lost due to friction, the actuator system could also be used to start the system up from a de-energized state (when the leaf stationary at the center of travel) by exciting the spring resonator at the resonant frequency until the desired motion amplitude is achieved. The actuator may be coupled to the mount point of the spring, and may be configured to add energy by compressing or extending the spring. Alternatively or additionally, the actuator and/or latch may be coupled to the leaf.

Figure 7A:
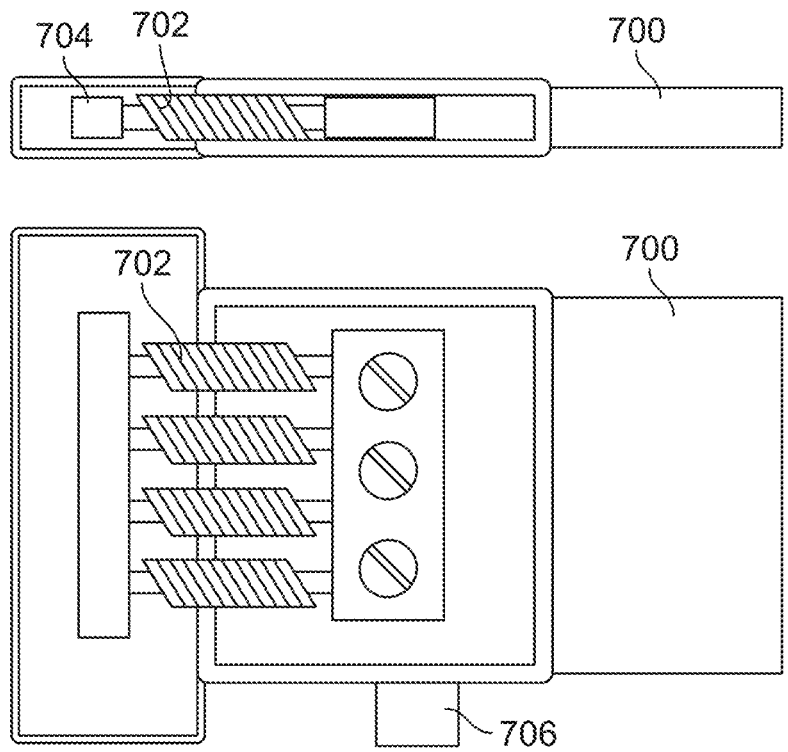
FIGS. 7A and 7B are schematic depictions of one variations of a spring-based leaf drive mechanism, where the top depiction is a view of the drive mechanism from a beam's eye view and the bottom depiction is a side view (i.e. view axis is perpendicular to the beam's eye view).
Figure 7B:
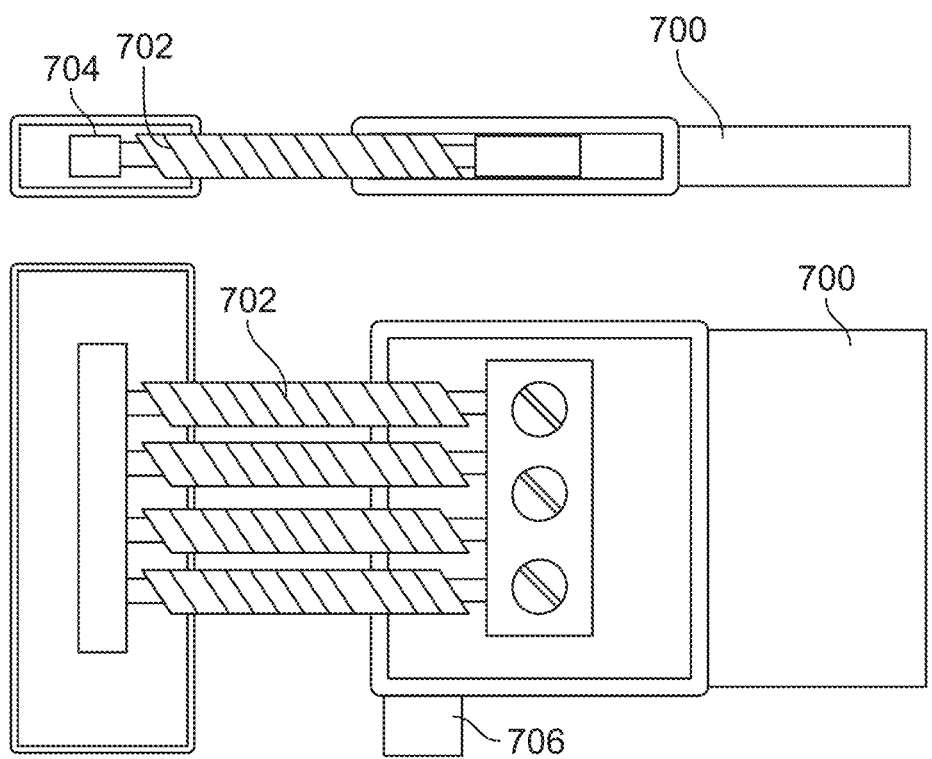

In one variation, a spring-based leaf drive mechanism of a collimator for use in a radiation therapy system may comprise a support, one or more springs attached between the leaf and the support such that the springs apply forces to the leaf to translate the leaf between the open and closed positions, and a latch configured to capture the leaf at a desired position. One variation of a leaf-based leaf drive mechanism is depicted in FIGS. 7A-7B. The leaf 700 is attached to a spring-based drive mechanism comprising one or more springs 702 where one end of the springs is attached to a stationary support 704 and the other end of the springs is attached to the leaf 700. The spring-based drive mechanism may also comprise a latch or friction brake 706. In the variation depicted in FIGS. 7A and 7B, the one or more springs 702 may apply a force such that the leaf 700 is moved to the open position (FIG. 7A) or the closed position (FIG. 7B). The latch 706 may be configured to capture the leaf 700 to retain it at the open or the closed position, thereby retaining potential energy in the one or more springs 702. While the one or more springs 702 are shown as comprising four springs, with each spring used in both compression and extension, are depicted, such a spring mechanism may have any number of springs, for example, 1, 2, 3, 4, 5, 6, 7, 8, 10, 12, etc. springs. The springs may all have the same spring constant, or may each have different spring constants. The springs may be used in any combination of compression and extension. For example, the one or more springs 702 may apply forces to the leaf 700 in both compression and extension. The one or more springs 702 may be configured such that when the spring is compressed past a certain threshold, potential energy is stored in the spring such that releasing the spring from compression causes the spring to extend, and when the spring is extended or stretched past the threshold, potential energy is stored in the spring such that releasing the spring from extension causes the spring to compress. By operating the spring(s) 702 around this threshold point, sufficient spring force (absent friction) is applied to transition the leaf 700 between the open and closed positions. In order to compensate for the loss of energy due to friction, the spring-based leaf drive mechanism may comprise an actuator or motor that is configured to add energy to the spring system. For example, an actuator may be coupled to the spring such that it applies additional compression or extension force to the spring to initiate spring movement from a stationary state and/or replenish energy lost in the spring system due to friction or other energy loss mechanisms. In some variations, the latch 706 may be configured to retain the leaf 700 at a position where the potential energy stored in the spring(s) is at a maximum and/or when the potential energy stored in the spring(s) is at a minimum (i.e., zero), and/or at any point therebetween (i.e., where part of the energy in the spring(s) is stored in the spring as potential energy and part of the energy is released as kinetic energy that moves the spring(s) at a non-zero velocity). For example, the latch may be configured to capture and retain the leaf when the leaf is at an extremum where the spring velocity is zero, and/or may be configured to capture and retain the leaf when the leaf is not at an extremum, where spring velocity is not zero.

Some spring systems of a leaf drive mechanism may comprise two sets of opposing springs, where the opposing springs are attached to opposite sides of a movable mass, and the resonant motion of the mass between the springs may drive the leaf between the open position and closed position. In some variations, the spring system may comprise a first spring (or set of springs) that may apply a force on the mass that moves the leaf in a first direction towards the open position and a second spring (or set of springs) that may apply a force on the mass that moves the leaf in a second direction opposite to the first direction, where the second direction is towards the closed position. One or more latches may be located such that the leaf (and/or an additional mass, and/or a support frame to which the leaf is attached) is captured and retained in the open position and/or the closed position. For example, a first latch may be located such that it is capable of capturing and retaining the movable mass such that the leaf is at the open position and a second latch may be located such that it is capable of capturing and retaining the movable mass such that the leaf is at the closed position. In some variations, the latch may be configured to retain the movable mass at a position where the potential energy stored in the spring(s) is at a maximum and/or when the potential energy stored in the spring(s) is at a minimum (i.e., zero), and/or at any point therebetween. For example, the latch may be configured to capture and retain the movable mass when the leaf is at an extremum where velocity is zero, and/or may be configured to capture and retain the leaf when the leaf is not at an extremum, where velocity is not zero.

Figure 7C:
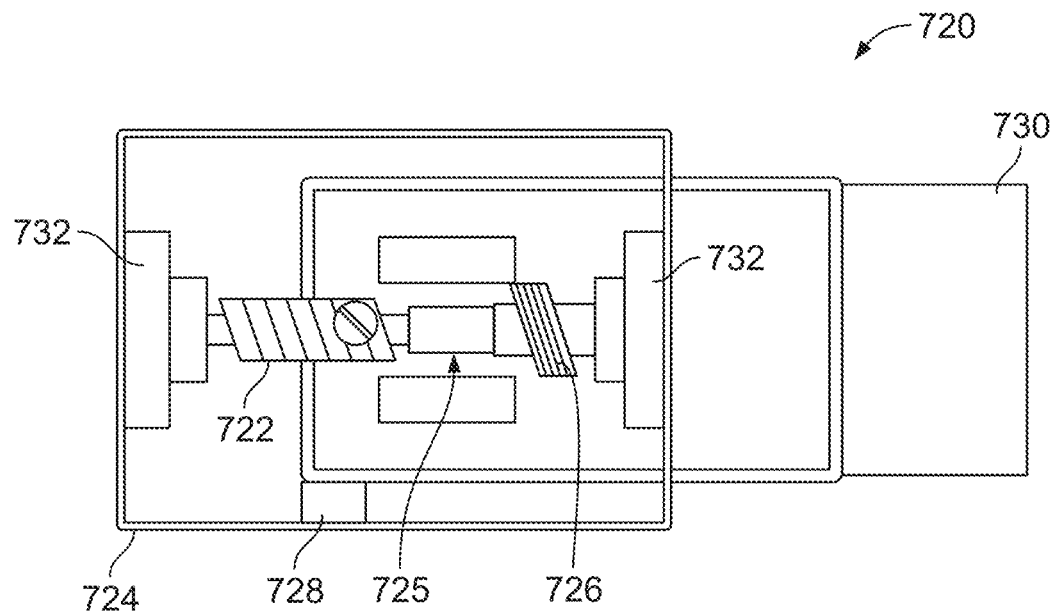
FIG. 7C is a schematic depiction of another variation of a spring-based leaf drive mechanism.
Figure 7D:
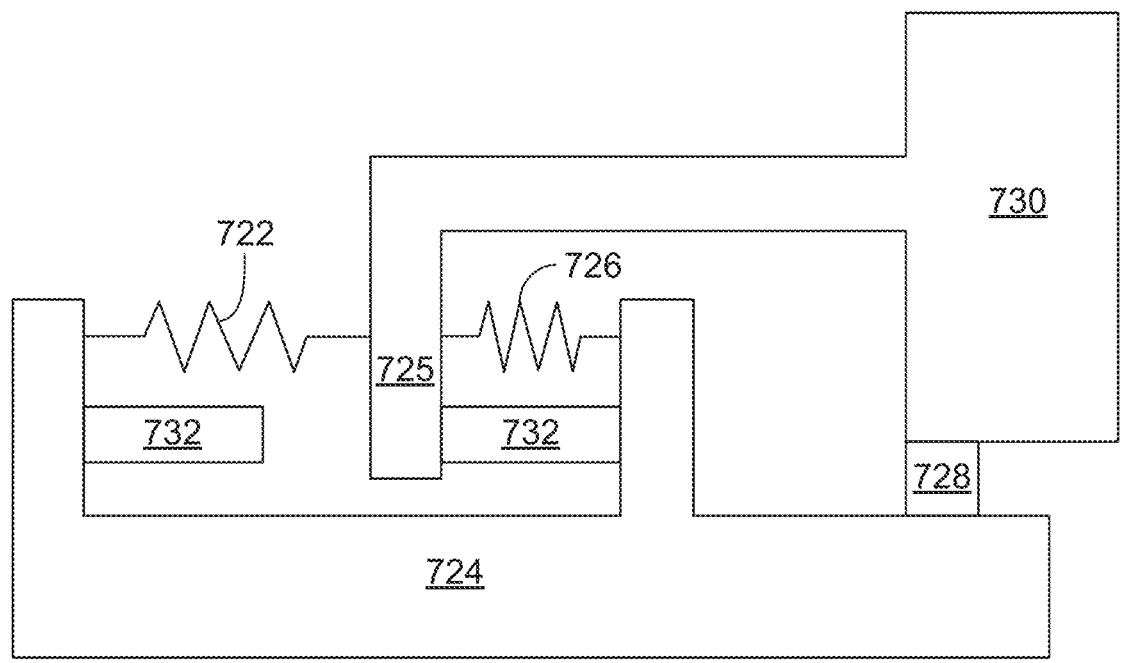
FIG. 7D is an alternate view of the spring-based leaf drive mechanism of FIG. 7C.

Alternatively or additionally, some spring-based leaf drive mechanisms of a collimator may comprise an actuator that is coupled to at least one of the springs and/or the movable mass, where the actuator is configured to compress and/or expand at least one spring to replace the energy lost in the system due to friction and/or latching at a non-zero velocity. For example, an actuator may act to compress a first spring when the leaf is in the closed position, so as to ensure the first spring has sufficient stored energy to fully transition the leaf to the open position. In some variations, an actuator may be configured to add energy to the spring mechanism by applying a force directly to the movable mass as it is moving. In some variations, the actuator may be configured to apply force to the spring at the resonant frequency of the spring system and/or in phase with the oscillation of the spring to add energy to the spring system. For example, the actuator may be configured to apply force to the spring when the sum of the potential and kinetic energy is below a usable limit (e.g. zero), as would be required to add energy into the system to prepare it for use from an initial startup state or to recover from an error. Alternately, the actuator may be configured to apply force to the spring at the moment when all of the spring energy has been converted to kinetic energy and/or during compression of the spring in order to store more potential energy in the spring. Alternatively or additionally, an actuator may be configured to add energy to the spring mechanism when the mechanism is in the latched state, as depicted in FIGS. 7C and 7D and described below. In some variations, the actuator may act directly on the spring, and not on the movable mass.

One variation of a spring-based leaf drive mechanism comprising a spring system comprising a pair of springs is depicted in FIGS. 7C and 7D. The spring-based leaf drive mechanism 720 may comprise a stationary support 724, a movable support 725 of a selected mass to which the leaf 730 may be attached, a first spring 722 attached between the stationary support and the movable support, a second spring 726 attached between the stationary support and the movable support, a latch 728 configured to capture and retain the leaf and/or movable support, and one or more actuators 732 (e.g. piezo actuators) coupled between the springs and the stationary support. In some variations, the one or more actuators may be coupled to one or both of the springs. The latch 728 may be located such that it is capable of capturing the leaf 730 and/or movable support 725 to retain the leaf in the open position. The actuator 732 may be a piezo pusher which may further compress the second spring 726 to restore any energy lost due to friction and/or latching.

Different types of actuators may be used in a spring-based leaf drive mechanism to add energy back into the spring system. Some actuators may act by directly applying force onto a spring, while some actuators may act by directly applying force onto the movable mass, while still some other actuators may act by directly applying force to a leaf and/or leaf support structure. Some actuators may be configured to fully compress and/or expand a spring (e.g. to initiate motion of non-moving leaf, such as when the collimator first starts up or powers on, or when the controller has detected an error in the motion of the spring system and resets the springs to an initial, non-moving state), while other actuators may be configured to apply a small amount of energy to initiate spring motion and may apply a force at the resonant frequency and in-phase with the oscillation of the spring system until the motion amplitude of the movable mass is at a desired amplitude, i.e., sufficient to move the leaf to either the open position or the closed position. Multiple actuators with different force capacities and frequencies may be used with any of the spring-based drive mechanisms described herein. Examples of actuator systems that may be used with a spring-based leaf drive mechanism may comprise electromagnetic actuators, voice coil actuators, solenoid actuators, rotary actuators, linear actuators, pneumatic actuators, hydraulic actuators, ultrasonic actuators, combustive actuators, piezo actuators, electrostatic actuators and the like. In some variations, an actuator system may comprise a latch or brake system. For example, an electromagnet (and/or in conjunction with a permanent magnet) may be configured to both attract and repel the moving mass, to both capture and retain the leaf and/or moving mass at a particular location and also to apply energy back into the system as needed. Similarly a pneumatic piston may be configured to push or pull the moving mass to retain the leaf at a particular location and also to apply energy back into the system as needed. Alternatively or additionally, a slotted link mechanism (e.g., a scotch yoke) may be used in conjunction with an electric motor or a rotary solenoid actuator to capture and retain the leaf and/or moving mass at a particular location and also apply energy back into the system as may be desired.

Various latches for capturing and retaining a movable mass and/or leaf are described below. In some variations, a latch may capture and retain a movable mass and/or leaf by applying a force that opposes the direction of movement of a leaf. For example, a latch may apply a frictional force to the leaf, and/or apply a torque force that opposes the direction of leaf movement. Examples of such latches may include a notch and following wheel, a releasable, overrunning clutch, and/or a capstan clutch (e.g., a torsion spring wrapped around axle). For example, a latch may comprise a releasable roller or "sprag" clutch to capture the leaf upon motion reversal. A clutch may be designed to utilize capstan friction, in which a wire or thread is wrapped around a capstan that is coupled to the moving mass so that the capstan rotates during motion (e.g. with a rack and pinion assembly). Tensioning the wire or thread may exponentially increase the rotational friction on the capstan, halting its motion. In some variations, a latch may have a retention feature and the moving mass and/or leaf may have a corresponding retention feature and the latch may capture and retain a movable mass and/or leaf via engagement of these retention features. For example, the moving mass and/or leaf and the latch may each have corresponding notches or protrusions that engage when the latch is transitioned to the locked state. Other systems may rely upon a positional feature on the moving mass (e.g. a notch, detent, or peg hole) to engage a pin, roller, etc. Still other latch variations may comprise electromagnets, where a corresponding magnet or ferromagnetic material may be placed on the moving mass and/or leaf, where the latch electromagnets may be used to capture and hold the moving mass and/or leaf such that the leaf is retained at the extremums. Some latch mechanisms may include a spiral voice coil. Other latches may function as a brake, for example, a friction brake may be applied normal or orthogonal to the direction of leaf travel to stop and hold the leaf using frictional forces. Such brake-style systems may be configured to apply force at any desired location on the movable mass and/or leaf, and does not require precise alignment of a notch and detent, for example. The friction brake might be a pneumatic, electromagnetic, piezo-restrictive mechanism. Since a brake does not require precise alignment with a notch or protrusion at a certain location in the movable mass and/or leaf, there may be greater variability in the position where the leaf is retained. This may allow the brake to maintain the position of the leaf even when the various components of the spring-based drive mechanism are not precisely aligned, and therefore may be able to tolerate any unexpected or unintentional mechanical perturbations to the system.

Figure 8A:
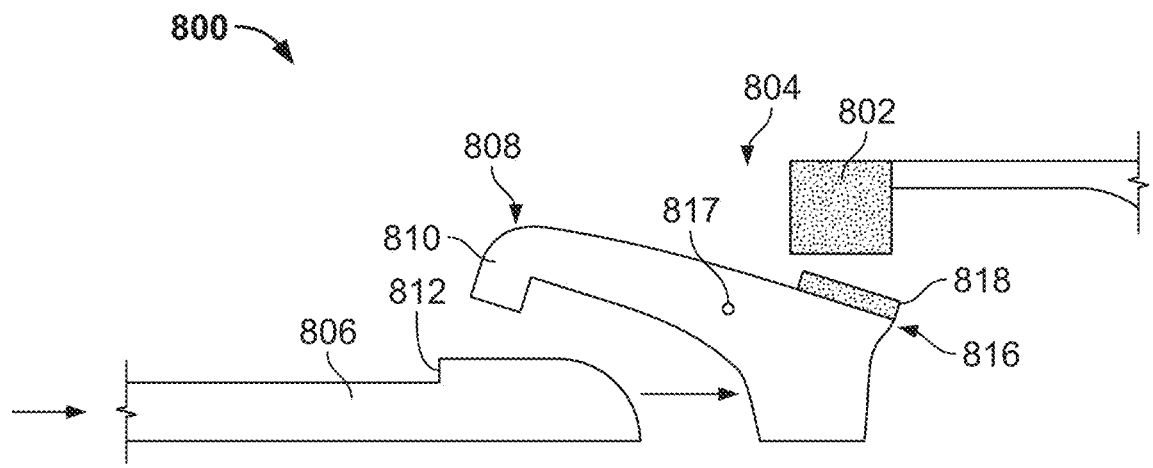
FIGS. 8A-8C schematically depict one variation of a latch that may be used with a spring-based leaf drive mechanism.
Figure 8B:
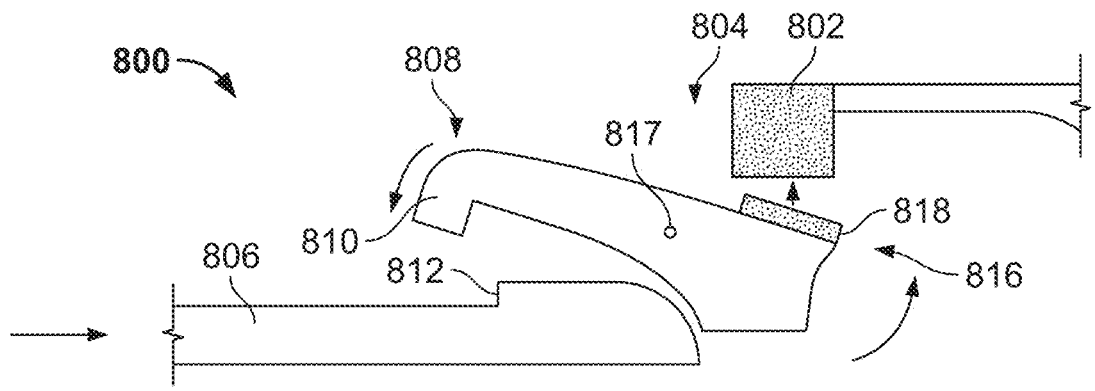
Figure 8C:
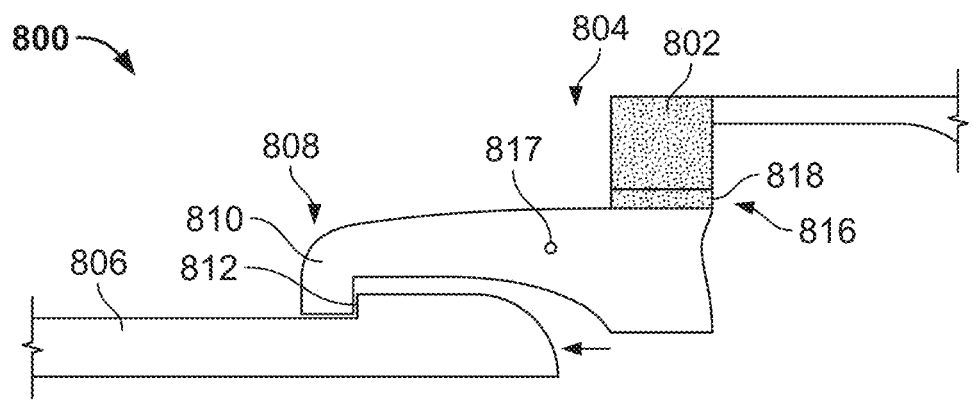

One variation of a positional latch comprising an electromagnet (e.g., a latch in which engagement with the movable mass and/or leaf relies on a positional alignment between the latch and the movable mass and/or leaf) is depicted in FIGS. 8A-C. Such latch mechanism may be used with any of the collimator leaf drive mechanisms described herein. As shown in FIG. 8A, a latch mechanism 800 may comprise an electromagnet 802 and a control arm 804 that selectively engages a portion of a leaf 806 by pivoting downward to engage a portion of the leaf 806 when the leaf moves into the control arm (e.g., an extremum). The downward motion of the control arm may be caused by leaf motion and contact, energizing of the electromagnet, or a combination of both. The electromagnet may remain energized so as to retain the control arm in this downward, latched configuration, and de-energized or reverse energized (e.g., to have a polarity that repels the control arm) to release the leaf. A first end 808 of the arm 804 may have a leaf engagement structure 810 that corresponds to a catch or an engagement structure 812 on the leaf 806, and the second end 816 of the control arm 804 may comprise a magnetic material. For example, the leaf engagement structure 810 may be a hook and the catch 812 may be a groove or ledge sized and shaped to be engaged by the hook. In some variations, the catch may include a roller which may help to facilitate release of the leaf. The shape (e.g., slope, extent, or curvature) of the catch surface may be adjusted to make it easier or harder to release the roller. The portion of the leaf 806 that has the catch 812 may be any structure that moves in concert with the leaf, for example, the radiation-blocking portion of the leaf, or the support structures associated with the leaf. The latch mechanism 800 may have three configurations, each of which are depicted in FIGS. 8A-C. FIG. 8A depicts the latch mechanism 800 in the open configuration as a portion of the leaf 806 moves to the right. In this configuration, the polarity of the electromagnet 802 may be such that it repels a ferromagnetic plate 818 on the second end 816 of the control arm 804, which may help to keep the first end of the arm 808 in an upward or higher position. In FIG. 8B, the leaf portion 806 contacts the control arm 804, which may cause it to rotate around the pivot point 817. This may cause a catch on the first end 808 of the control arm 804 to drop down, and a ferromagnetic plate 818 on the second end 816 of the control arm to move upward. The polarity of the electromagnet 802 may be changed such that it attracts the ferromagnetic plate 818. In FIG. 8C, the electromagnet 802 has captured the ferromagnetic plate 818, holding the catch in the down position, capturing the leaf. To release the leaf, the electromagnet 802 may be energized with an opposite polarity, expelling the ferromagnetic plate 818 away from the electromagnet 802 and pivoting the control arm 804 such that the first end 808 is raised, thereby releasing the leaf 806.

Some variations of a latch or actuator system of a collimator leaf drive mechanism may comprise a slotted link (e.g., scotch yoke) mechanism in combination with a rotary actuator or motor, which may be configured to latch the leaf in both the open and closed positions. The yoke may be attached to the movable mass of the spring-based drive mechanism, and a rotary actuator may be used to drive the pin in the yoke with an eccentric (by which the pin is offset by some radius from the axis of the rotary actuator). At the extremes of travel, the rotary actuator may have infinite mechanical advantage over the spring system, so no force would be required to hold the moving mass at the extremum. Rotating the actuator may release the spring system. The rotary actuator may be used to add energy to the system by applying force in the direction of motion as the leaf transitions from one extremum to the other (e.g., between open and closed positions). For example, the rotary actuator may be used to add energy to the spring system if it is capable of moving the pin faster than the spring system can move the yoke. The pin may then apply an accelerating force to the spring mass. As with a linear voice-coil latch mechanism, the rotary actuator may be operated at the resonant frequency of the spring system to start the system from a de-energized state. Some variations may comprise a rotary solenoid with a 180 degree range of motion, while other variations may comprise a brushless DC motor with a range of motion that is more than 180 degrees. The shape of the slot within the scotch yoke may be adjusted to better match the motion of the spring system to the actuator characteristics, or to help fine-tune the latch and release characteristics of the system or to adjust the mechanical advantage of the actuator as a function of throw and/or to better match actuator torque with the desired speed characteristics. For example, a shortened slot that does not allow the actuator to reach a full 180 degree rotation may bias the system towards the unlatched configuration (e.g., where the leaf is able to be moved by the spring system). Alternatively or additionally, a small detent in the shape of the slot may bias the system towards the latched configuration (e.g., where the leaf is not movable by the spring system). Slot surfaces that are curved or otherwise not perfectly vertical may be used to accommodate rotary motions that are not at a constant velocity. In some variations, this may be useful to help facilitate latching the leaf in a closed or open position, since the rotary actuator will need to accelerate and decelerate to enable latching at the extremums. In some variations, the rotary actuator may be a rotary solenoid, since the latch may not require a full 360 degree rotation. In some variations, the actuator may be biased towards release (thus requiring a small holding torque to latch in position) by reducing the range of motion to slightly below a full 180 degrees.

One variation of a collimator leaf drive mechanism of a multi-leaf collimator that may be disposed in the beam path of a radiation source may comprise a spring system (such as a spring resonator, including but not limited to, any of the spring resonators described above) and an actuator system that includes a scotch yoke that selectively retains the leaf in either the open or closed position. The actuator system may comprise a leaf shaft having a slot, a motor, a roller disposed within the slot, and a crank that couples the motor and the roller such that activation of the motor causes the roller to rotate with the slot. The spring system may have one or more springs disposed along the leaf shaft which may provide a longitudinal force along the axis of the leaf shaft to move the leaf between a first location and a second location. The first location may be an open position (or a closed position) while the second location may be a closed position (or an open position). The spring system may provide the motive force for translating the leaf between the first and second locations, while the actuator system may selectively retain the leaf in the first location and the second location. Optionally, the actuator system may also add energy to the spring system to compensate for the energy lost due to frictional forces and/or to provide sufficient energy to the spring system to accelerate the spring motion from a non-moving state to a desired target speed so that enough kinetic energy is provided to transition the leaf between the first and second locations. For example, the actuator system may add potential energy into the spring system by compressing the spring(s) while retaining the leaf in either the first location or the second location. The potential energy may be translated into kinetic energy that is sufficient to transition the leaf from one location to another. Whether spring forces or the actuator forces dominate the motion of the leaf may depend on the location of the roller within the slot, along with the geometry of the slot (e.g., radius of curvature, length and location of curved or straight regions, etc.), as described in the examples below.

Figures 11A, 11B:
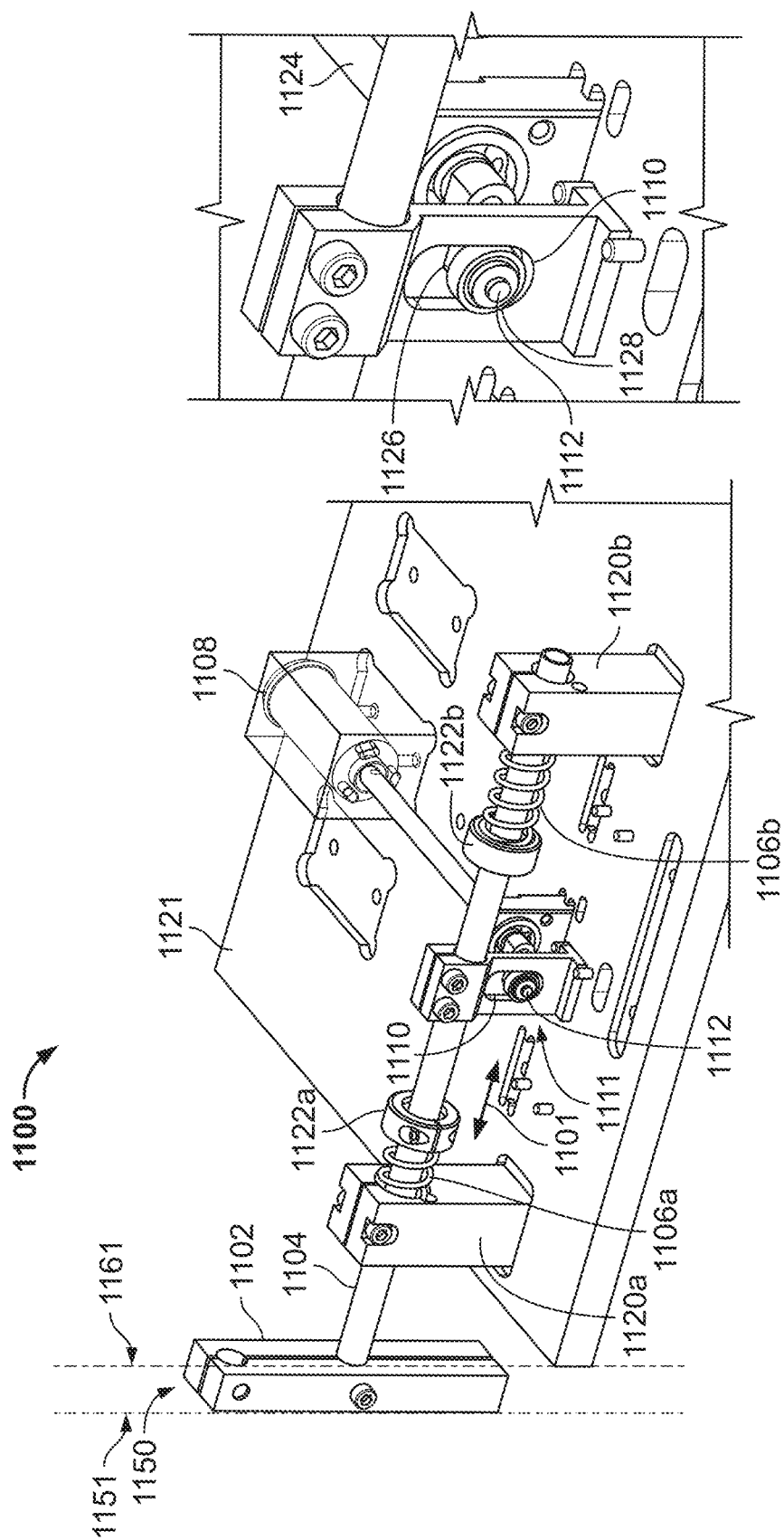

FIGS. 11A-11F depict one example of a collimator leaf drive mechanism comprising a spring system and an actuator system that includes a slotted-link or scotch yoke mechanism. The location and movement of a collimator leaf 1102 (which is represented by a rectangular block) may be driven by a spring system comprising a first spring 1106a and a second spring 1106b located along a leaf shaft 1104 and an actuator system comprising a slotted link mechanism (e.g., scotch yoke 1111) and a motor 1108. The sum of the translational forces (i.e., that move the shaft longitudinally as indicated by arrow 1101 in FIG. 11A) applied by the spring system and the actuator system may move the leaf 1102 between a first location 1150 and a second location 1160, and retain the leaf at either of those locations as may be desired. In the first location 1150 (which is depicted in FIG. 11A), the leaf 1102 may substantially or entirely obstruct a radiation path that is represented by the boundaries 1151, 1161, and in the second location 1160 (which is depicted in FIG. 11E), the leaf 1102 may not obstruct the radiation path. FIG. 11C depicts an intermediate configuration as the leaf 1102 moves from the first location 1150 (a leaf closed configuration) to the second location 1160 (a leaf open configuration). The scotch yoke 1111 may be attached to the leaf shaft 1104 and may comprise a slot 1110 located on a plate that is fixedly attached to the leaf shaft 1104, a roller 1112 disposed within the slot 1110 and a motor 1108 that rotatably translates the roller within the slot 1110. Depending on the location of the roller 1112 within the slot 1110, the spring system forces may cause the leaf 1102 to translate between the first and second locations, or the actuator system may oppose the spring forces and retain the leaf at either the first location 1150 or the second location 1160, as may be desirable. As depicted in FIG. 11A, the leaf shaft 1104 may be slidably retained by two shaft mounting blocks 1120a, 1120b. The shaft mounting blocks 1120a, 1120b, may each have a lumen therethrough, and the blocks may be fixably mounted on a base 1121 such that the lumens of the mounting blocks are aligned and the leaf shaft 1104 may extend through the lumens. The first and second springs 1106a, 1106b may be mounted to the leaf shaft 1104 between the shaft mounting blocks 1120a, 1120b and the first and second spring blocks 1122a, 1122b, respectively. The first and second spring blocks 1122a, 1122b may be fixedly attached to the leaf shaft 1104. In this variation, where the springs 1106a, 1106b are used in compression, the ends of the springs may not be attached to either the shaft mounting blocks or the spring blocks. In some variations, one of the ends of the springs may be attached to the spring block (or shaft mounting block), while the other end of the springs may be free from attachment. In other variations, where the springs may be used in tension, both ends of both of the springs 1106a, 1106b may be attached to the spring block and the shaft mounting block. For example, one end of the first spring 1106a may be attached the first spring block 1122a and the opposite end of the first spring 1106a may be attached to the first mounting block 1120a. The second spring 1106b may be similarly attached to the leaf shaft. While the spring blocks 1122 are depicted as rings that circumscribe the leaf shaft, it should be understood that spring blocks may have any other shape that may or may not at least partially circumscribe the leaf shaft. For example, a spring block may be a protrusion on the shaft to which the springs may be attached, and/or the springs may be welded, soldered, and/or adhered to the leaf shaft without any additional mount structure. The springs 1106 are depicted as coil-shaped springs that circumscribe the leaf shaft 1104, but it should be understood that in other types of springs may be included, such as torsion bars, torsion springs, compression springs, etc., which may or may not circumscribe the leaf shaft.

Figure 12A:
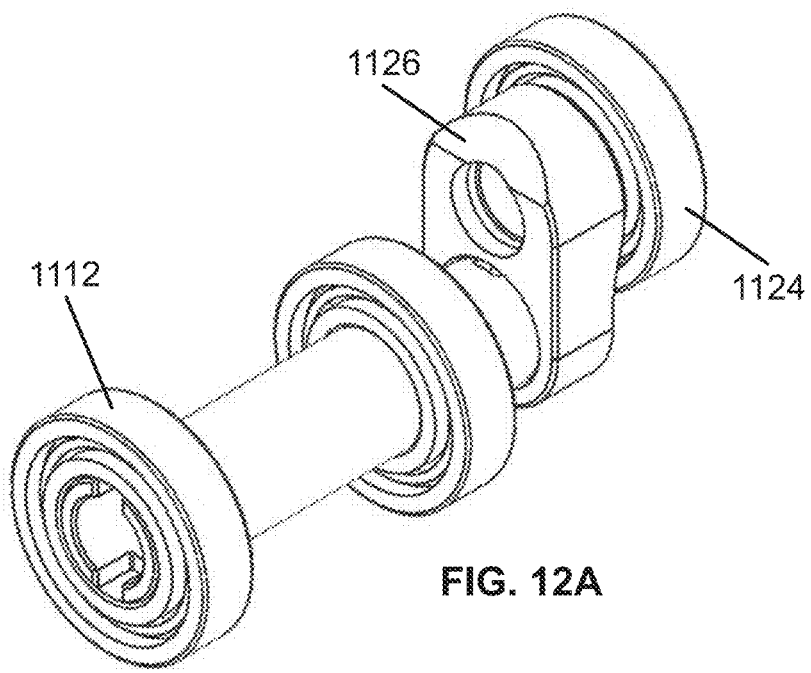
FIG. 12A is a perspective component view of the coupling between the roller, the crank, and the distal-most end of the motor shaft.
Figure 12B:
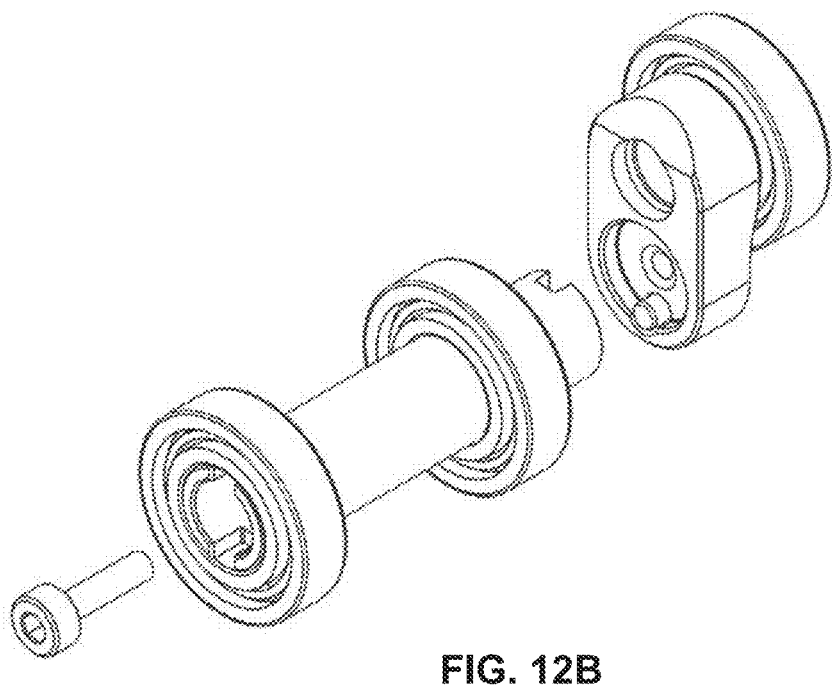
FIG. 12B is a partial exploded view of the assembly in FIG. 12A.
Figure 12C:
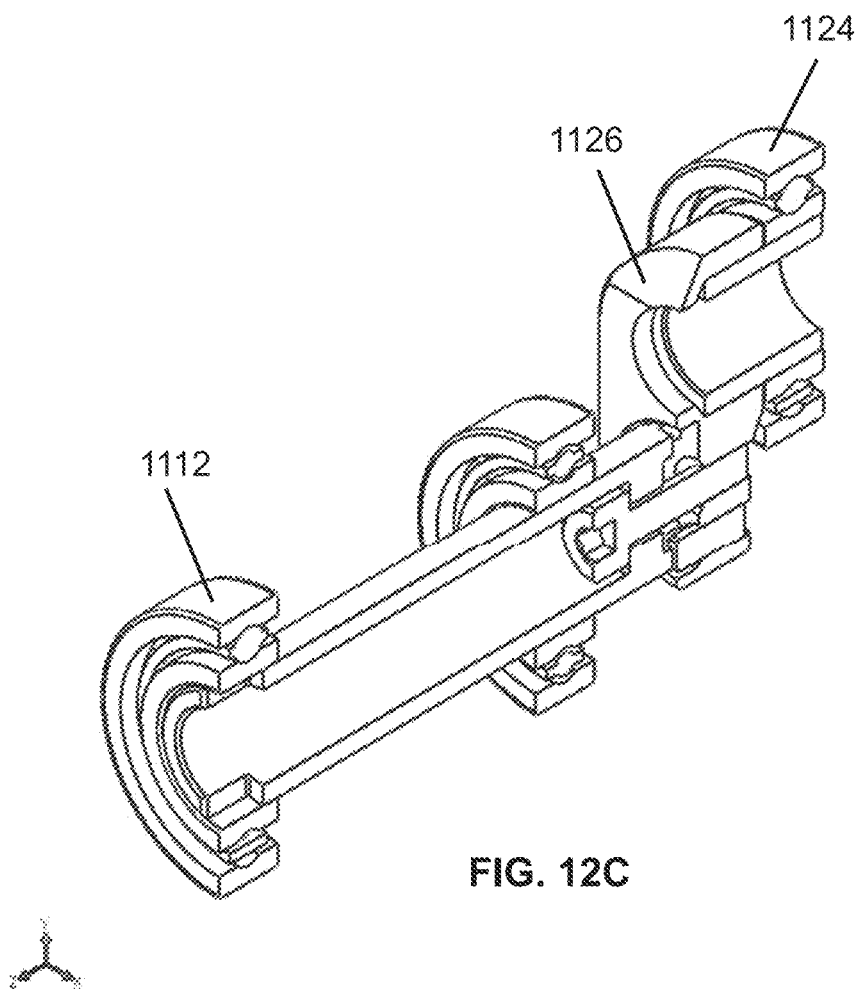
FIG. 12C is a cross-sectional view of the assembly of FIG. 12A.

FIGS. 11B, 11D and 11F are close-up depictions of the position of the scotch yoke mechanism when the leaf 1102 is retained in the closed configuration (i.e., at the first location 1150), in transit from the closed configuration to the open configuration, and retained in the open configuration (i.e., at the second location 1160), respectively. The motor 1108 of the actuator system is coupled to the roller 1112 by a motor shaft 1124 and a crank 1126, such that rotation of the crank rotates the roller 1112 within the slot 1110. FIG. 12A is a perspective component view of the coupling between the roller 1112, the crank 1126, and the distal-most end of the motor shaft 1124, FIG. 12B is a partial exploded view of the roller, crank and motor shaft of FIG. 12A, and FIG. 12C is a cross-sectional view of the coupling between the roller, crank and motor shaft of FIG. 12A. In the variation depicted in FIGS. 11A-11F, the motor 1108 rotates the crank 1126 in a clockwise direction to transition the leaf from the closed configuration to the open configuration. The slot 1110 may have one or more curved regions to allow the leaf to move and transition between the first and second locations, as well as to retain the leaf at either of these locations, as desired. For example, the slot 1110 may have a first stop region 1128 and a second stop region 1130. When the roller 1112 is located at either of these regions, the spring forces from the spring system along the lateral direction (indicated by arrow 1101) are opposed by the roller against the stop regions 1129, 1130 in the slot. This may prevent the spring forces from laterally moving the leaf shaft, thereby retaining the leaf at either the first or second locations, which may remove kinetic energy from the system. That is, when the roller 1112 is located at the first stop region 1128, the first spring 1106a may be compressed and/or second spring 1106b may be extended such that potential energy is added to the spring system that is at least equal to (and may optionally be greater than) the spring forces that were lost (e.g., due to friction, etc.) during the motion of the springs and the leaf shaft. Similarly, when the roller 1112 is located at the second stop region 1130, the second spring 1106b may be compressed and/or the first spring 1106a may be extended such that potential energy is added to the spring system that is at least equal to (and may optionally be greater than) the spring forces that were lost during the motion of the springs and the leaf shaft. The radius of curvature and/or the angular sweep of the first stop region 1128 and the second stop region 1130 may be selected such that the roller 1112 may traverse the curve(s) in that region while still providing a sufficient opposition force to the spring system forces to retain the leaf in either the first location or the second location.

Figure 13A:
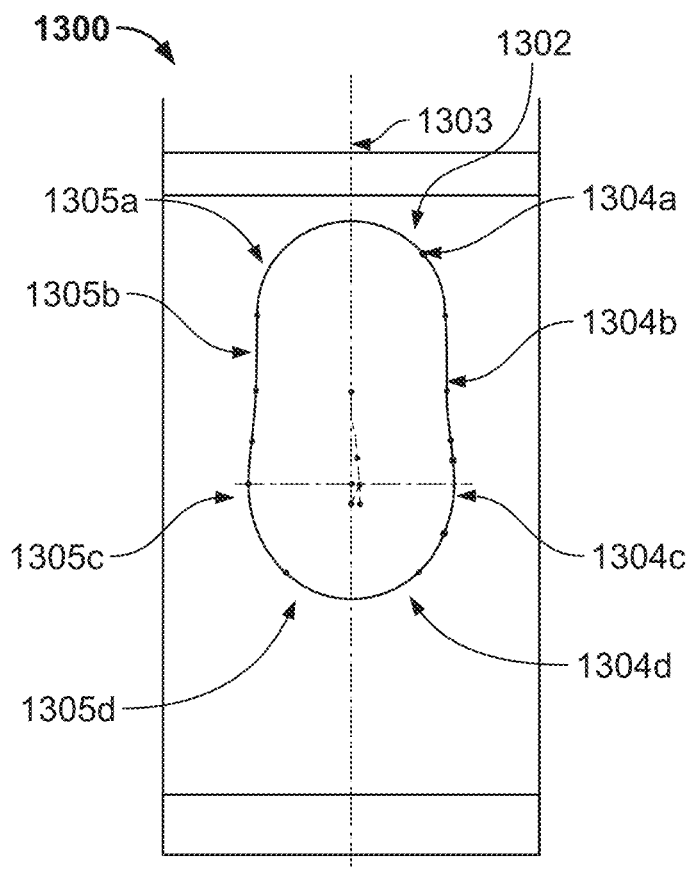
FIGS. 13A-13B depict one variation of a slot of a scotch yoke mechanism.
Figure 13B:
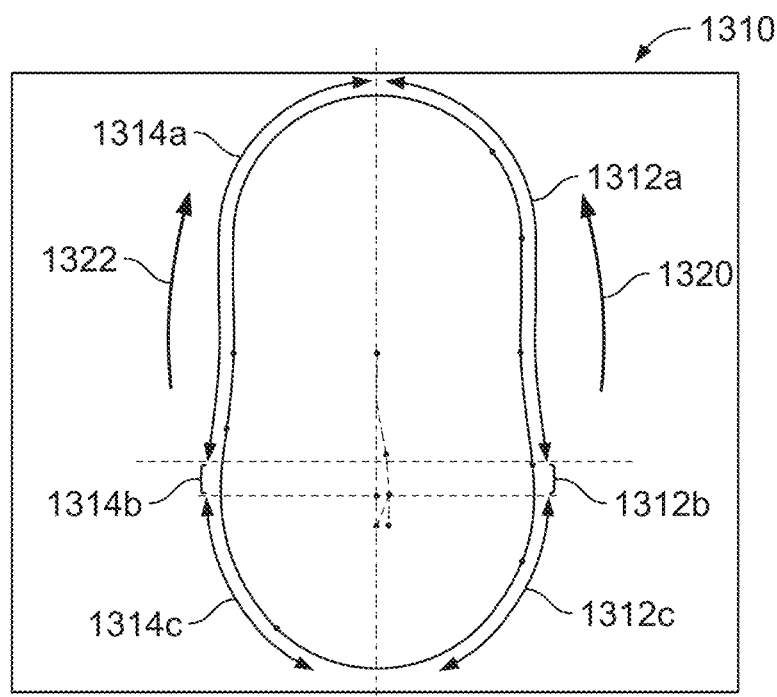

One variation of a slot shape that may be used in a slotted link or scotch yoke mechanism is depicted in FIGS. 13A and 13B. FIG. 13A depicts a slotted plate 1300 that may be attached to a leaf shaft within which a roller may translate as part of a scotch yoke mechanism (for example, as depicted and described above in FIGS. 11A-11F). The slotted plate 1300 may have a slot 1302 with one of more curves that have different radii of curvature. For example, one side of the slot 1302 may have curved segments with four different radii of curvature. In the variation depicted in FIGS. 13A-B, the slot may be bilaterally symmetric along a vertical axis of symmetry 1303 with the same curved segments on the opposite side of the axis of symmetry. A first segment 1304a may have a radius of curvature of about 5 mm (e.g., 5.05 mm), a second segment 1304b contiguous with the first segment may have a radius of curvature of about 15 mm (e.g., about 15.3 mm), a third segment 1304c contiguous with the second segment may have a radius of curvature of about 6 mm (e.g., about 6.5 mm), and a fourth segment 1304d contiguous with the third segment may have a radius of curvature of about 5 mm (e.g., about 5.05 mm). In this variation, when the roller is located in the first and second segments, the motion of the leaf is dominated by the forces applied by the spring system, and the leaf may move to translate between the closed configuration and the open configuration (e.g., the first location and the second location). When the roller is located in the third and fourth segments, the leaf is held stationary in either the closed configuration or the open configuration. As the roller translates within the slot in a counterclockwise direction and moves from the first segment 1304a to the fifth segment 1305a on the other side of the axis of symmetry 1303, the motor to which the roller is coupled may introduce additional rotation energy to the roller to compensate for energy losses (e.g., mechanical energy losses) due to friction. The slot may comprise a sixth segment 1305b, a seventh segment 1305c, and an eighth segment 1305d that may be similar to (e.g., mirror-symmetric) to the second segment 1304b, third segment 1304c, and fourth segment 1304d, respectively. The curvature of the first segment 1304a and the curvature of the fifth segment 1305a may be selected such that the roller can smoothly translate between the two sides of the slot, and/or may reduce the likelihood that the roller loses contact with the edges of the slot as it translates between the first and fifth segments. In some variations, the curvature of the first segment and the curvature of the fifth segment are such that they facilitate the movement of a roller from one side of the slot to the other, so that even if the roller loses contact with the edge of the slot, the distance travelled by the roller while it is not in contact with the slot is relatively short as compared to the overall distance travelled by the roller. FIG. 13B is a depiction of the various curves of a slot 1310 (which may be the same as, or similar to, the slot 1302), where the various curves may correspond to different modes of operation. The slot 1310 may be bilaterally symmetric about a vertical axis of symmetry, and one side of the slot may have a first curved region 1312a, a second curved region 1312b continuous with the first curved region, and a third curved region 1312c contiguous with the second curved region. There may be similar corresponding curves on the opposite side of the slot 1310: a fourth curved region 1314a that corresponds with the first curved region 1312a, a fifth curved region 1314b that corresponds with the second curved region 1312b, and a sixth curved region 1314c that corresponds with the third curved region 1312c. The descriptions of the first, second and third curved regions below may apply to the fourth, fifth, and sixth curved regions. Although each side of the slot in this example has three curved regions, it should be understood that there may be any number of curved regions as may be desirable. Each of the curved regions may have curves of varying radii of curvature, or may have curves with a single radius of curvature. In variations where there may be multiple curves with multiple radii of curvature, the transition from one curve to the next may be continuous and smooth such that there are no abrupt, discontinuous or acute changes in the curvature. In some variations, the curvature of these regions may be shaped such that the roller maintains smooth contact with the edge of the slot. In variations where the roller may lift away from the edge of the slot (e.g., moves away from the edge of the slot), the curvature(s) may be shaped to promote a smooth transition as the roller comes back into contact with the edge of the slot. Curves that facilitate smooth transition(s) roller may help to limit the sound intensity as the roller comes back into contact with the slot edge. In particular, a roller may be most susceptible lifting away from the slot edge as it translates between the first curved region 1312a and the fourth curved region 1314a, at a top portion 1313 of the slot 1310. The top portion 1313 of the slot may comprise at least a portion of the first and fourth curved regions, which may connect to each other at an apex 1315. The top portion 1313 may have a curvature that facilitates smooth movement of the roller between the first curved region 1312*a* and fourth curved region 1314*a*, regardless of whether the roller maintains constant contact with the slot edge or lifts away from the slot edge as it moves in this region of the slot. In some variations, as the roller moves within the top portion 1313, the motor to which the roller is attached may add energy back into the system to compensate for various energy losses (e.g., mechanical losses such as friction). For example, the system is configured to introduce additional rotational energy to the roller as it moves across the apex 1315. When a roller of a scotch yoke or slotted link mechanism is located in the top portion 1313, the leaf may be in transit from one configuration to another (from open to closed, or closed to open), and may be moving at a speed such that this configurational change occurs within less than about 10 ms (e.g., less than about 6 ms, or less than about 4 ms). The spring system may provide sufficient motive force in this mode of operation. The actuator system may optionally provide additional motive force that constructively adds with the spring force. In some variations, the speed of movement may peak at the juncture between the first region 1312*a* and the fourth 1314*a* region (e.g., at the apex 1315), though in other variations, the speed of movement may be substantially the same as the roller moves within the top portion 1313. When the roller moves to the second curved region 1312*b*, the actuator system may provide a force that opposes the spring force sufficient to retain the leaf in either the open configuration (if the slot 1310 is used with the system depicted in FIGS. 11A-11F) or the closed configuration (if the slot 1310 is used in a system that has an opposite orientation to the system depicted in FIGS. 11A-11F). Rotationally translating the roller in the second curved region 1312*b* may not result in a corresponding lateral movement of the leaf and/or leaf shaft. This may provide a margin within which the motor of the actuator system can accelerate to the desired rotational speed with little or no lateral movement of the leaf. If the roller moves to the third curved region 1312*c*, the actuator system may further compress a first spring of the spring system and/or expand a second spring of the spring system, converting kinetic energy in the actuator system to potential energy in the spring system, thereby ensuring that the leaf is retained in either the open or closed configuration. In some variations, when the roller is stopped within this third curved region 1312*c*, a trailing edge of the leaf may be located further away from the boundary of the radiation beam path (in the case where the leaf is retained in the open configuration) or the trailing edge of the leaf may be located closer to the boundary of the radiation beam path (in the case where the leaf is retained in the closed configuration). As an example, arrow 1320 represents the movement of a roller within the slot as a leaf arranged as in FIGS. 11A-11E is transitioned from an open configuration to a closed configuration, and arrow 1322 represents the movement of the same roller as the leaf is transitioned from a closed configuration to an open configuration.

Figure 14A:
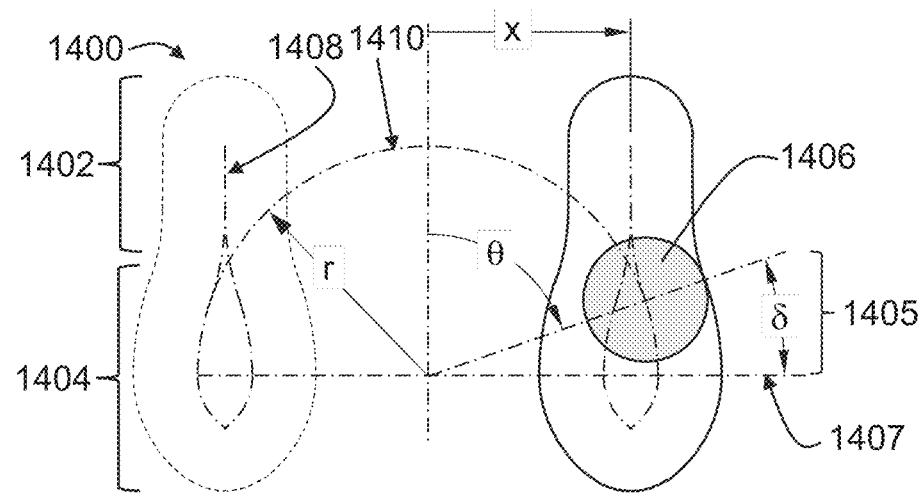
FIG. 14A depicts a variation of a slot of a scotch yoke mechanism.

Other slot shapes and geometries may be used in a slotted-link or scotch yoke mechanism. FIG. 14A depicts a slot 1400 having a top portion 1402 that has two straight segments that are parallel to each other connected with a curve with a constant radius of curvature and a bottom portion 1404 having a partial oval shape comprising arcs with varying radii of curvature. In the slot 1400, the bottom portion 1404 may be wider than the top portion 1402. The widened, variable radius of curvature region 1404 may provide a stable region 1405 (e.g., the portion of the slot where the scotch yoke mechanism supplies sufficient force to oppose the spring forces to retain the leaf in an open or closed configuration) that has an angular sweep of δ, which may be from about 5 degrees to about 20 degrees. The value of δ may be determined at least in part by the precision with which the motor that drives the roller 1406 can position the roller at a desired location in the slot. That is, the sweep angle δ may provide a margin of tolerance for the motor driving the roller. The path of the roller is represented by dotted lines 1408 and may be attained by a motor rotating the crank (not depicted here, but similar to the depiction in FIGS. 12A-12C) along the dotted lines 1410. The path 1410 in the stable region 1405 may be an arc that may match or approximate the radius r of the crank. The stable region may extend below the horizontal axis (i.e., |θ|>90°) in some variations. The stable region may be symmetric about a horizontal axis 1407, which may help to reduce the tendency of the roller to lose contact with the slot as it moves within the curvature of the slot.

Figure 14B:
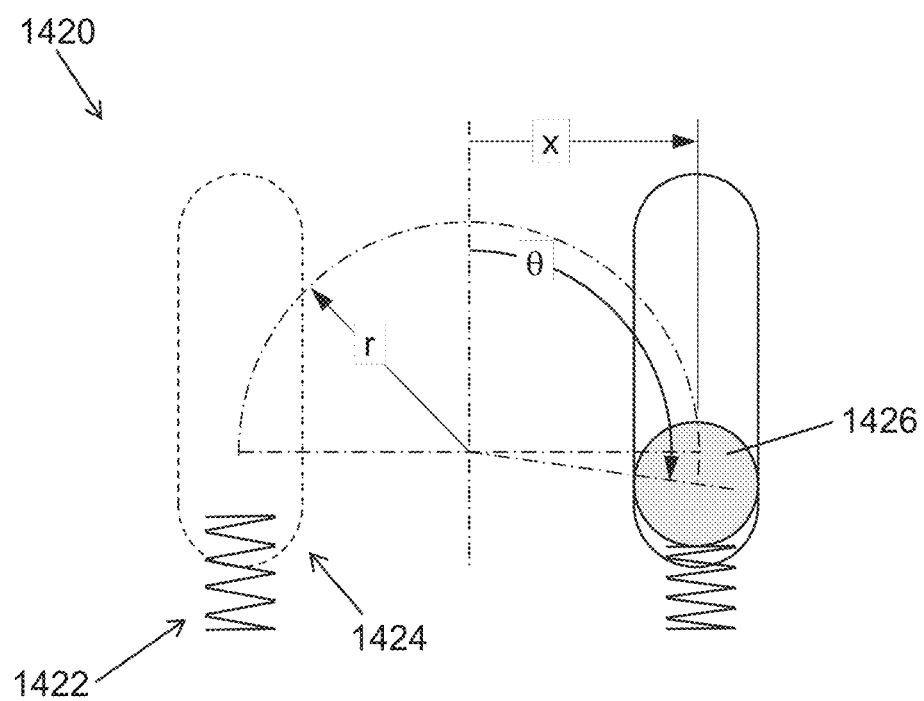
FIG. 14B another variation of a slot of a scotch yoke mechanism.

While the slot shape and geometry may have multiple curves with various radii of curvature, in some variations, the slot may have two straight parallel edges with two end curves with the same radius of curvature (so-called a straight slot). The stable region of a straight slot may be very short, and therefore, unstable, as a slight rotation or perturbation of the roller in either direction of the stable region will allow the spring system to cause translation of the leaf. As such, the stable region of a straight slot may be considered a "singularity point", since there is little or no margin of tolerance for a motor driving the roller such that any deviation from the "singularity point" allows the spring system to translate the leaf. One example is depicted in FIG. 14B. A scotch yoke or slotted link mechanism comprising a straight slot 1420 may optionally comprise a spring 1422 located within the bottom curve 1424. The spring 1422 may be a coil spring (as depicted in FIG. 14B), or any other type of spring. The spring 1422 may be sized so that its positive angular stiffness imparted to the crank (not depicted here, but similar to the depiction in FIGS. 12A-12C) may counteract the negative angular stiffness in the scotch yoke when loaded by the spring system at the singularity point. The spring load of the spring system may create an angular stiffness at θ=±90°. The spring 1422 may engage with positive stiffness for |θ|>90°.

Figure 15A:
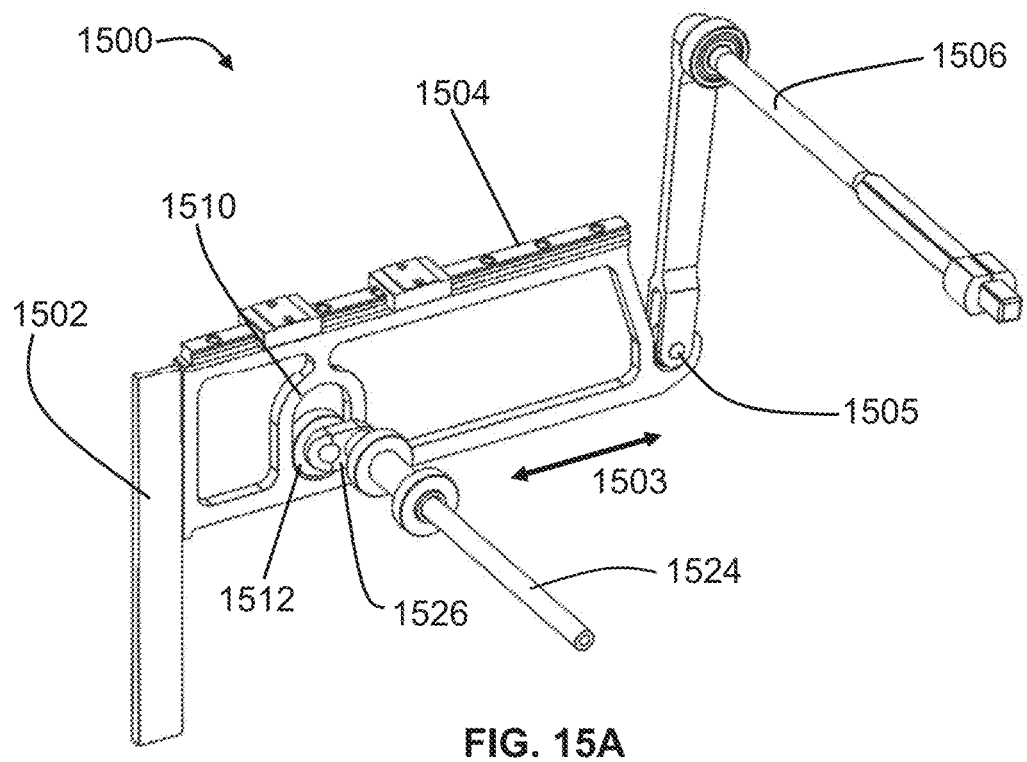
FIG. 15A is a perspective component view of one variation of a collimator leaf drive mechanism comprising a spring system and an actuator system including a scotch yoke or slotted link mechanism.
Figure 15B:
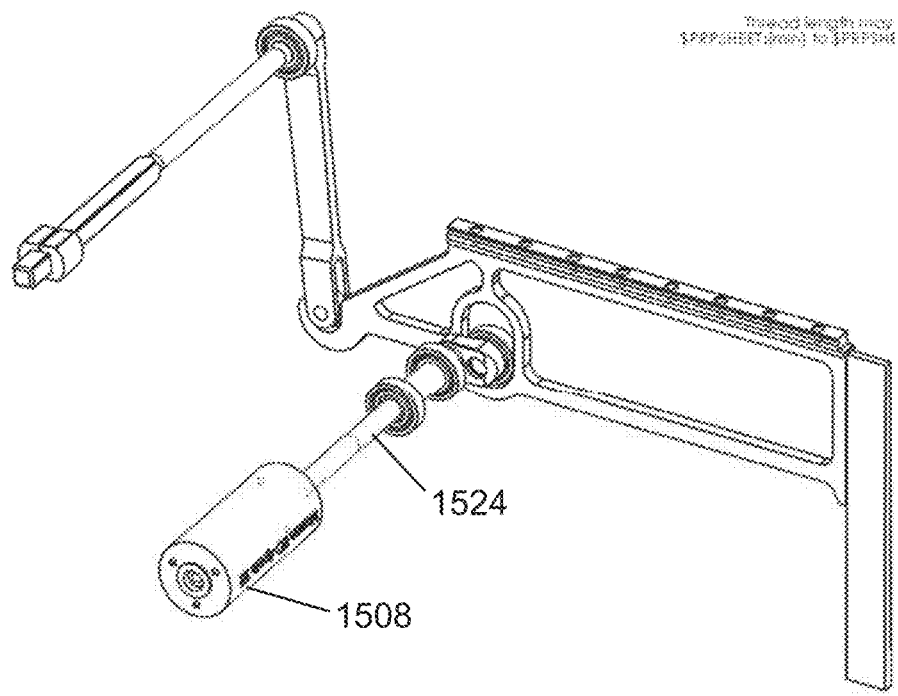
FIG. 15B is an alternate perspective component view of the leaf drive mechanism of FIG. 15A.
Figure 15C:
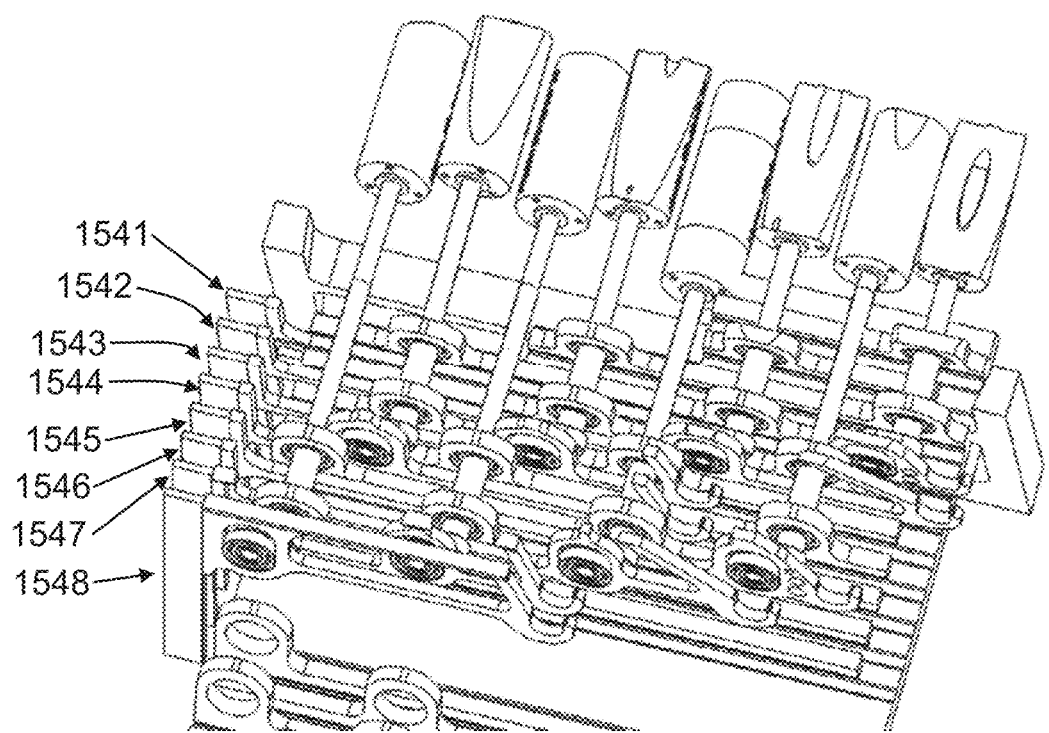
FIG. 15C is a top perspective view of a plurality of collimator leaf drive mechanisms assembled/packaged together.
Figure 15D:
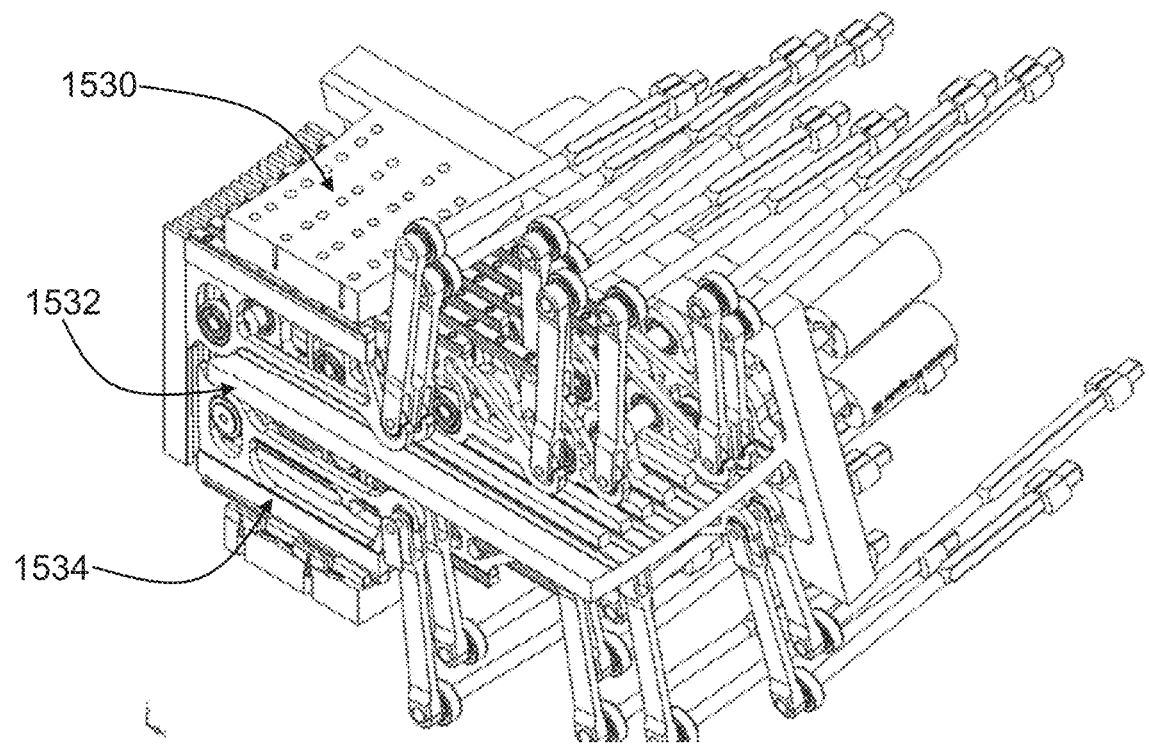
FIG. 15D depicts a side perspective view of the plurality of collimator leaf drive mechanisms of FIG. 15C.
Figure 15F:
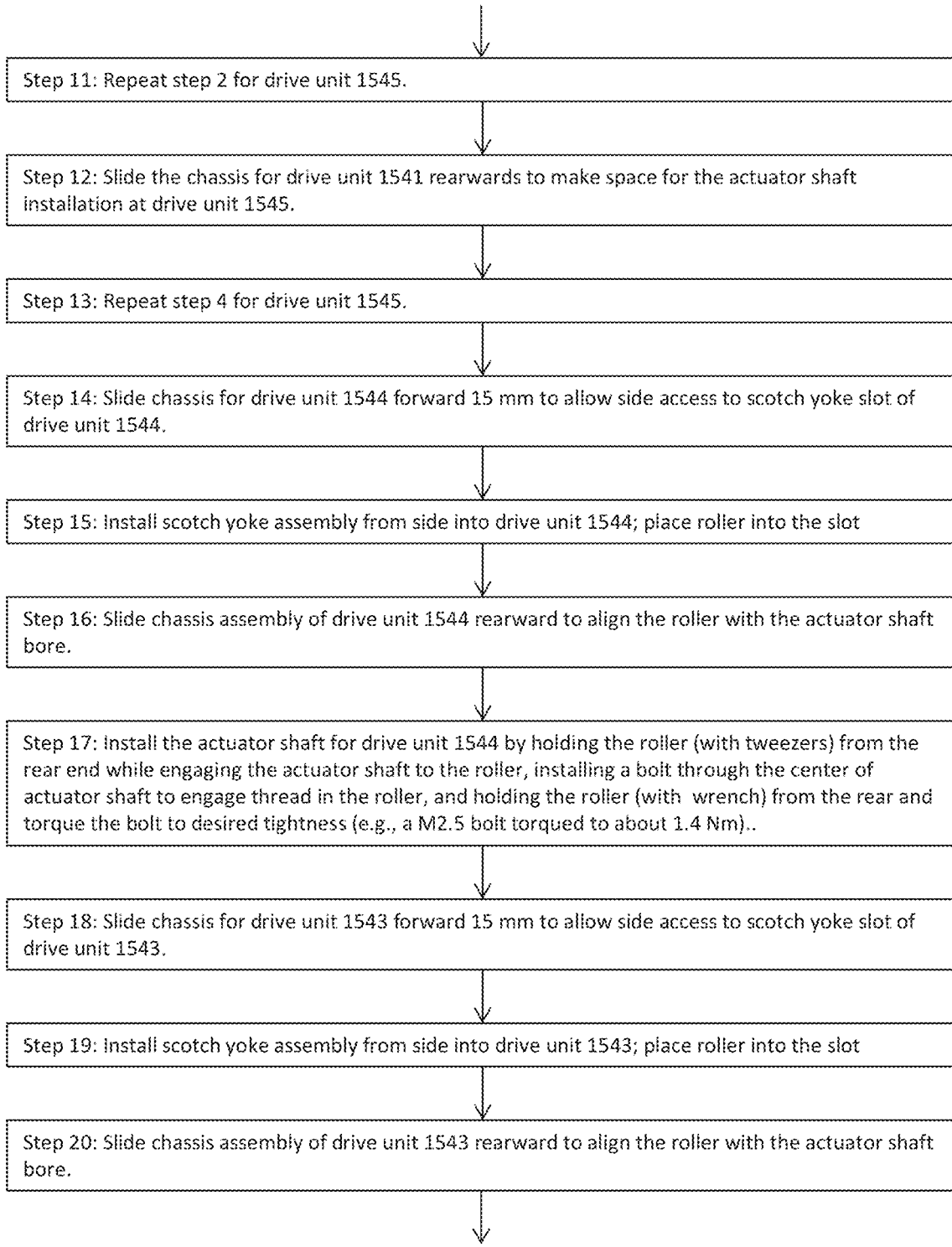
Figure 15G:
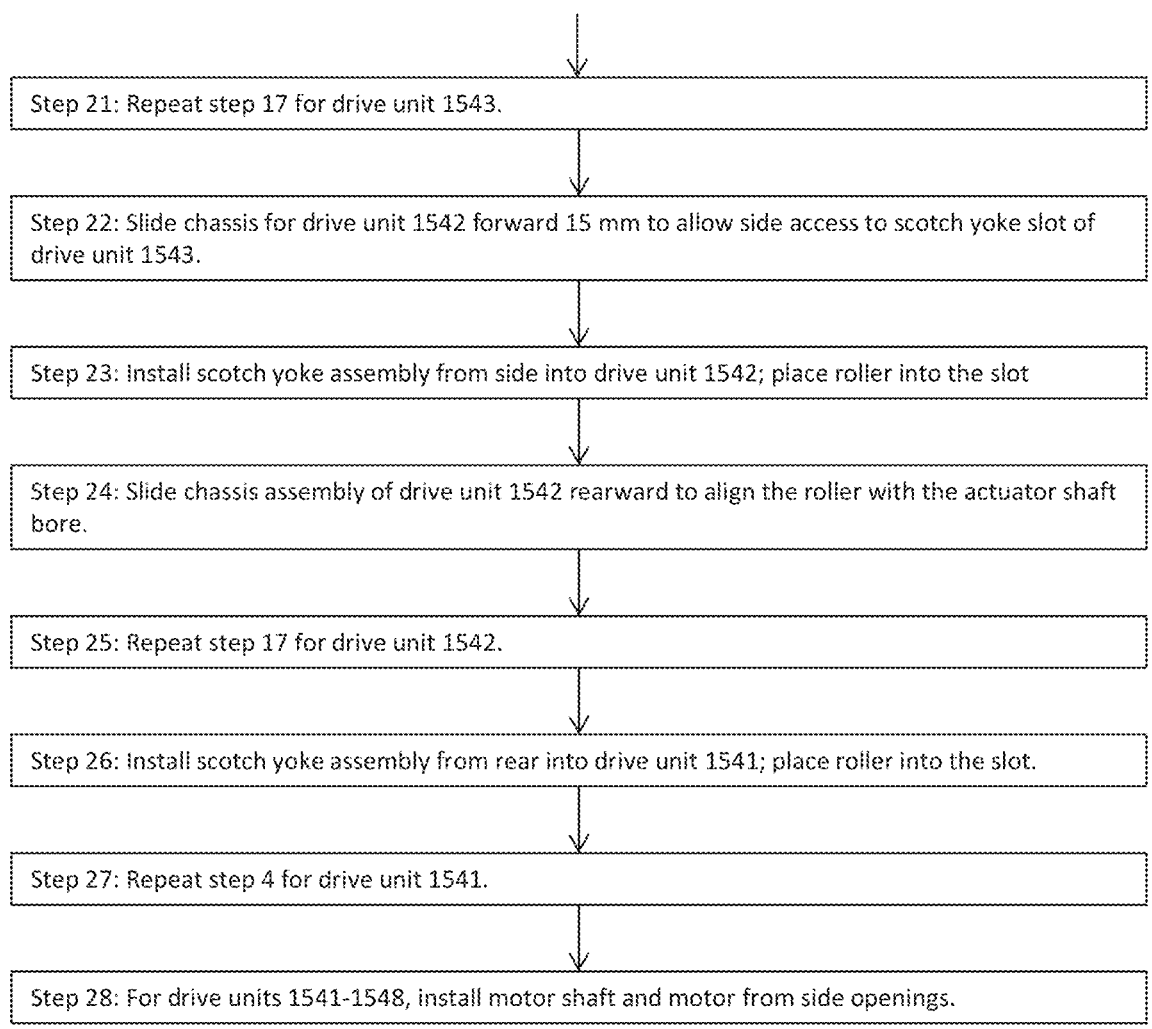
Figure 15H:
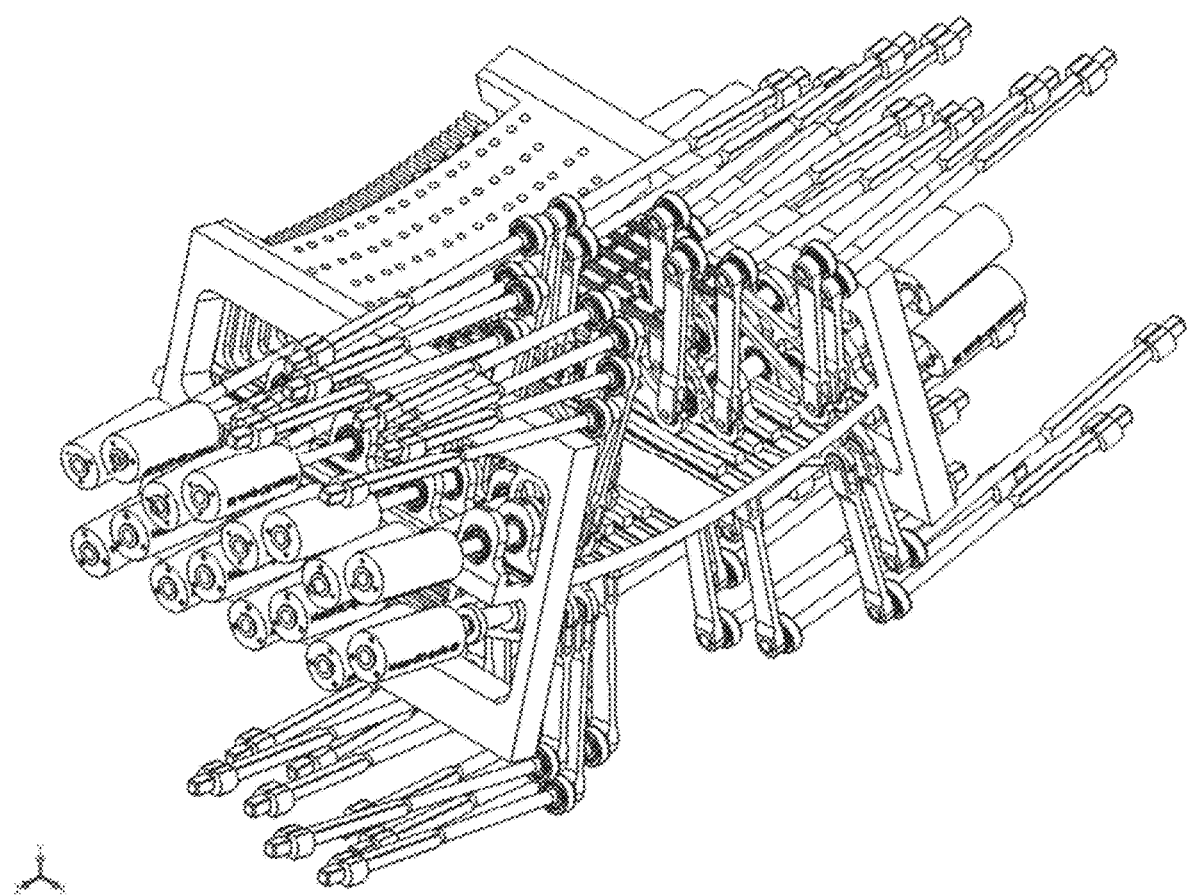
FIG. 15H depicts an elevated perspective view of the plurality of leaf drive mechanisms of FIG. 15C.

FIGS. 15A-15D depict another variation of a collimator leaf drive mechanism comprising a spring system and an actuator system including a scotch yoke or slotted link mechanism. While the variation of FIGS. 11A-11E comprises a spring system having coil springs located along the axis of motion of the leaf, the variation of FIGS. 15A-15D comprises a spring system having a torsion spring disposed orthogonal or perpendicular to the axis of motion of the leaf. As exemplified in these two examples, the type(s) and location(s) of the springs of the spring system may vary as desired. Some leaf drive mechanisms may comprise a spring system where the one or more springs are co-linear and/or co-planar with the travel path of the leaf while other drive mechanisms may comprise a spring system where the one or more springs are not co-linear or co-planar with the travel path of the leaf. The particular arrangement, location, and/or spring type(s) may be determined at least in part by the size and space on a gantry of a radiation therapy system that is available to the collimator, as well as the number, shape, and size of the collimator leaves. Turning now to the example depicted in FIG. 15A, the drive mechanism 1500 may comprise a frame 1504 to which a leaf 1502 is attached, the frame 1504 pivotably attached to a spring system comprising a torsion spring 1506. The frame 1504 may comprise a rail 1505 disposed along a top edge of the frame, extending generally between the leaf 1502 and the attachment location for the spring system. The rotatable joint or pivot 1505 may convert the rotational, twisting motion of the torsion spring 1506 to a lateral, longitudinal motion of the frame 1504 (in direction of arrow 1503), which in turn act to move the leaf 1502 between the open and closed configurations. The torsion spring 1506 is located such that it is orthogonal to the longitudinal motion of the frame (as indicated by arrow 1503). The drive mechanism 1500 may comprise an actuator system comprising a scotch yoke, where the slotted portion 1510 of the scotch yoke is fixedly attached to the frame 1504, and a roller 1512 is disposed within the slot 1510. The roller 1512 may rotatably translate within the slot 1510 by way of a crank 1526 coupled to a motor 1508 via a motor shaft 1524. In some variations, there may be a first bearing 1525a and a second bearing 1525b located along the length of the shaft to support and retain the shaft 1524. Although the shape of the slot 1510 depicted in FIGS. 15A-15B resembles the shape of a straight slot, it should be understood that the slot may have any of the shapes described and depicted previously (i.e., may have one or more curved regions that may have varying radii of curvature and angular sweeps, one or more spring stops, etc.). FIG. 15C depicts one arrangement of a plurality of leaf drive mechanisms of FIGS. 15A-15B for a plurality of leaves in a multi-leaf collimator. FIG. 15C depicts the arrangement of 32 leaves with their corresponding 32 drive mechanisms. The drive mechanisms may be interleaved, staggered, etc. to attain the desired leaf-to-leaf spacing in the collimator. Drive mechanisms and leaves may be assembled in a particular order to attain the depicted arrangement. An illustrative example of an assembly method for assembling eight drive mechanism units (where each unit is similar to the drive mechanism 1500 depicted in FIGS. 15A-15B) for a collimator is described below and depicted in FIGS. 15C-15H. The method may be used to assemble the eight drive mechanism units (each unit comprising a leaf) 1541, 1542, 1543, 1544, 1545, 1546, 1547, 1548 that are schematically depicted in FIG. 15C. This method may be repeated as many times as desired in order to assemble a collimator with the desired number of leaves (e.g., for a 16 leaf collimator, 32 leaf collimator, 64 leaf collimator, etc.). A collimator may comprise a top plate 1530, a middle plate 1532 and a bottom plate 1534. Various components of each of the eight leaf drive mechanisms may be supported and retained by one or more of these plates, as depicted in FIG. 15D. For the purposes of the assembly method described and depicted in FIG. 15F, each of the leaf drive mechanisms or units comprise a chassis assembly, a scotch yoke assembly, an actuator shaft assembly. As an example, the chassis assembly may comprise the frame 1504, leaf 1502 and rail 1505, the scotch yoke assembly may comprise the roller 1512 and crank 1526, the actuator shaft assembly may comprise the actuator shaft 1524 and the first and second bearings 1525a, 1525b. The actuator shaft assembly may be coupled to the motor 1508. FIGS. 15E-15G depict one variation of an assembly method 1550 for assembling eight leaf drive units. Arranging the leaf drive units, and moving the various assemblies of each drive unit to create space to accommodate an adjacent drive unit may help to pack the individual units closely to their adjacent units so that the overall footprint of the collimator may be reduced, and the leaves may tile closely to each other in the radiation beam path. FIG. 15H depicts 32 leaves with each of their corresponding drive mechanisms of a 64 leaf collimator. The 32 leaves and their corresponding drive mechanisms may be assembled by repeating the method depicted in FIGS. 15E-15G four times.

While the spring-based leaf drive mechanisms described above are configured to move the leaf only when a transition between the open and closed positions is desired, in other spring-based drive mechanisms, the springs may continuously move the spring between the open and closed positions. The timing of when the leaf is in the open position or closed position may be synchronized with respect to a pulsing radiation source. For example, to block the transmission of radiation from a radiation source pulsing at a selected frequency, the springs may oscillate such that when the radiation source pulses a radiation beam the leaf is in the closed position. To permit the transmission of radiation, the oscillation of the springs may be phase shifted with respect to its previous oscillatory state so that when the radiation source pulses a radiation beam, the leaf is in the open position. FIGS. 9A and 9B depict plots of the position of a leaf driven by a continuously oscillating or resonating spring-based drive mechanism as a function of time. Time points 900, 902, 904 represent time points at which a radiation source pulses a radiation beam. FIG. 9A depicts the position of a leaf that is driven by a spring that oscillates in-phase with the pulsing of the radiation source, so that the leaf is in the closed or radiation-blocking position when the radiation beam is emitted. The oscillation is such that when the leaf is moved to the open position, the radiation source is not emitting any radiation, so no radiation beam is transmitted to the tissue even though the leaf is not in the closed position. FIG. 9B depicts the position of a leaf that is driven by a spring that oscillates out-of-phase with the pulsing of the radiation source, so that the leaf is in the open or radiation-transmitting position when the radiation beam is emitted. The oscillation of the leaf depicted in FIG. 9B is 180 degrees out-of-phase from the oscillation depicted in FIG. 9A.

If it is desired that the leaf remains closed during the radiation pulse, or remains open during the radiation pulse, the spring may oscillate according to the trajectory of either FIG. 9A or 9B. To transition the leaf from being closed to being open (or vice versa) during the radiation pulse, the timing of the oscillating needs to be shifted. The phase shifting of the spring oscillation from being in-phase with the radiation pulses to being out-of-phase with the radiation pulses (and vice versa) may be achieved by temporarily increasing or decreasing the frequency of the spring oscillation. In some variations, an actuator coupled to the spring and/or leaf may apply a force to the spring and/or leaf to alter the motion of the spring and/or leaf. FIGS. 9C and 9D depict two ways in which the phase of the spring oscillation may be shifted so that the leaf transitions from being in the closed or radiation-blocking position during a radiation pulse (e.g., during time points 906, 908) to being in the open or radiation-transmitting position during the radiation pulse (e.g., during time points 910, 912). In FIG. 9C, the oscillation is shifted from being in-phase with the radiation pulse to being 180 degrees out-of-phase with the radiation pulse by temporarily increasing the frequency of the oscillation. As the leaf moves towards the open position, it is "kicked" back towards the closed position. In FIG. 9D, the oscillation is shifted from being in-phase with the radiation pulse to being 180 degrees out-of-phase with the radiation pulse by temporarily decreasing the frequency of the oscillation. The leaf is slowed down as it moves towards the open position so that it reaches the open position at time point 910.

Figure 9E:
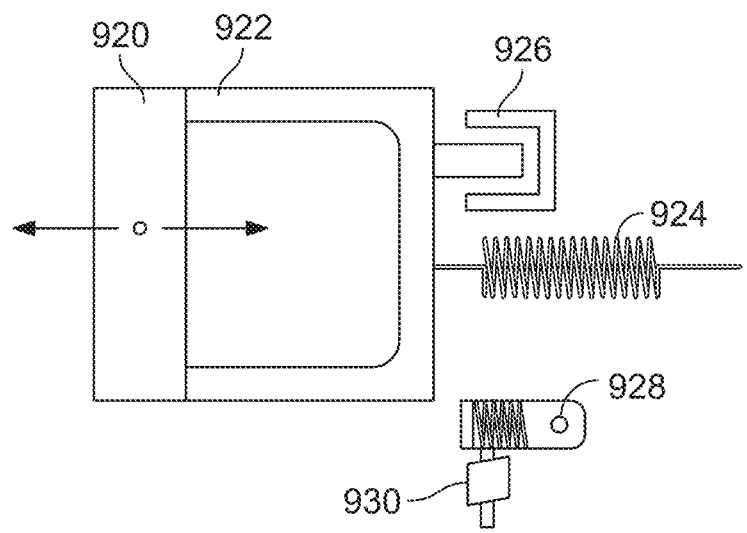
FIGS. 9E and 9F schematically depict one variation of a phase-shifted spring-based leaf drive mechanism.
Figure 9F:
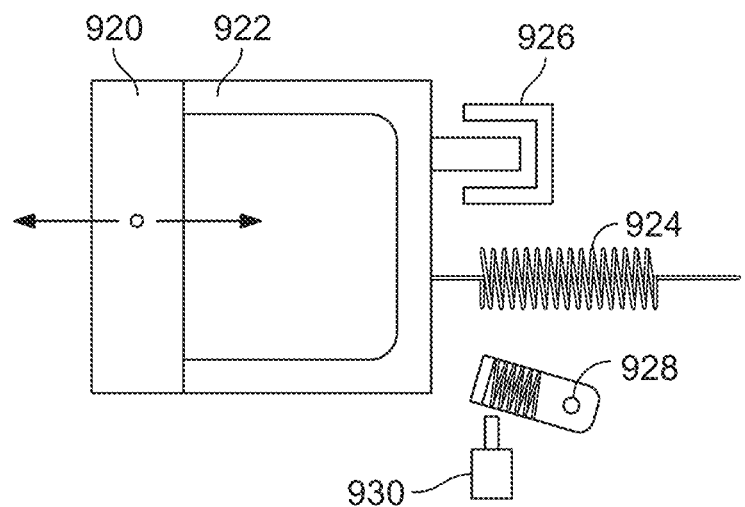

FIGS. 9E and 9F depict one variation of a continuously-oscillating, spring-based leaf drive mechanism comprising one or more actuators for shifting the phase of the oscillation as described above. A leaf assembly may comprise a leaf 920 and support 922. The leaf drive mechanism may comprise a first spring 924 that may be the primary motive force for moving the leaf assembly between the open and closed positions. The first spring 924 may be continuously oscillating in accordance with the position-time plots depicted in FIGS. 9A-9B. An actuator 926, such as a voice coil driver, may be coupled to the leaf assembly in order to push and/or pull the leaf assembly to compensate for any spring energy lost due to friction, as well as to start the leaf moving from a stationary state (e.g., when the collimator powers up at start up, or when the system has been reset after a movement error is detected). The voice coil actuator 926 may be attached to the leaf support 922. The spring-based drive mechanism may also comprise a second spring 928 that may have a disengaged configuration and an engaged configuration. The configuration of the second spring 928 may be controlled by a solenoid 930. FIG. 9E depicts the second spring 928 in the disengaged configuration, where the second spring is not in the travel path of the leaf assembly and does not affect the movement of the leaf assembly by the first spring 924. When the second spring 928 is in the disengaged configuration, the leaf assembly may oscillate according to the movement of the first spring 924, according to the position-time plot of either FIG. 9A or FIG. 9B. When it is desired to shift the phase of the oscillation of the first spring 924, the solenoid 930 may be activated to transition the second spring 928 to the engaged configuration, as depicted in FIG. 9F. In the engaged configuration, the second spring 928 can affect the motion of the leaf assembly in order to shift the phase of the oscillation. In some variations, the second spring 928 may temporarily increase the frequency of the oscillation, similar to the effect depicted in FIG. 9C. Alternatively or additionally, the second spring 928 may be configured to provide an additive force to the oscillation of the first spring 924 to temporarily increase the frequency. In some variations, the second spring 928 may be removed in order to temporarily reduce the frequency.

Figure 9G:
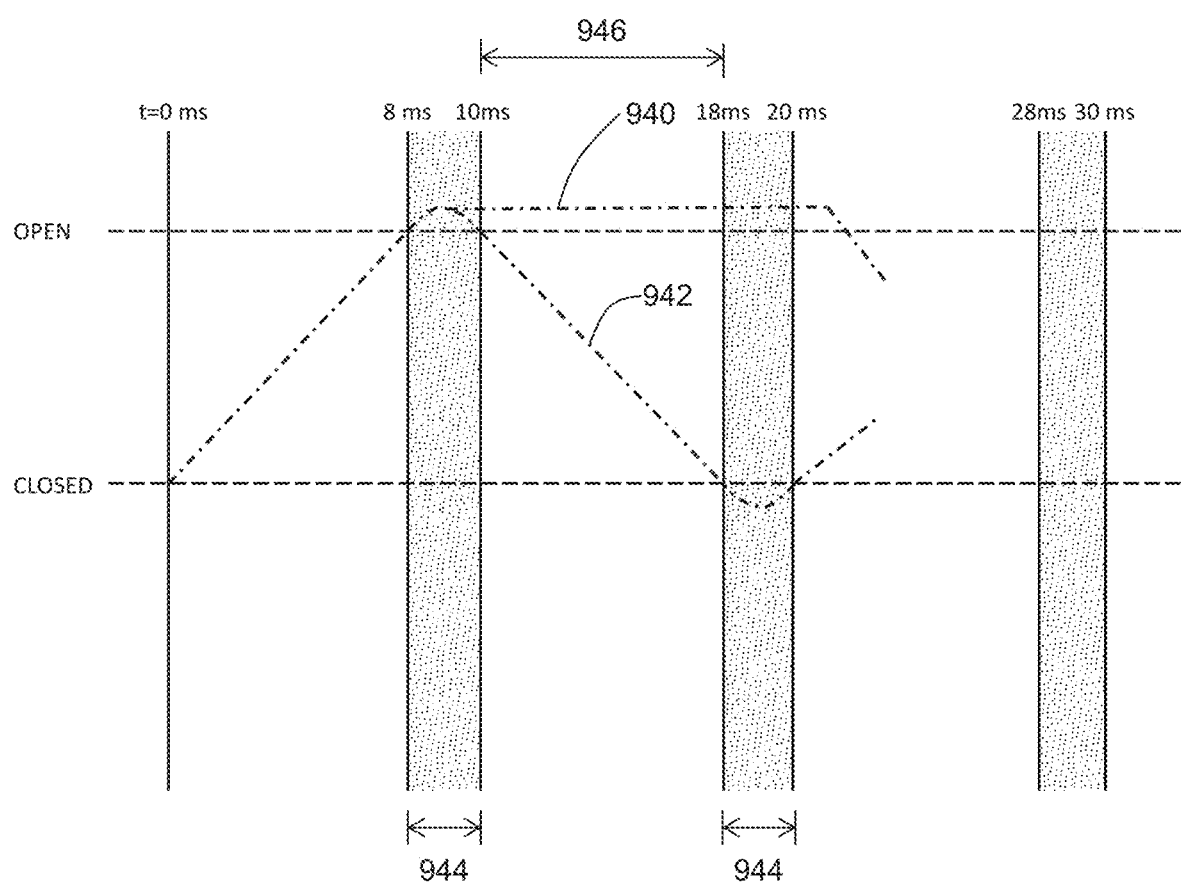
FIG. 9G depicts a timing diagram of another variation of a spring-based leaf drive mechanism.

The position-time plot of another variation of a spring-based leaf drive mechanism is depicted in FIG. 9G. The oscillation of a spring that drives the movement of a leaf or leaf assembly between the open and closed configurations may be adjusted such that the leaf "overshoots" the open and closed positions, and that the duration of time in which the leaf has "overshot" the open or closed position coincides with the radiation pulse width (radiation pulse interval 944). That is, the leaf may move past the nominal position where radiation is either transmitted or blocked, and the duration of time in which the leaf has moved past the nominal point is at least the duration of the radiation pulse width. This may help reduce the need to latch the spring at either the open or closed positions. For example, if it is desired for the leaf to transition between the open position and the closed position for two consecutive radiation pulses (e.g., the leaf follows the 942 trajectory), the leaf is not latched at the open position since the time that the leaf spends overshooting the open position spans the duration of the radiation pulse. The leaf is then allowed to oscillate to the closed position for the next radiation pulse. If however, if it is desired for the leaf to remain in the open position for two consecutive radiation pulses (e.g., the leaf follows the 940 trajectory), the leaf position may be secured by a latch. The latch has the entire duration of the radiation pulse interval 944 to engage the leaf in order to retain it in open position, and to prepare to release the leaf. In this variation, the latch has about 10 ms to engage and release the leaf. This is in contrast to other variations where the time interval during which the latch must engage and release the leaf is much shorter, for example, 2 ms or less. The time duration of the "overshoot" may be adjusted by varying the spring constant of the springs. For example, non-linear springs may be used to attain the desired timing parameters. While the above example describes latching the leaf at the open position, it should be understood that similar principles apply to latching the leaf at the closed position.

Figure 20A:
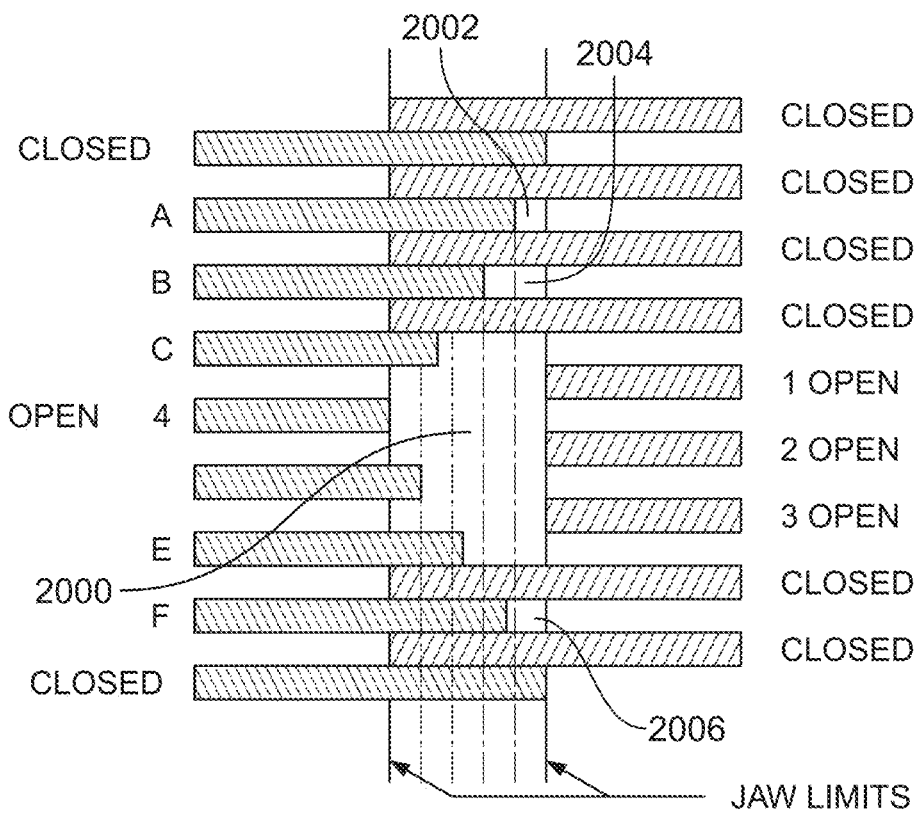
FIG. 20A is a schematic representation of collimator leaves at various positions and FIG. 20B depicts a timing diagram used by a leaf controller to attain the leaf positions depicted in FIG. 20A.
Figure 20B:
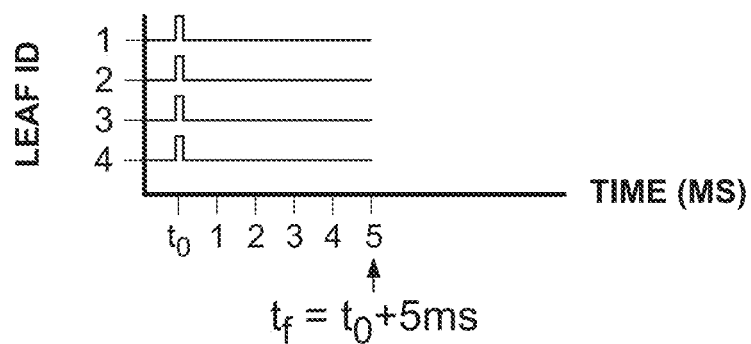
Figure 20B:
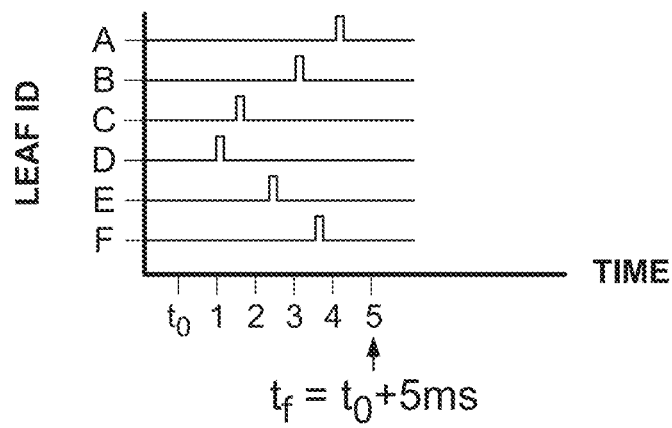

The timing between the firing of a radiation beam and the opening and closing of individual leaves of a binary collimator may be adjusted to attain a desired pattern of beamlets. In some variations, the pattern of beamlets may form a contiguous, two-dimensional shape, which may approximate the shape and size of the region of interest (e.g., tumor). One method of controlling the collimator may comprise staggering the timing of the opening of the collimator leaves such that when the radiation beam is fired, some leaves are open, others are closed, and still others are transitioning between the open and closed states. The trailing edges of the leaves that transitioning between the open and closed states (i.e., the portion of the leaves that are in the beam path) may approximate the edges of the desired beam shape. The relative timing between firing the radiation beam and the position of a particular leaf during beam firing may depend at least in part on the time it takes for that leaf to transition between the open and closed states, as well as the desired shape as a sum of all the beamlets. FIG. 20A depicts an example of binary collimator leaves A-F, 1-4, that are in various states of transitioning between an open and closed states in order to form a pattern of beamlets. The timing of the opening of leaves A-F, 1-4 relative to the beam firing time $t_f$ is depicted in the timing diagram of FIG. 20B in order to attain the leaf positions depicted in FIG. 20A. For the purposes of this example, it is assumed that all the leaves start in the closed state, the maximum width of a beamlet is 5 units and it takes 5 ms for a leaf to transition from the closed state to the open state. Some beamlets may form a contiguous shape, while other beamlets may not be part of the contiguous shape, but may be used to irradiate nearby tumor regions without irradiating (or reducing the irradiation of) tissue between the nearby tumor regions. A contiguous shape 2000 may be formed by varying the timing of the opening of adjacent collimator leaves. Individual beamlets 2002, 2004, 2006 may have different beam widths depending on the relative timing between their opening and the firing time $t_f$. In the pattern of FIG. 20A, leaves 1-4 are entirely open at firing time $t_f$ (i.e., the trailing edge of each leaf clears the entire beam width), and the time at which leaves 1-4 begin to open is to. The remaining leaves A-F are in various intermediate positions as they transition from the closed position to the open position, and accordingly, each begins to open at varying delays from $t_0$. For example, leaf D is nearly entirely open at the time of firing $t_f$, and may start to open before leaf E. The width of the beamlet associated with leaf A is smaller than the width of the beamlet associated with leaf B, therefore, the opening of leaf A is more delayed than the opening of beam B relative to $t_0$. The desired beam profile may be determined during a pretreatment phase, and may be based on images of the tumor acquired via one or more imaging modalities, including but not limited to CT, MRI, PET, etc. A computer-implemented method may compute the relative timing of collimator leaf opening in order to attain the desired radiation profile at the time of beam firing, based on the transition time of the leaves between the open and closed positions and whether the leaves start from an open position or a closed position. It should be understood that this method may be used with any of the binary collimator leaf drive mechanisms described herein. Although the example depicted in FIGS. 20A and 20B assume that all of the leaves are in the closed position at to, in other examples, the leaves may all be in the open position, or some leaves may be open while other leaves may be closed.

While some spring-based leaf drive mechanisms may use linear springs (i.e., springs that have a constant spring constant), other spring-based leaf drive mechanisms may use non-linear springs (i.e., springs that have a variable spring constant). The sinusoidal "position vs. time" trajectory (a.k.a. "shape") associated with linear spring resonator systems may change when using one or more non-linear springs. For example, a "hardening" spring may cause the system to spend less time near extrema, and a softening spring may increase the time spent near extrema. The spring behavior may not be symmetric. In some variations, the springs for a spring-based leaf drive mechanism may be selected such that the leaf may have a shorter dwell time in the closed position and a longer dwell time in the open position. As described above with respect to the cam-based leaf drive mechanism, a spring-based leaf drive mechanism may comprise a single hard latch for the closed position. The actuator used to restore energy to the spring system may optionally be used to tune the shape of the motion. When the actuator applies force in the same direction as the spring, it can be used to "harden" the spring, and alternately when the actuator force is in the opposite direction, the overall behavior will be that of a "softened" spring.

Another variation of a leaf drive mechanism that may be used in a high-bandwidth multi-leaf collimator of a radiation therapy system (e.g., an emission guided radiation therapy system) may comprise a fluid power mechanism, for example, a pneumatic cylinder or motor, or a hydraulic cylinder or motor. A collimator leaf may be coupled to the movement of the piston of a fluid power mechanism. In some variations, a fluid power actuation mechanism may comprise a barrel, a piston movable within the barrel, a fluid source, and one or more fluid conduits between the fluid source and the barrel. The piston may be coupled to a collimator leaf such that the piston motion causes a linear motion of the leaf. The travel path of the leaf may be substantially aligned, and/or co-linear with, and/or parallel with, the longitudinal axis of the barrel. The one or more fluid conduits may comprise one or more valves to regulate and control the fluid flow into the barrel. The one or more valves may be independently operable and controlled such that each valve may open or close separately from the other valves. A controller may be configured to coordinate the timing of the opening and closing of various valves with respect to each other to attain the desired leaf motion within the time frames specified previously. Alternatively, the fluid flow into the barrel may be controlled by a single valve. While the examples described herein may be directed to a pneumatic cylinder or motor, it should be understood that similar operating principles may also apply to a hydraulic cylinder or motor.

One variation of an actuator system comprising a pneumatic mechanism that may be included in a collimator for a radiation therapy system is depicted in FIGS. 10A-10G. A pneumatic leaf actuation mechanism 1000 may comprise a barrel 1002, a piston 1004 movable along the length of the barrel, a first valve 1006 that is fluidly connected to the barrel via a valve conduit 1016 and located at a distal portion of the barrel, a second valve 1008 that is fluidly connected to the barrel via a valve conduit 1018 and located at a proximal portion of the barrel, a fluid source 1014 and fluid conduit 1012a,b that connects the fluid source 1014 to each of the first and second valves. A leaf 1010 may be connected to a piston rod 1005 such that movement of the piston within the barrel 1002 moves the leaf between open and closed positions. In this variation, the leaf travel path is substantially aligned with the longitudinal axis of the barrel. The location where the proximal valve conduit 1018 connects to the barrel may be such that it is located proximal to the piston seal 1003 regardless of the position of the piston 1004, and the location of the distal valve conduit 1016 connects to the barrel may be such that it located distal to the piston seal 1003 regardless of the position of the piston 1004. Each of the first and second valves 1006, 1008 may each comprise two source ports and one output port. The output ports 1020a,b may connect to the valve conduits 1016, 1018 respectively. The first source ports 1022a,b may be fluidly connected to a pressurized fluid source (e.g., air pressurized at 120 psi) via fluid conduits 1012a,b. The second source ports 1024a,b may be connected to air at atmospheric pressure (i.e., vented). In some variations, the second source ports may be air vents. The source ports 1022a,b and 1024a,b of each of the first and second valves 1006, 1008 may be individually opened or closed to connect the output port 1020a,b to either pressurized air or atmospheric air. Each valve may be controlled such that the first and second source ports for that valve are not both open at the same time; either the first source port is open or the second source port is open, but not both. For the purposes of the description below, a valve will be described as "on" when the output port is connected to the pressurized (e.g., high pressure) air source and will be described as "off" when the output port is connected to air at atmospheric pressure (e.g., vented). In some variations, before pressurized air is provided on one side of the piston seal 1003 (e.g., either the proximal side or the distal side), atmospheric air may be provided to the other side of the piston seal 1003. This may help to increase the speed with which the pressurized air can move the piston from one side of the barrel to the other. Venting the air in this manner may help reduce the time it takes for a leaf to transition between the closed and open positions.

Figure 10A:
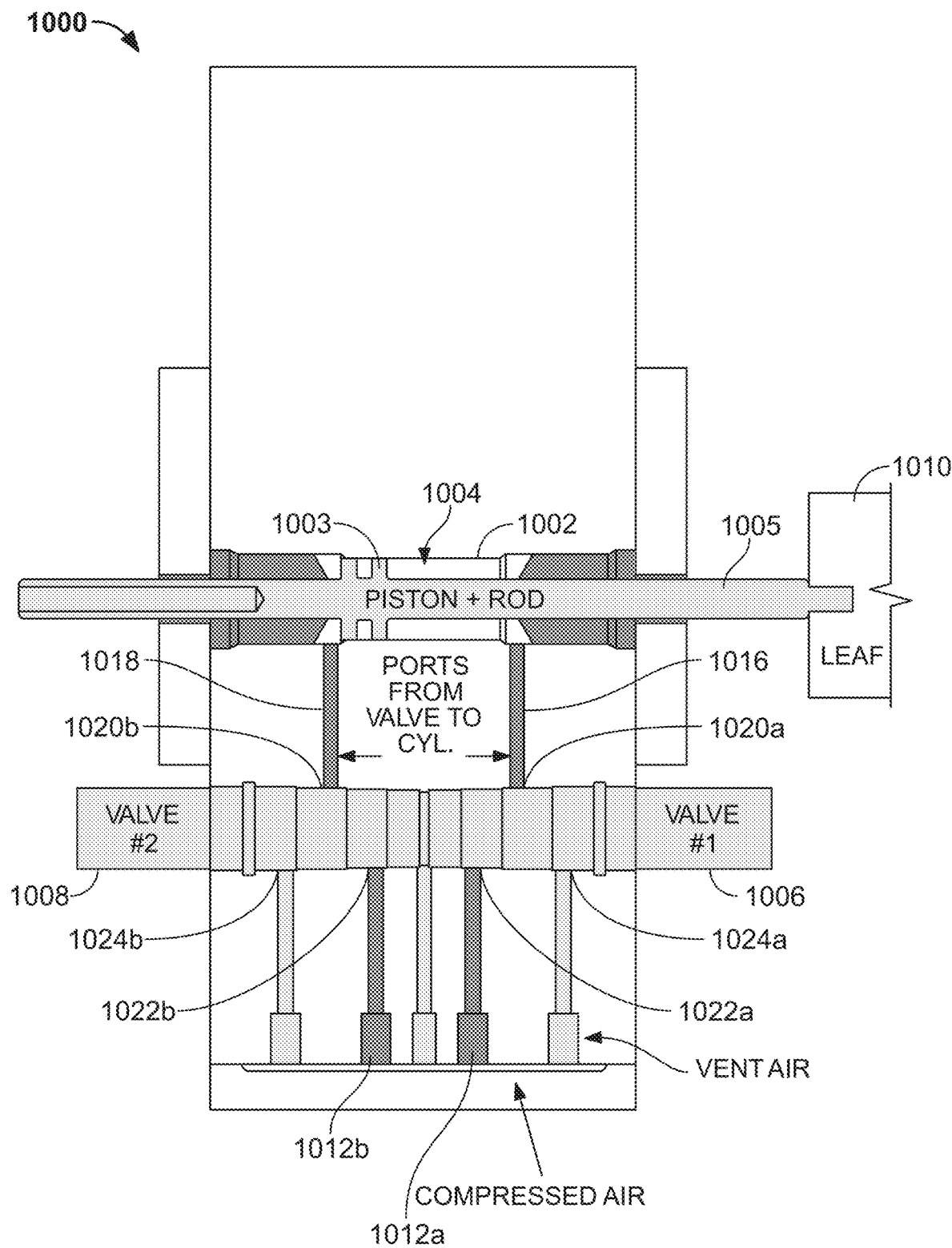
FIG. 10A depicts one variation of a pneumatic leaf drive mechanism.
Figure 10G:
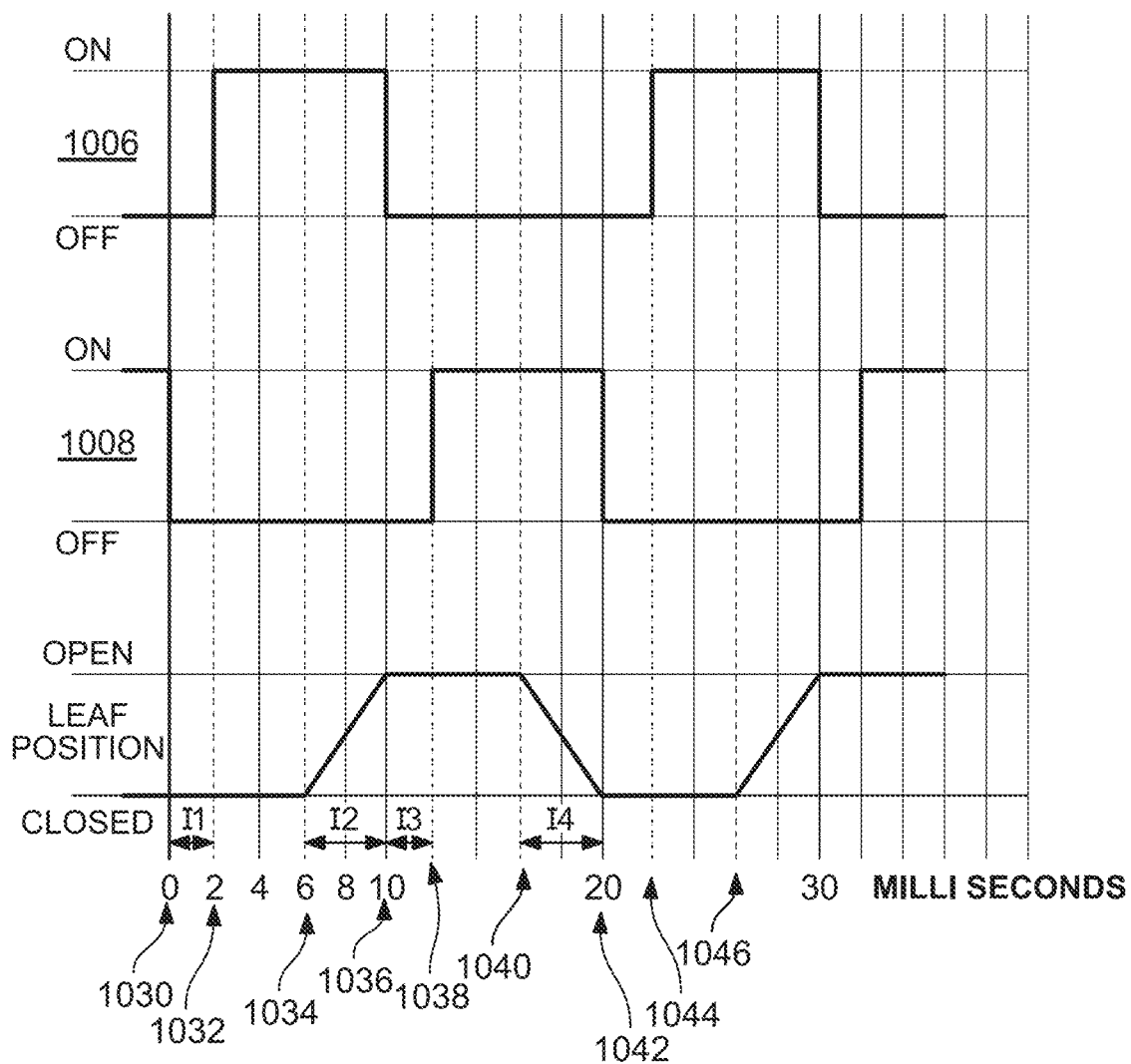
FIG. 10G depicts a timing diagram of the pneumatic leaf drive mechanism of FIGS. 10B-10F.

FIGS. 10B-10F schematically depict the sequence of events as a pneumatic actuation mechanism transitions a leaf from the closed position to the open position and back to the closed position. FIG. 10G depicts timing diagrams of the activation of the first and second valves (i.e., turning on and/or turning off) with respect to the position of the leaf, where the leaf transitions from the closed position before time point 1030 to the open position at time point 1036 and back to the closed position at time point 1042. While the time interval between time points 1030 and 1036 is 10 ms, it should be understood that the interval may be any length of time. Similarly, although the time that the leaf is in the open position (i.e., the interval between time points 1036 and 1040) or in the closed position (i.e., the interval between time points 1042 and 1046) is depicted to be 6 ms, it should be understood that the leaf open or closed duration may be any desired length of time. More generally, the different time intervals shown in the timing diagram of FIG. 10G may vary depending on the desired speed of the leaf transitions and the time at which a leaf needs to be in the open or closed position.

FIG. 10B depicts the leaf 1010 in the closed position. In that position, the first valve 1006 may be connected to atmospheric pressure air (i.e., vented), while the second valve 1008 may be connected to the high pressure air source 1014 (i.e., second source port 1024a of first valve open, first source port 1022b of the second valve open). In this example, in order to move the leaf from the closed position to the open position by time point 1036, the first and second valves initiate the transition starting at time point 1030 (which is, in this case, 10 ms prior to the time that the leaf is in the open position). At time point 1030, the second valve 1008 is turned off and at time point 1032, the first valve 1006 is turned on. During the time interval I1 between time points 1030 and 1032, the pneumatic actuation mechanism in the pre-opened state, which is depicted in FIG. 10C. The duration of interval I1 may be about 2 ms. After the first valve 1006 is turned on, air that has been transferred from the high pressure source 1014 to the barrel 1002 may start moving the piston at time point 1034 to urge the leaf towards the open position. The leaf may be moved to the open position by time point 1036, and the interval I2 is the time it takes for the leaf to transition from the closed position to the open position (which in this example, is 4 ms). FIG. 10D depicts the configuration of the pneumatic actuation mechanism at time point 1036, when the leaf is in the open position.

If it is desired to move the leaf 1010 back to the closed position in the next phase (i.e., in the next firing position, this leaf needs to be closed), then the first valve 1006 may be turned off at time point 1036. At time point 1038, the second valve 1008 may be turned on. During the time interval I3 between time points 1036 and 1038, the pneumatic actuation mechanism in the pre-closed state, which is depicted in FIG. 10E. The duration of interval I3 may be about 2 ms. After the second valve 1008 is turned on for a period of time, air that has been transferred from the high pressure source 1014 to the barrel 1002 may start moving the piston (and therefore, the leaf) at time point 1040 towards the closed position. The leaf may be moved to the closed position by time point 1042, and the interval I4 is the time it takes for the leaf to transition from the closed position to the open position (which in this example, is 4 ms). The time it takes for the leaf to transition from the closed to open position (i.e., interval I2) may or may not be the same as the time it takes for the leaf to transition from the open to closed position (i.e., interval I4).

If it is desired to move the leaf 1010 to the open position in the next phase (i.e., in the next firing position, this leaf needs to be open), then the steps starting from time point 1030 may be repeated. That is, at time point 1042, the second valve 1008 may be turned off and then at time point 1044 the first valve 1006 is turned on. These steps may be repeated in accordance with commands from a controller to the valves to move the leaf 1010 between the open and closed positions.

Alternatively or additionally, some variations of a fluid power system may comprise one or more bumpers located at the two extrema of the leaf travel path (e.g., at the open position and at the closed position) within the barrel. As the piston moves to either of the travel path, it may contact the bumper(s). This may facilitate a slower/gradual deceleration of the motion of the leaf as it arrives at the end of the travel path. This may help to prolong the life of the piston and barrel mechanism, since excessive force and high repetition may damage the piston and/or barrel without proper damping. In some variations, the bumper(s) may be located outside of the barrel, while in other variations, the bumper(s) may be located inside of the barrel. One variation of a fluid power system comprising one or more bumpers is depicted in FIG. 16H. As depicted there, the drive mechanism 1690 for a leaf 1691 may comprise a pneumatic actuator system having a barrel 1696, a piston 1692 having a seal 1694 longitudinally movable within the barrel 1696, and a first bumper or damper 1698 located adjacent to a first end wall of the barrel, and a second bumper or damper 1699 located adjacent to a second end wall of the barrel (e.g., that is opposite the first end wall). The pneumatic system may also comprise a first washer or disk 1693 disposed over one side (or end) of the shaft 1697 of the piston 1692 and a second washer or disk 1695 disposed over the other side (or end) of the piston shaft (e.g., adjacent to the leaf 1691). The first and second washers or discs may be fixedly attached to the piston shaft 1697, and in some variations, may be protrusions or curves extending from the shaft 1697. As the piston 1692 translates with respect to the barrel 1696, the first disk 1693 may contact the first damper 1698 when the leaf is in the closed position, and the second disk 1695 may contact the second damper 1699 when the leaf is in the open position. In variations where the dampers are located within the barrel adjacent to the two end walls, the piston seal may contact the dampers when the leaf moves to the closed position or the open position. The hardness, thickness, and material(s) of the one or more dampers may be selected to absorb enough energy so that the leaf can come to a relatively gradual or gentle stop without being over-damped, and should not be so firm or thick or non-compliant that the leaf bounces off the damper (i.e., under-damped). That is, the material properties and geometry of the dampers may be selected such that the force from the leaf impact is critically damped. In some variations, a damper may comprise two layers made of two different materials. The first leaf-contacting layer of the damper may be a harder material (e.g. having a higher durometer) than the second layer. This may help to distribute the impact force of the leaf over a larger area of the damper so that the energy at the local point of impact is dispersed as it is absorbed. The first leaf-contacting layer may also be a tougher material than the material of the second layer so that it can sustain the wear and tear of repeated contact with the leaf. In some examples, the first leaf-contacting layer of the damper may be made of a material having a Shore A durometer of about 90, while the second layer may be made of a material having a Shore 00 durometer of about 70. In some variations, the total thickness of the damper may be about 0.5 in to about 2 in, e.g., about 0.68 in, about 0.75 in, etc. The thickness of the first leaf-contacting layer may be from about 0.04 in to about 1 in, e.g., about 0.0625 in, about 0.075 in, etc. The thickness of the second layer may be from about 0.4 in to about 1 in, e.g., about 0.625 in, about 0.5 in, 0.75 in, etc.

Figure 10H:
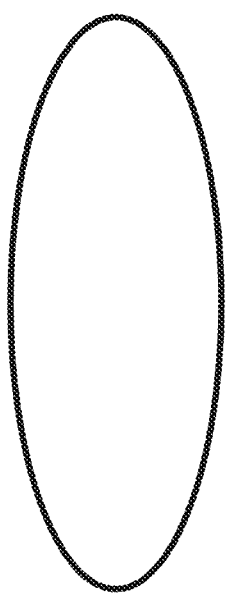
FIGS. 10H and 10I are schematic end views of one variation of a piston of a pneumatic leaf drive mechanism.
Figure 10I:
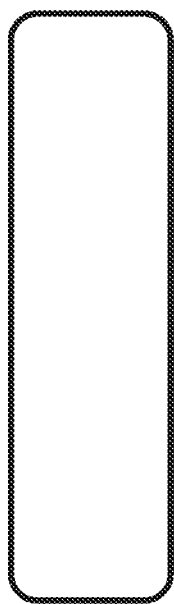

The geometry of the barrel and the corresponding piston may be such that the pneumatic actuation mechanism is compactly arranged in a space-efficient manner. For example, the cross-sectional shape of the barrel and the piston may be non-circular. The cross-sectional shape may be any shape that has a width that is relatively narrow as compared to its length, and may be, for example, rectangular or oval-shaped, as depicted in FIGS. 10H-10I. Such narrow geometry may facilitate space-efficient packing of the fluid power actuation mechanisms. The fluid source may be a fluid compressor. The fluid source may be located on the gantry of a radiation therapy system, or may be located off the gantry.

Figure 16A:
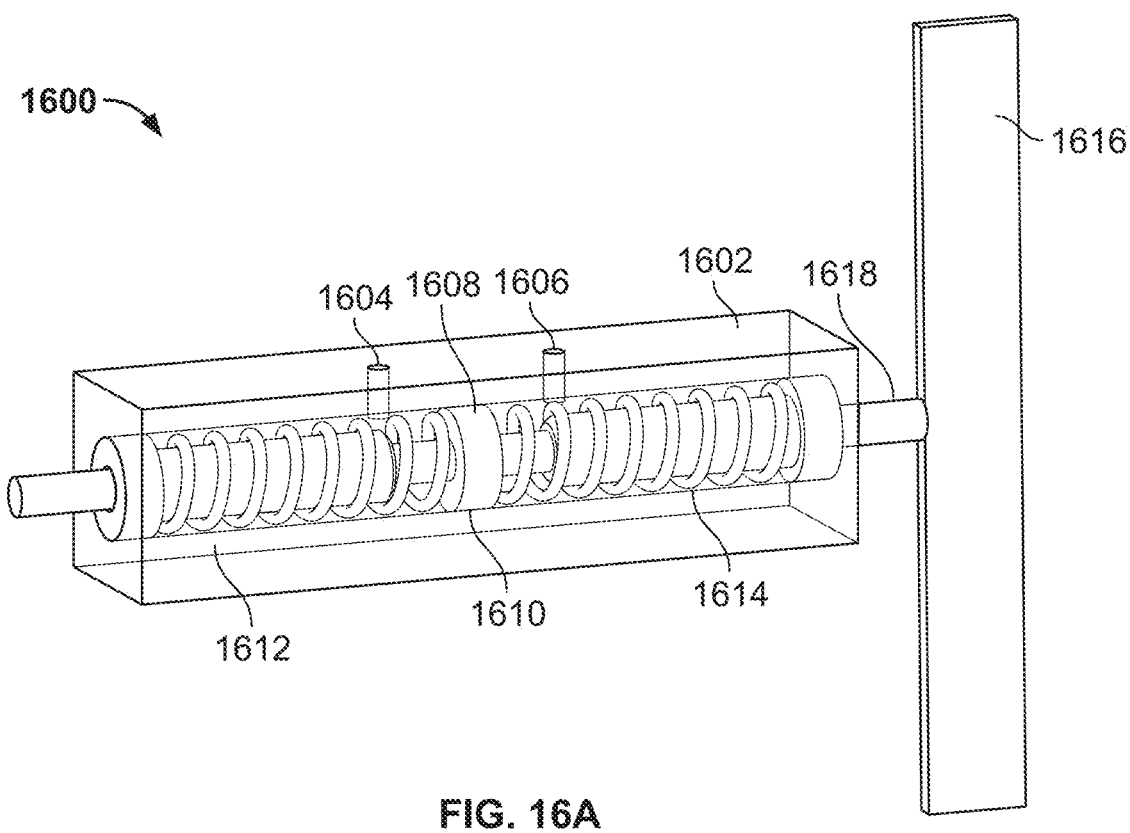
FIG. 16A is a perspective view of a collimator leaf drive mechanism comprising a pneumatic actuator system.
Figure 16B:
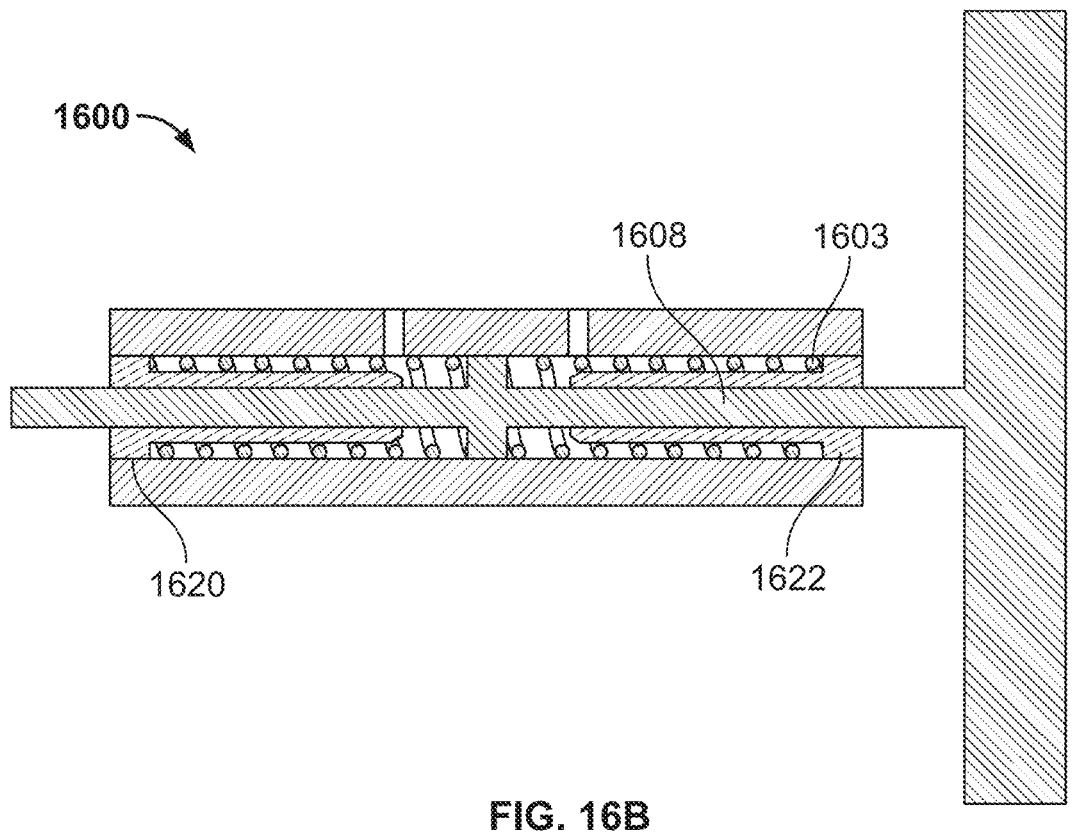
FIG. 16B depicts a cross-sectional view of the pneumatic actuator system of FIG. 16A.
Figure 16C:
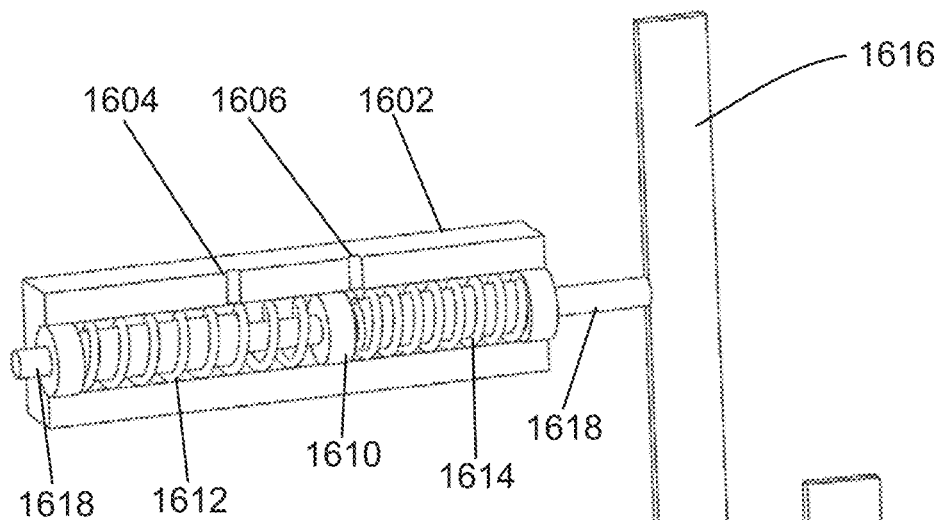
FIGS. 16C-16E depicts the pneumatic actuator system of FIG. 16A as the leaf moves between the closed configuration and the open configuration.
Figure 16D:
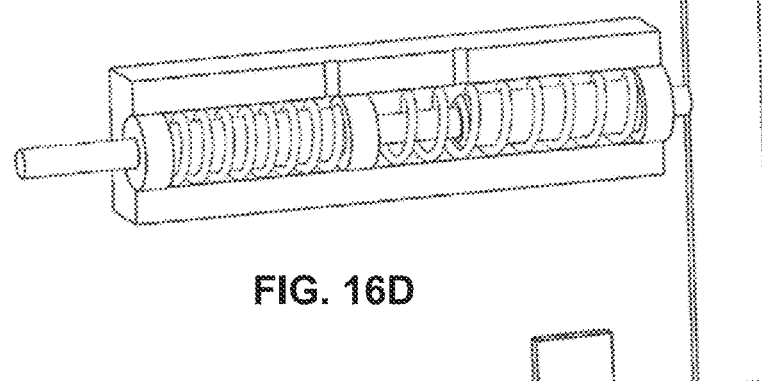
Figure 16E:
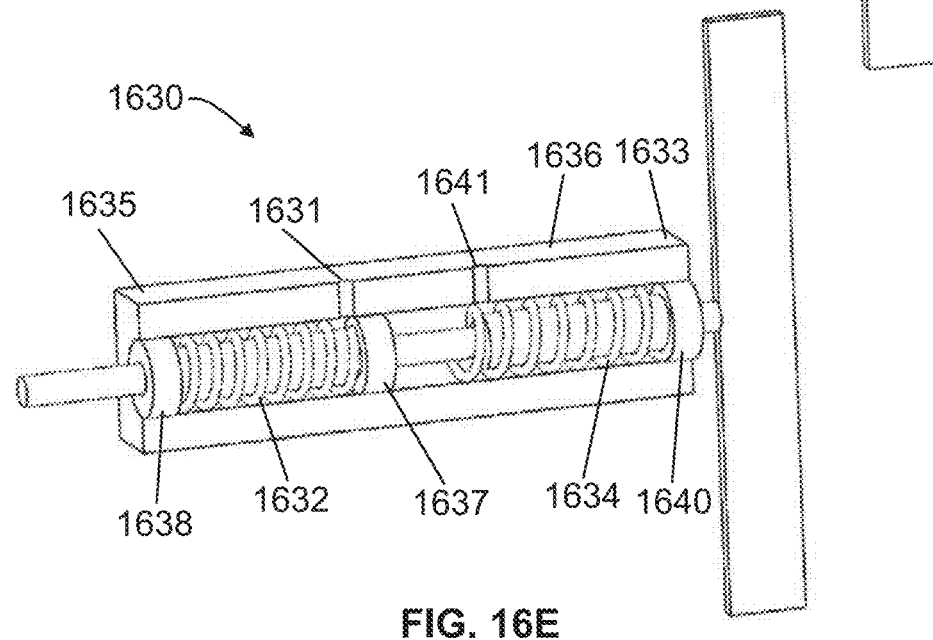
Figure 16F:
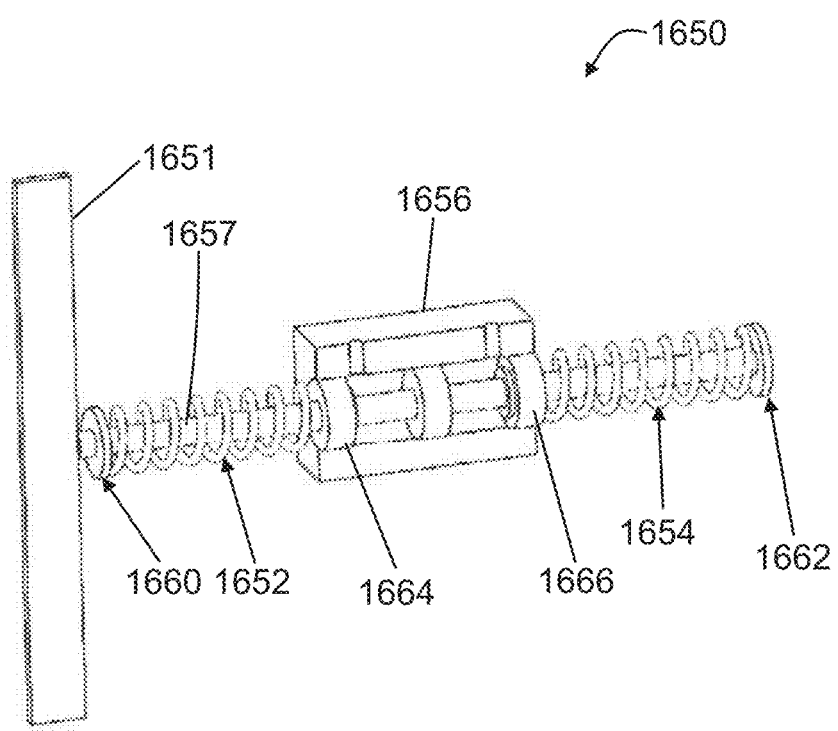
FIG. 16F depicts a variation of a pneumatic system where the spring system is located outside of the barrel.

One variation of a collimator leaf drive mechanism comprising a spring system and a pneumatic actuator system that may be included in a radiation therapy system is depicted in FIGS. 16A-16F. The drive mechanism 1600 may comprise a pneumatic actuator system comprising a barrel 1602 with a longitudinal lumen 1603, a first side opening 1604, a second side opening 1606, and a piston 1608 with a piston seal 1610 that may be movable within the barrel between the first and second side openings, and a spring system comprising a first spring 1612 disposed on a first side of the piston seal 1610 and a second spring 1614 disposed on a second side of the piston. The collimator leaf 1616 may be attached to the piston 1608 via a leaf shaft 1618. In some variations, the leaf shaft 1618 may be integral with the piston 1608, as depicted in FIG. 16B. The spring system may be located within the barrel of the pneumatic system, or may be located outside of the barrel of the pneumatic system. For example, FIG. 16B depicts one example where the spring system (first spring 1612 and second spring 1614) is located within the longitudinal lumen of the barrel. The first spring 1612 may be disposed between the piston seal and a first spring stop 1620 and the second spring 1614 may be disposed between the piston seal and a second spring stop 1622, such that the first and second springs are on opposite sides of the piston seal. The first and second spring stops 1620, 1622 may each have a lumen through which the piston 1608 may be slidably disposed. In other examples, the spring system may be located outside of the barrel of the pneumatic system, as depicted in FIG. 16F. In drive mechanism 1650, the first spring 1652 is disposed outside of the barrel 1656 between a first spring mount or disk 1660 attached to the piston 1657 and a first spring stop or disk 1664 attached to the barrel. The second spring 1654 is disposed outside of the barrel 1656 between a second spring mount or disk 1662 attached to the piston 1657 and a second spring stop or disk 1666 attached to the barrel. Some variations may not have a spring stop located on either side of the barrel, but the springs may be disposed between the end walls of the barrel and the spring mounts. The piston 1657 (and in turn, the first and second spring mounts 1660, 1662) is capable of sliding within the first and second spring stops 1664, 1666 such that the piston seal moves between the two openings in the barrel. Placement of the springs external to the barrel may help facilitate repair and/or replacement of the springs so that repairs of the spring system may be performed with little or no impact to (or disassembly of) the pneumatic actuation system. Alternatively or additionally, the drive mechanisms 1600, 1630, 1650 may comprise one or more bumpers or dampers as described and depicted in FIG. 16H.

The drive mechanisms 1600, 1630, 1650 may be operated in the same manner, for example, as described above with respect to FIGS. 10B-10G. The first and second springs in drive mechanisms 1600, 1630, 1650 may add constructively with the force provided by the injected fluid to provide a cumulative motive force that may move the piston seal within the barrel at a desired speed so that the transition between the open and closed configurations may occur within a desired time interval. The fluid flow into and out of the barrel may also be adjusted such that the magnitude of the pressure provided by the fluid on one side of the piston seal is at least equal to (and/or may exceed) the force applied by the spring system on the opposite side of the piston seal, so that the leaf may be held in a first location or a second location (i.e., a closed configuration or an open configuration). When the fluid pressure on one side of the piston seal opposes and exceeds the forces applied by the spring system, the spring(s) of the spring system may be expanded and/or compressed (e.g., compressed on one side of the piston seal and expanded on the opposite side of the piston seal) such that potential energy is added into the spring system. The addition of potential energy into the spring system by the pneumatic actuator system may help to compensate for the loss of energy as the leaf moves between the open and closed configurations (e.g., due to friction). FIG. 16C depicts the drive mechanism 1600 and the leaf 1616 in a closed configuration (which may correspond to the configurations described and depicted in FIGS. 10B and 10C). FIG. 16D depicts the drive mechanism 1600 and the leaf 1616 in an open configuration (which may correspond to the configurations described and depicted in FIGS. 10D and 10E). As described above with respect to the configurations depicted in FIGS. 10C and 10E, before pressurized air is provided on one side of the piston seal, atmospheric air may be provided to the other side of the piston seal. This may help to increase the speed with which the pressurized air can move the piston from one side of the barrel to the other. Venting the air in this manner may help reduce the time it takes for a leaf to transition between the closed and open positions. In some variations, pressurized air may be provided to help decelerate the leaf at the end of the motion. For example, as the piston moves closer to the location depicted in FIG. 10D, the second valve 1008 may be opened to connect to the pressurized air source to reduce the speed of the piston 1004, which may prevent the leaf from traveling further than its desired endpoint, reducing the leaf motion settling time and preventing the spring from compressing beyond its design point. Similarly, as the piston moves closer to the location depicted in FIG. 10F, the first valve 1006 may be opened to connected to the pressurized air source to reduce the speed of the piston. Using air pressure to facilitate deceleration may help to reduce the wear and tear on the piston, increase spring life, and decrease the settling time for the leaf motion.

The first and second springs in leaf drive mechanism 1600 may have a length such that they are in contact with the piston seal for the full stroke between the open and closed configurations. For example, a first end of the first spring may be attached to the first spring stop and the second end may not be attached to the piston seal, but the length of the first spring is such that the second end is in contact with the piston seal. Alternatively or additionally, the second end may be attached to the piston seal. The second spring may have a similar arrangement. In some variations, one spring is attached to the piston seal, while the other spring is not attached to the piston seal. In still other variations, one or more of the springs may be attached to the piston seal, but not attached to a spring stop on either end of the barrel. In other variations, either or both the first and second springs may have a shortened length such that the spring(s) does not remain in contact with the piston seal for the full stroke. For example, leaf drive mechanism 1630 may have a spring system comprising a first spring 1632 and a second spring 1634 located within a barrel 1636. One end of each of the first and second springs may be attached to corresponding spring stops 1638, 1640. In the variation depicted in FIG. 16E, the other end of the second spring 1634 may not be attached to the piston seal 1637, and may have a length that is shorter than the distance between the first side opening 1631 and barrel end wall 1633 such that the second spring 1634 does not contact the piston seal 1637 as it moves toward the first side opening 1631. The first spring 1632 may have a similar arrangement, or may be attached to the piston seal 1637 and/or have a length that is at least the same as the distance between the opposite barrel end wall 1635 and the second opening 1641. The shorter spring(s) may allow the piston seal to "fly" across center of travel while still being pushed by the fluid. This may cause the deceleration of the seal as the leaf approaches the open or closed position to start later. The arrangement depicted in FIG. 16E may result in faster travel through the middle of the stroke (as compared to an arrangement where the springs are attached at both ends to the piston seal and spring stops) but may also cause some "over-travel" at the end of the stroke (i.e., the leaf travels beyond the minimum distance to clear the radiation beam path in the open configuration, and/or the leaf travels beyond the minimum distance to obstruct the radiation beam path in the closed configuration).

Figure 16G:
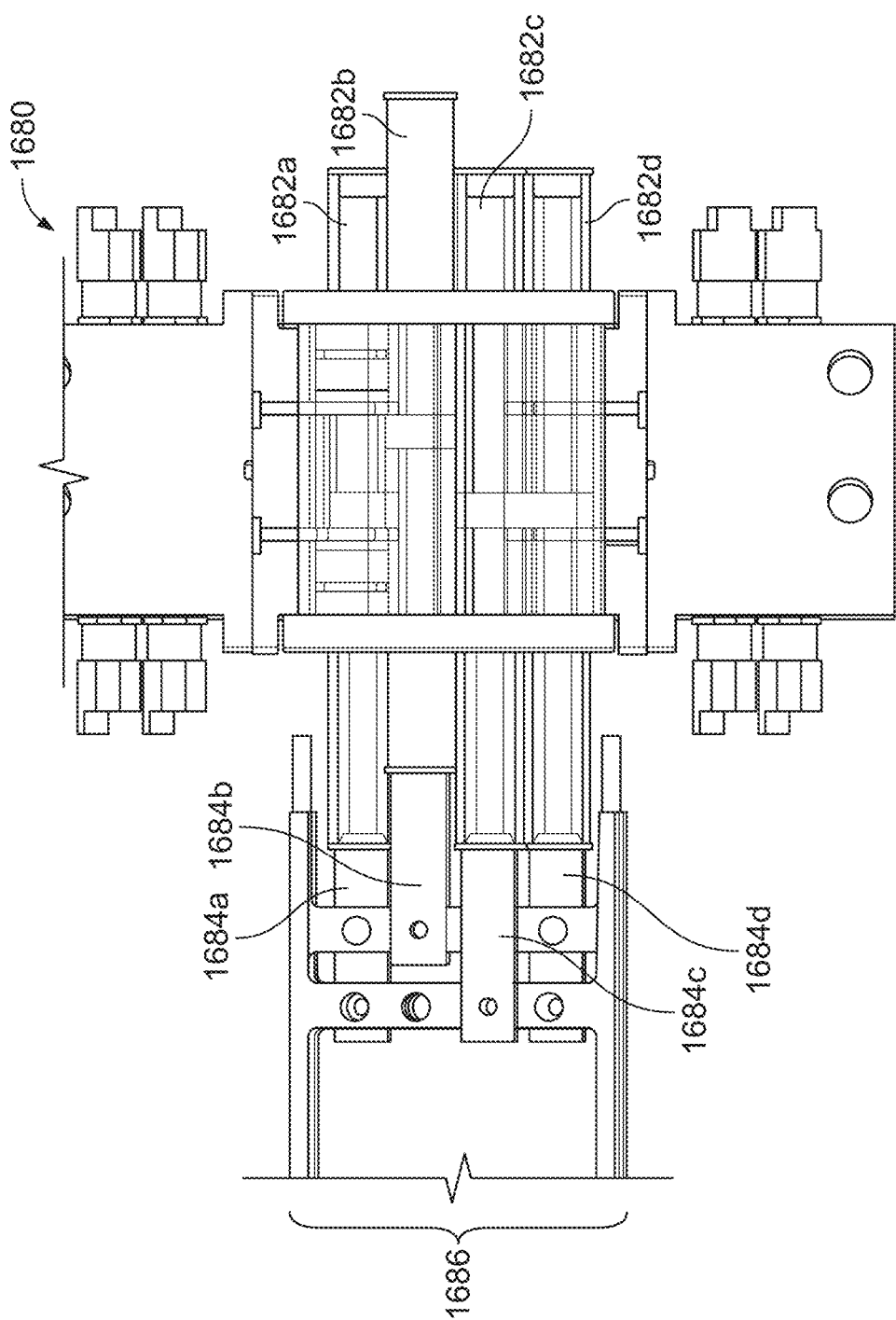
FIG. 16G depicts a plurality of pneumatic actuator systems assembled/packaged together.
Figure 16H:
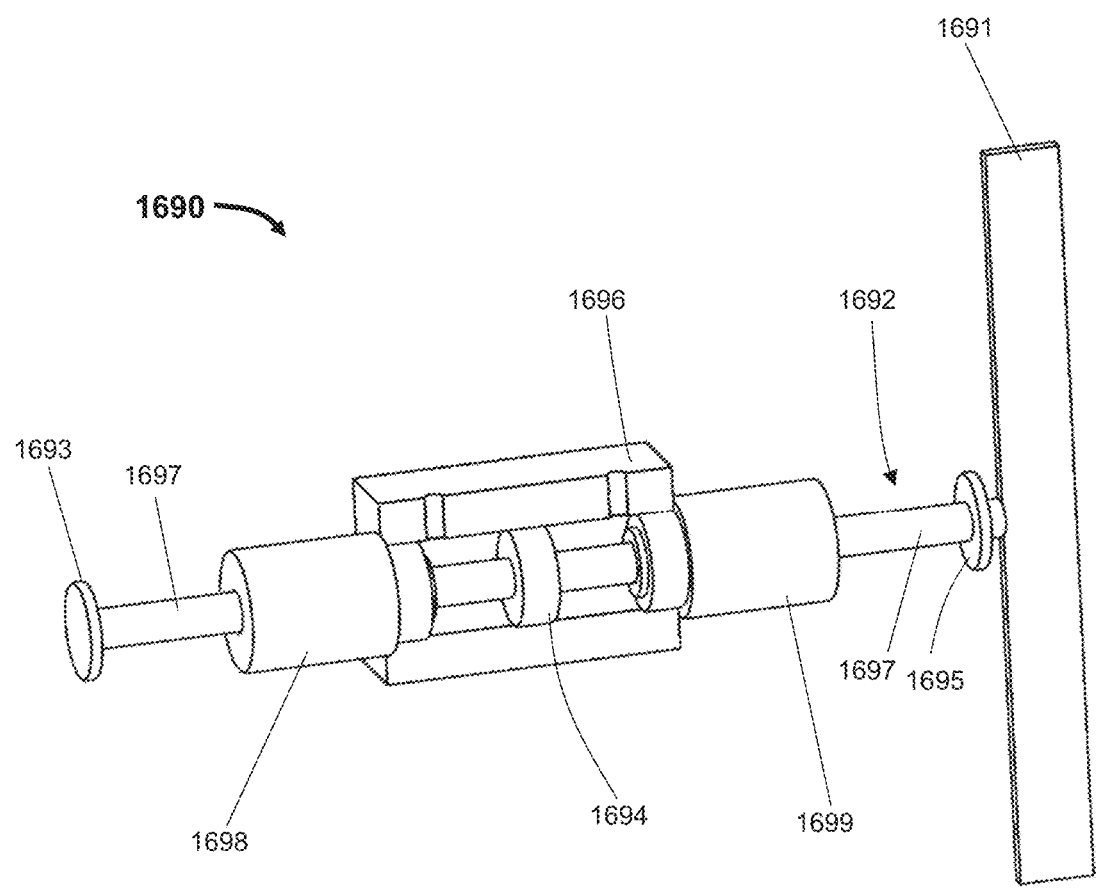
FIG. 16H depicts one variation of a pneumatic actuator system comprising one or more bumpers or dampers.

FIG. 16G depicts an assembly of four leaf drive mechanisms, each comprising a pneumatic actuation system and a spring system as described above. The spring systems 1682*a*, 1682*b*, 1682*c*, 1682*d* of each of the four drive mechanisms may comprise springs that are external to the barrel of the pneumatic actuation mechanism. Each of the four leaves (not shown) may be coupled to the four drive mechanisms by four frames 1684*a*, 1684*b*, 1684*c*, and 1684*d*. The drive mechanisms may be arranged such that they are tiled together in a staggered fashion, so that the drive mechanisms are attached to their respective frames at different points along the width 1686 of the frames. Staggering the attachment location of the drive mechanisms to the frames may help to reduce the space between each of the drive mechanisms (in the direction perpendicular to the drawing plane) so that the space occupied by the collimator may be more compact. FIG. 16G depicts an assembly of four leaves and drive mechanisms which may be repeated and scaled up to include as many leaves as may be desired for a collimator. For example, a collimator may have 16, 32, 64, 128 or more leaves each with their own drive mechanisms.

While some collimator leaf drive mechanisms may comprise a spring system and an actuator system having a pneumatic or a slotted link mechanism, other drive mechanisms may comprise an electromagnetic actuator system. An electromagnetic actuator system may comprise a movable member to which the leaf is attached, a first coiled assembly and a second coiled assembly separated by a gap to the first coiled assembly. The movable member may be located within the gap, and movable between the first and second coiled assemblies. The current through the coils of each coiled assembly generates a magnetic field, and the direction and magnitude of the field depend on the magnitude and direction of the applied current. When it is desired to retain the leaf in the open or the closed configuration, one coiled assembly (e.g., either the first or the second coiled assembly) may be activated by applying a current through its coils to hold the movable member against that coiled assembly. To retain the leaf in the closed or open configuration, the other coiled assembly (e.g., either the second or the first coiled assembly) may be activated by applying a current through its coils to hold the movable member against that coiled assembly. Some variations may comprise one or more permanent magnets that may be configured to retain the leaf in the open or closed configurations without drawing any electrical power. For example, the movable member may comprise a permanent magnet. In other variations, one or more electromagnets may be used and the amount of electrical power supplied to those electromagnets to hold the leaf in the open or closed configurations may be determined at least in part by the amount of magnetic force needed to counteract the forces generated by the spring system. Electromagnetic actuator systems may include variable reluctance actuators, such as linearized variable reluctance actuators.

Figure 17A:
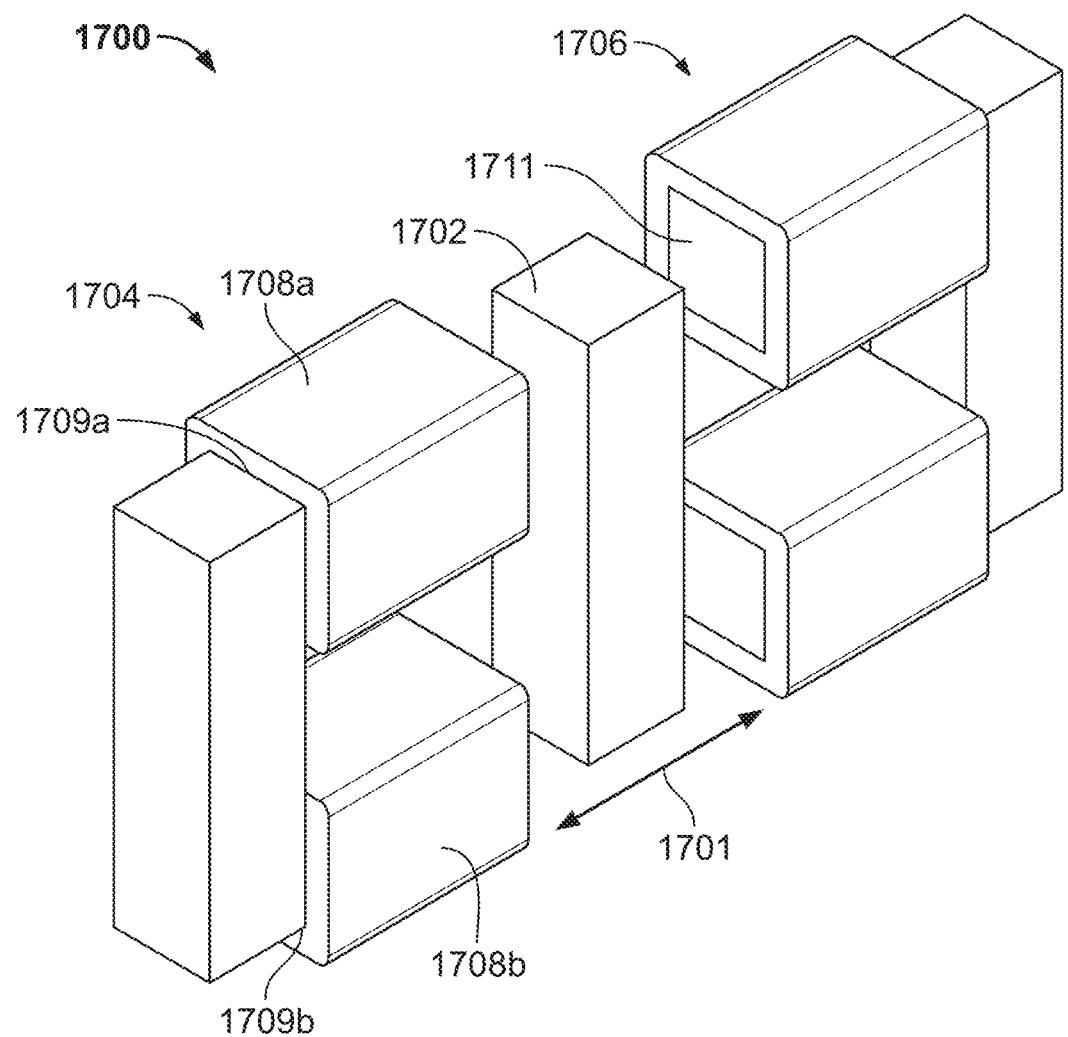
FIG. 17A is a perspective view of a collimator leaf drive mechanism comprising an electromagnetic actuator system.
Figure 17B:
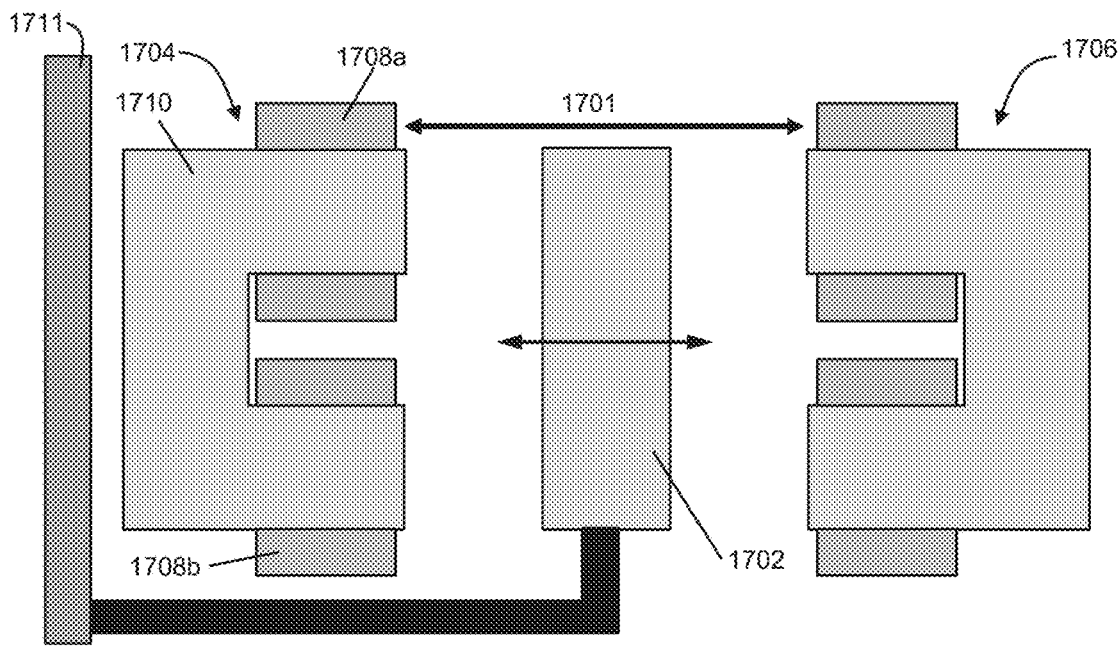
FIG. 17B is a side view of the electromagnetic actuator system of FIG. 17A.
Figure 17C:
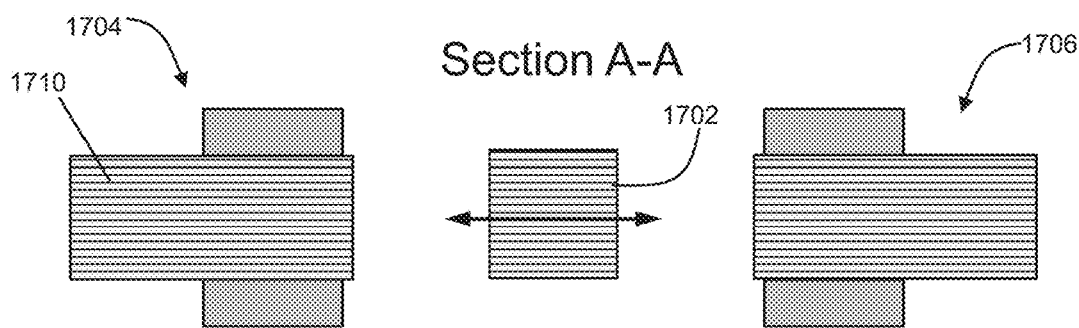
FIG. 17C is a cross-sectional view of the electromagnetic actuator system of FIG. 17C taken along line A-A in FIG. 17D.
Figure 17D:
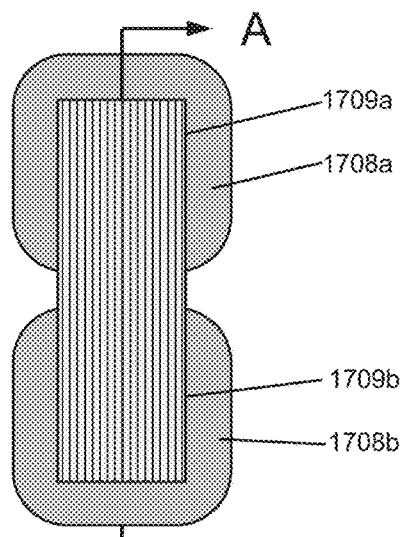
FIG. 17D is an alternate side view of the electromagnetic actuator system of FIG. 17A.
Figure 17E:
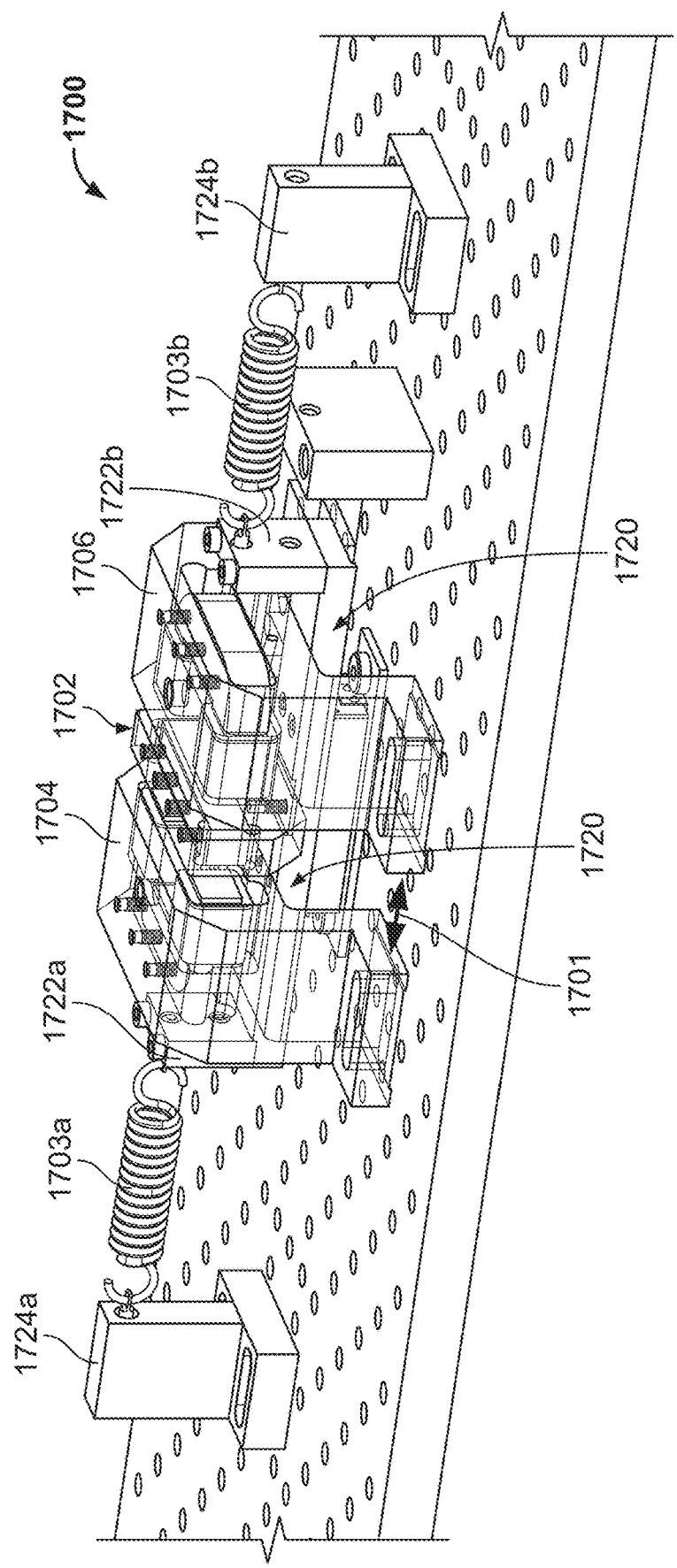
FIG. 17E is a perspective view of one variation of a collimator leaf drive mechanism comprising an electromagnetic actuator system similar to that of FIG. 17A.

One variation of an electromagnetic actuator system that may be used in conjunction with a spring system (such as any described herein) in a multi-leaf collimator is depicted in FIGS. 17A-17E. Electromagnetic actuator system 1700 may be a variable reluctance actuator and may comprise a movable member 1702 located between a first coiled assembly 1704 and a second coiled assembly 1706 that is separated from the first coiled assembly by a gap 1701. A collimator leaf 1711 (schematically represented in FIG. 17B) may be attached to the movable member 1702. The movable member 1702 moves within the gap 1701 between the first and second coiled assemblies depending on the cumulative forces on the movable member from the first and second coiled assemblies and the spring system, as shown in FIG. 17E. The movable member 1702 (to which a collimator leaf may be attached) may be attached to a movable mount 1720. The movable mount 1720 may comprise a first spring attachment portion 1722*a* located at a first end of the movable mount and a second spring attachment portion 1722*b* located at a second end of the movable mount. The spring system may comprise a first spring 1703*a* and a second spring 1703*b*. The first and second springs may be coil springs (as depicted in FIG. 17E), or may be any type of spring as described previously. A first end of the first spring 1703*a* may be attached to the first spring attachment portion 1722*a* of the movable mount and a second end of the first spring 1703*a* may be attached to a first spring mount 1724*a*. A first end of the second spring 1703*b* may be attached to the second spring attachment portion 1722*b* of the movable mount and a second end of the second spring 1703*b* may be attached to a second spring mount 1724*b*. The first and second spring mounts 1724*a,b* may be fixedly attached to a base (e.g., a mounting plate, board, or substrate) such that the springs mounts 1724*a,b*, the first coiled assembly 1704 and the second coiled assembly 1706 are stationary relative to the movable member 1702 and the movable mount 1720. The size of the gap 1701 may be selected to correspond to the travel distance of the leaf from the open configuration to the closed configuration, and in some variations, may be greater than or equal to the desired beam width. For example, the gap 1701 may be from about 12 mm to about 15 mm. The size of the gap may be selected to compress and/or expand the one or more springs of the spring system to add potential energy to the spring system that is at least equal to (and may optionally be greater than) the spring forces that were lost during the motion of the springs and the leaf and/or movable member (e.g., energy losses due friction, drag, etc.). Each coiled assembly may comprise a first coil having a first lumen and a second coil having a second lumen, and a core that extends through both the first and second lumens. For example, as depicted in FIGS. 17A, 17B and 17D, the first coiled assembly 1704 may comprise a first coil 1708*a* having a first lumen 1709*a*, a second coil 1708*b* having a second lumen 1709*b*, and a C-shaped core 1710 that extends through both the first and second lumens. The first and second ends of the C-shaped core may extend through the lumen of the coils (see, for example, FIG. 17B), or may be flush with the opening of the lumen of the coils. The coils may comprise copper, aluminum, silver, gold, carbon nanotubes or other conducting materials, any of which may have a round, square, rectangular, or ribbon-like cross-section. For example, the coils may have a cross-sectional shape where the width is greater than the thickness/height of the coil, and/or may be one or more strips, sheets, ribbons, braids, etc. of the materials described above. The core may comprise laminated steel, solid steel, laminated steel alloys, or solid steel alloys. The movable member 1702 may comprise laminated steel. The movement of the movable member 1702 may be a function of the distance of the movable member to the first coiled assembly, the distance of the movable member to the second coiled assembly, and the electromagnetic force generated by each of the first and second coiled assemblies, in addition to the forces exerted on the movable member from the spring system. The closer the movable member is to a coiled assembly, the greater the attractive force exerted on the movable member by that coiled assembly. The force (either attractive or repulsive, depending on the direction of the current) generated by a coiled assembly that is exerted on the movable member may be non-linearly related to the position of the movable mass relative to the coiled assembly and the current through the coils of the coiled assembly (e.g., the force may be inversely proportional to the gap between the coiled assembly and the movable member, and proportional to the current squared). For example, the electromagnetic actuator system 1700 may be an opposed unipolar variable reluctance actuator. When it is desired to retain the leaf in the open or the closed position, one coiled assembly (e.g., either the first or the second coiled assembly) may be activated by applying a current through its coils to hold the movable member 1702 against that coiled assembly. To retain the leaf in the closed or open position, the other coiled assembly (e.g., either the second or the first coiled assembly) may be activated by applying a current through its coils to hold the movable member 1702 against that coiled assembly.

Figure 18A:
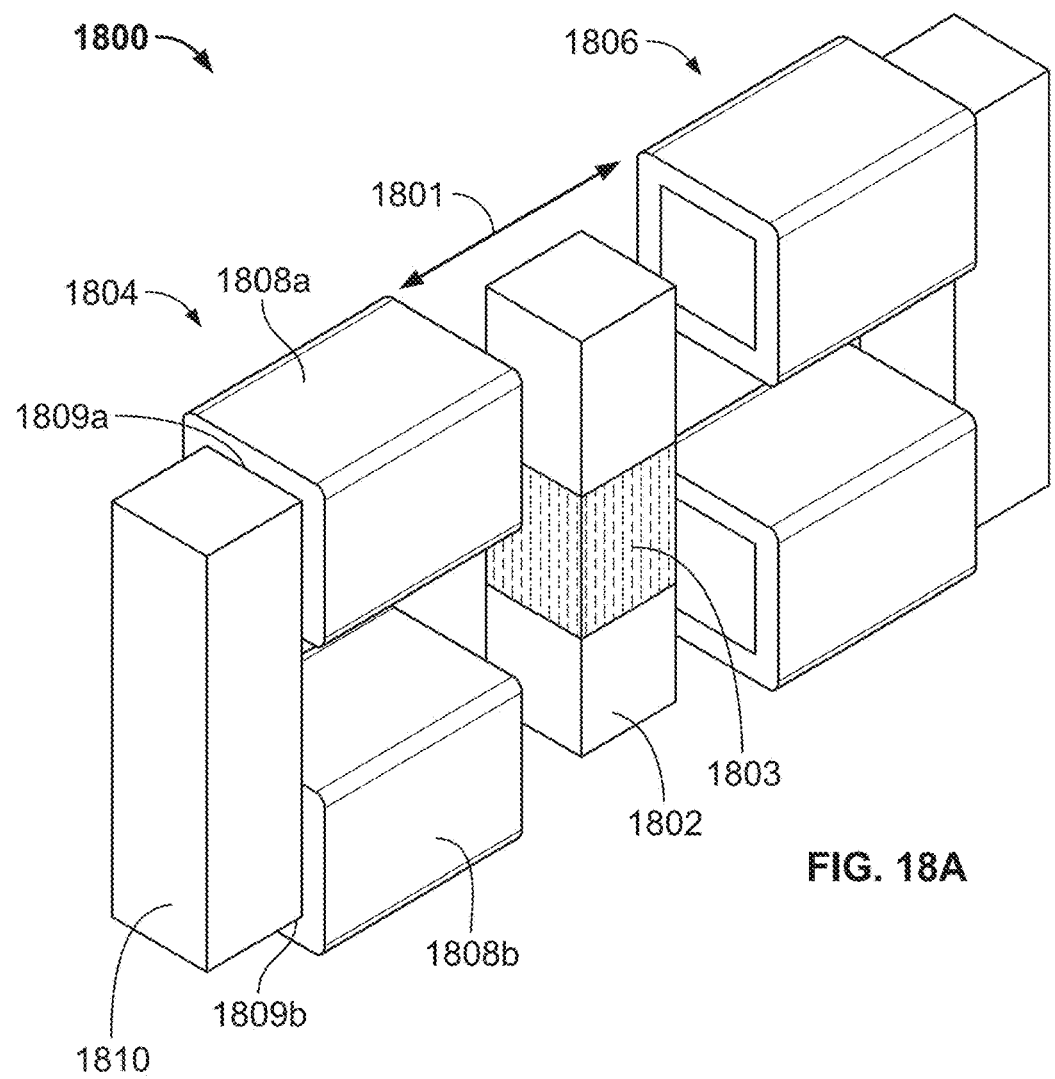
FIG. 18A is a perspective view of another variation of a collimator leaf drive mechanism comprising an electromagnetic actuator system.
Figure 18B:
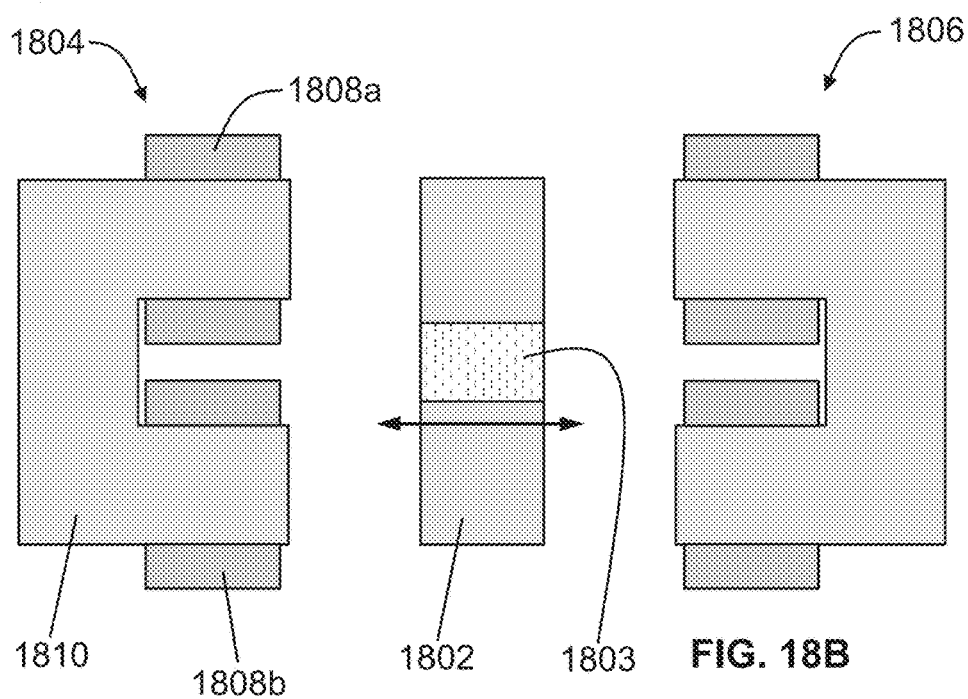
FIG. 18B is a side view of the electromagnetic actuator system of FIG. 18A.

Another variation of an electromagnetic actuator system is depicted in FIGS. 18A and 18B. The electromagnetic actuator system 1800 may be similar to the system 1700 depicted in FIGS. 17A-17D (like numbers represent like elements), and the description for system 1700 may also apply for system 1800. Similarly, a collimator leaf may be attached to the movable member 1802 as depicted in FIG. 17B. The system 1800 may comprise a movable member 1802 comprising a permanent magnet 1803. The permanent magnet 1803 may be located anywhere on the movable member, for example, may be located within the movable member (e.g., permanent magnet core), and/or along the surface of the movable member. In some variations, a movable member may comprise a plurality of permanent magnets, which may be arranged linearly along a length of the movable member, entirely enclosed within the movable member, partially enclosed within the movable member, on the surface of the movable member, symmetrically or asymmetrically arranged, on one or both ends of the movable member, etc. The permanent magnet 1803 may act to linearize the force (either attractive or repulsive, depending on the direction of the current) generated by a coiled assembly that is exerted on the movable member. That is, the generated force may be linearly related to the position of the movable mass 1802 relative to the activated coiled assembly and the current through the coils of the activated coiled assembly. This linearizing effect may be more pronounced when the size of the gap 1801 smaller than the smallest dimension of the cross-sectional shape of the end portion 1811 of the core 1810 (e.g., the width of the gap is less than about 20%, or less than about 10%, or less than about 5% or less than about 2% or less than about 1% of the smallest dimension of the end portion 1811 of the core), and may be less applicable when the gap 1801 is similar to the pole face dimension (e.g., the width of the gap is greater than about 50%, or greater than about 70%, or greater than about 75%, or greater than about 80%, or greater than about 90% of the smallest dimension of the end portion 1811 of the core). In addition, the permanent magnet 1803 in the movable member 1802 may allow the system 1800 to retain the leaf in either the closed or open configuration without driving a current through the coiled assemblies, which may help to reduce the power consumption of the system 1800. To release the movable member 1802 from the coiled assembly to which it is magnetically attached (for instance, the first coiled assembly) so that the leaf may transition from one configuration to the other, a current with the appropriate magnitude and direction may be applied to the first coiled assembly so that the attractive force between the first coiled assembly and the movable member is reduced (e.g., the repulsive force between them is increased), which may then allow the forces from the spring assembly to move the movable member away from the first coiled assembly towards the second coiled assembly.

Figure 19A:
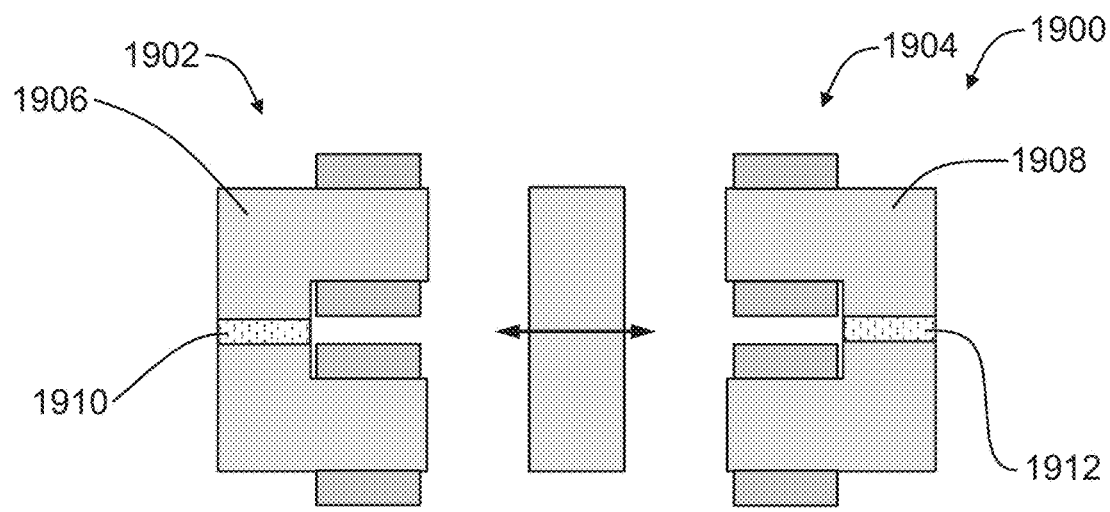
FIGS. 19A-19C depict variations of electromagnetic actuator systems.
Figure 19B:
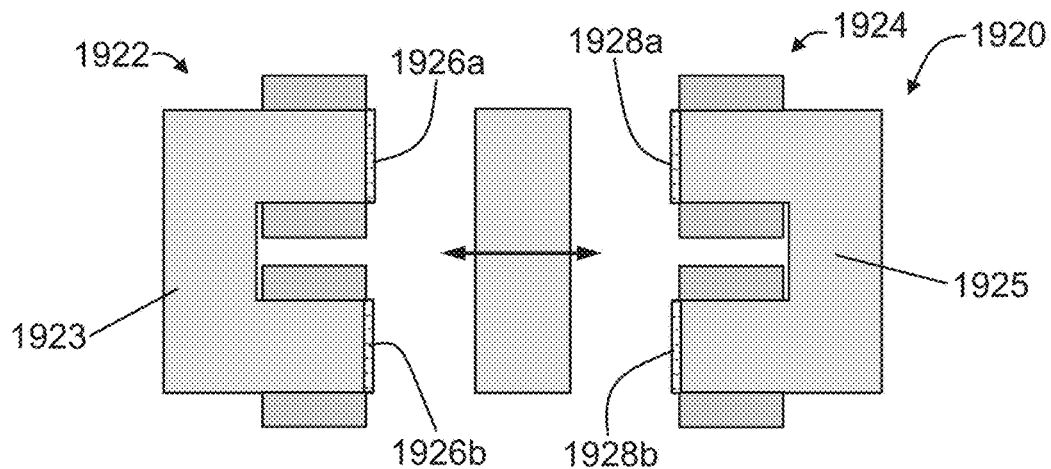
Figure 19C:
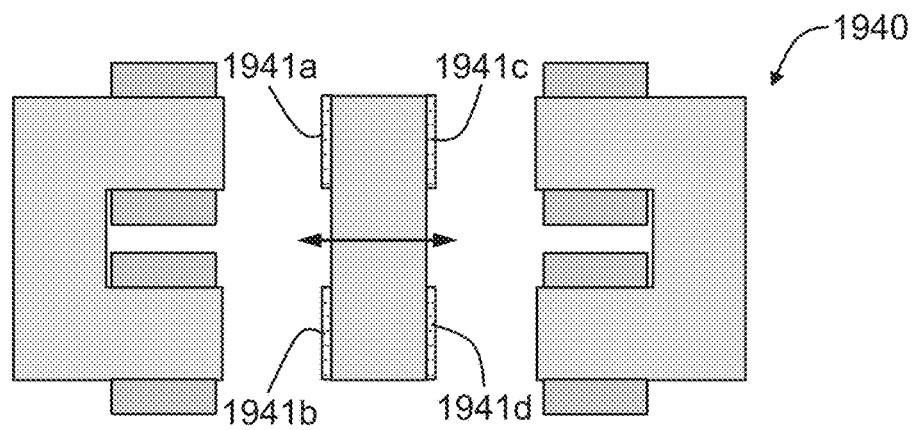

FIGS. 19A-19C depict various electromagnetic actuation systems that comprise one or more permanent magnets. The actuation systems 1900, 1920, 1940 may be similar to the actuation system 1700 depicted in FIGS. 17A-17D, and may each comprise a movable member located in a gap between a first coiled assembly and a second coiled assembly. A collimator leaf may be attached to the movable member, as schematically depicted in FIG. 17B. The electromagnetic actuation system 1900 may comprise a first coiled assembly 1902 having first and second coils with a first core 1906 disposed within the lumens of the first and second coils, and a second coiled assembly 1904 having first and second coils with a second core 1908 disposed within the lumens of the first and second coils. The first core 1906 and the second core 1908 may each comprise a permanent magnet 1910, 1912. For example, the first and second cores may be C-shaped, and a permanent magnet may be located along the vertical length of the "C" (e.g., located along the length of the core that spans the gap between the first coil and the second coil of the coiled assembly). Alternatively or additionally, one or more permanent magnets may be located at the ends of the C-shaped core. For example, the electromagnetic actuation system 1920 may comprise a first coil assembly 1922 and a second coil assembly 1924, where the first coil assembly 1922 comprises a first C-shaped core 1923, a first permanent magnet 1926a and a second permanent magnet 1926b, and the second coil assembly comprises a second C-shaped core 1925, a third permanent magnet 1928a, and a fourth permanent magnet 1928b. The first permanent magnet 1926a may be located at a first end of the core 1923 and the second permanent magnet 1926b may be located at a second end of the core 1923. The third permanent magnet 1928a may be located at a first end of the core 1925 and the fourth permanent magnet 1928b may be located at a second end of the core 1925. The permanent magnets 1926a,b and 1928a,b may cover at least a portion of the surface of the end of the cores 1923, 1925, or may cover the entire surface of the end of the cores. Alternatively or additionally, the movable member may comprise one or more permanent magnets that are located on the surface of the movable member. For example, the electromagnetic actuation system 1940 may comprise a movable member having a first permanent magnet 1941a, a second permanent magnet 1941b, a third permanent magnet 1941c, a fourth permanent magnet 1941d located on the surface of the movable member. In this variation, the first permanent magnet 1941a is located on the movable member such that it is aligned with a first end surface of the C-shaped core of the first coil assembly and the second permanent magnet 1941b is located on the movable member such that it is aligned with a second end surface of the C-shaped core of the first coil assembly. The third permanent magnet 1941c is located on the movable member such that it is aligned with a first end surface of the C-shaped core of the second coil assembly and the fourth permanent magnet 1941d is located on the movable member such that it is aligned with a second end surface of the C-shaped core of the second coil assembly.

Optionally, a multi-leaf collimator using any of the leaf drive mechanisms described herein may comprise a return or recoil spring such that the spring system and/or actuator system moves the leaf in one direction while the recoil spring moves the leaf in the opposite direction. This may help to simply the mechanics of the leaf drive mechanism so that the mechanism provides a force in just one direction while the recoil spring provides a force in the opposite direction. In some variations, this may reduce the number of components for the leaf drive mechanism and allow for a more compact collimator. For example, the spring system and/or actuator system of a leaf drive mechanism may be configured to move the leaf from the closed position to the open position, where the applied force stores potential energy in a recoil spring. Once the spring system or actuator system is in a state that allows the leaf to move, the recoil spring then uses the potential energy to move the leaf from the open position back to the closed position. Alternatively, the leaf actuation mechanism may be configured to move the leaf from the open position to the closed position and the recoil spring may be configured to move the leaf from the closed position to the open position. The return or recoil spring may be a coil spring, torsion spring, or torsion bar. Some variations may comprise a plurality of recoil springs in parallel. The spring distortion may be extension, compression, or some combination thereof across multiple springs. Although this arrangement may require the spring system and/or actuator system of the leaf drive mechanism to be capable of applying a force against the recoil spring in order to transition the leaf from a first position to a second position (which may double the force of that transition), no additional force is needed to transition the leaf from the second position back to the first position.

While the drive mechanisms disclosed herein are described in the context of moving collimator leaves for a high bandwidth binary multi-leaf collimator, it should be understood that such drive mechanisms may be also be used in other systems. For example, such drive mechanisms may be used to move the leaves of a collimator for conformal radiotherapy and/or IMRT.

What is claimed as new and desired to be protected by Letters Patent of the United States is:

1. A collimator comprising:
   a leaf movable between a first position and a second position;
   a leaf shaft having a proximal portion and a distal portion, and wherein the distal portion of the shaft is attached to the leaf;
   a spring system coupled to the leaf; and
   an actuator system coupled to the leaf shaft wherein a motive force generated by the spring system and a motive force generated by the actuator system longitudinally translate the leaf from the first to the second position, and wherein the actuator system is configured to selectively retain the leaf at the first position or the second position, and
   wherein the actuator system comprises a first electromagnet and a second electromagnet separated by a space from the first electromagnet, and a ferromagnetic movable member movable across the space between the first and second electromagnets, wherein the leaf shaft is connected to the movable member, and wherein the actuator system comprises a first configuration wherein either the first or second electromagnet is activated such that the movable member is secured at a location of either the first or second electromagnet, and a second configuration wherein the first and second electromagnets are alternately activated such that the movable member is movable within the space.

2. The collimator of claim 1, wherein the motive force generated by the actuator system is sufficient to overcome losses in the spring system.

3. The collimator of claim 1, wherein the actuator system comprises a voice coil.

4. The collimator of claim 1, wherein the spring system comprises at least one coil spring.

5. The collimator of claim 1, wherein each of the first and second electromagnets comprises a pair of adjacent coil windings each having a lumen therethrough and a C-shaped core extending through the lumens of both of the coil windings.

6. The collimator of claim 1, wherein the movable member comprises a permanent magnet.

7. The collimator of claim 1, wherein the actuator system comprises a linear actuator.

8. The collimator of claim 1, wherein when the actuator system is in the first configuration, the leaf is in a closed configuration and wherein when the actuator system is in the second configuration, the leaf is in an open configuration, and wherein the spring system and actuator system are configured to transition the leaf between the closed configuration and open configuration in about 6 ms or less.

9. The collimator of claim 1, wherein the spring system comprises at least one torsion bar spring.

10. The collimator of claim 1, wherein the spring system is coupled to the leaf shaft.

11. The collimator of claim 10, wherein the spring system and the actuator system are coupled to the proximal portion of the leaf shaft.

12. The collimator of claim 11, wherein the spring system and the actuator system are attached to the proximal portion of the leaf shaft.

13. The collimator of claim 1, wherein the motive force generated by the spring system and the motive force generated by the actuator system longitudinally translate the leaf from the second position to the first position.

14. The collimator of claim 1, wherein the actuator system comprises a piezo actuator.

* * * * *